(12) United States Patent
Holsten et al.

(10) Patent No.: US 10,772,614 B2
(45) Date of Patent: Sep. 15, 2020

(54) SPECIMEN RETRIEVAL DEVICE

(71) Applicant: Covidien LP, Mansfield, MA (US)

(72) Inventors: Henry E. Holsten, Hamden, CT (US); Thomas Zammataro, Hamden, CT (US); Cody Pereira, Monroe, CT (US)

(73) Assignee: Covidien LP, Mansfield, MA (US)

( * ) Notice: Subject to any disclaimer, the term of this patent is extended or adjusted under 35 U.S.C. 154(b) by 192 days.

(21) Appl. No.: 16/016,715

(22) Filed: Jun. 25, 2018

(65) Prior Publication Data
US 2018/0296201 A1  Oct. 18, 2018

Related U.S. Application Data

(62) Division of application No. 14/910,740, filed as application No. PCT/US2014/052313 on Aug. 22, 2014, now Pat. No. 10,034,661.
(Continued)

(51) Int. Cl.
*A61B 17/00* (2006.01)
*A61B 17/3205* (2006.01)
*A61B 17/221* (2006.01)

(52) U.S. Cl.
CPC ...... *A61B 17/00234* (2013.01); *A61B 17/221* (2013.01); *A61B 17/32056* (2013.01);
(Continued)

(58) Field of Classification Search
CPC ............ A61B 17/00234; A61B 17/221; A61B 17/32056; A61B 2017/00287;
(Continued)

(56) References Cited

U.S. PATENT DOCUMENTS

| 30,471 A | 10/1860 | Dudley |
| 35,164 A | 5/1862 | Logan et al. |

(Continued)

FOREIGN PATENT DOCUMENTS

| DE | 3542667 A1 | 6/1986 |
| DE | 8435489 U1 | 8/1986 |

(Continued)

OTHER PUBLICATIONS

European Search Report EP 12191639.9 dated Feb. 20, 2013.
(Continued)

*Primary Examiner* — Robert A Lynch
(74) *Attorney, Agent, or Firm* — Carter, DeLuca & Farrell LLP

(57) ABSTRACT

A specimen retrieval device is having a housing, an outer shaft, and an inner shaft releasably supporting a pouch. The device may further include a stripper plate operably coupled to the inner shaft for movement between a retracted configuration, in which the pouch and the stripper plate are within the outer shaft, and a deployed configuration, in which the pouch and the stripper plate are outside of the outer shaft. The stripper plate may define major and minor axes, wherein the dimension along the major axis is greater than the inner diameter of the outer shaft, and the dimension along the minor axis is smaller than the inner diameter of the outer shaft. The stripper plate may include one or more apertures, e.g., to receive a support mechanism of the device, or a suture. The device may also include structure preventing premature deployment of the pouch and the stripper plate.

12 Claims, 44 Drawing Sheets

Related U.S. Application Data

(60) Provisional application No. 61/948,936, filed on Mar. 6, 2014, provisional application No. 61/899,361, filed on Nov. 4, 2013, provisional application No. 61/899,353, filed on Nov. 4, 2013, provisional application No. 61/899,357, filed on Nov. 4, 2013, provisional application No. 61/899,365, filed on Nov. 4, 2013, provisional application No. 61/869,141, filed on Aug. 23, 2013.

(52) U.S. Cl.
CPC ............... *A61B 2017/0046* (2013.01); *A61B 2017/00287* (2013.01); *A61B 2017/00367* (2013.01); *A61B 2017/2212* (2013.01)

(58) Field of Classification Search
CPC .. A61B 2017/00367; A61B 2017/0046; A61B 2017/2212
See application file for complete search history.

(56) References Cited

U.S. PATENT DOCUMENTS

| | | |
|---|---|---|
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |
| 4,991,593 A | 2/1991 | LeVahn |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,320,627 A | 6/1994 | Sorensen et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,755,724 A | 5/1998 | Yoon |
| 5,759,187 A | 6/1998 | Nakao et al. |
| 5,769,794 A | 6/1998 | Conlan et al. |
| 5,782,840 A | 7/1998 | Nakao |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,895,392 A | 4/1999 | Riek et al. |
| 5,904,690 A | 5/1999 | Middleman et al. |
| 5,906,621 A | 5/1999 | Secrest et al. |
| 5,908,429 A | 6/1999 | Yoon |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,156,055 A | 12/2000 | Ravenscroft |
| 6,162,235 A | 12/2000 | Vaitekunas |
| 6,165,121 A | 12/2000 | Alferness |
| 6,168,603 B1 | 1/2001 | Leslie et al. |
| 6,206,889 B1 | 3/2001 | Bennardo |
| 6,228,095 B1 | 5/2001 | Dennis |
| 6,258,102 B1 | 7/2001 | Pagedas |
| 6,264,663 B1 | 7/2001 | Cano |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,368,328 B1 | 4/2002 | Chu et al. |
| 6,383,195 B1 | 5/2002 | Richard |
| 6,383,196 B1 | 5/2002 | Leslie et al. |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,547,310 B2 | 4/2003 | Myers |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,958,069 B2 | 10/2005 | Shipp et al. |
| 6,971,988 B2 | 12/2005 | Orban, III |
| 6,994,696 B2 | 2/2006 | Suga |
| 7,014,648 B2 | 3/2006 | Ambrisco et al. |

(56) References Cited

U.S. PATENT DOCUMENTS

| | | |
|---|---|---|
| 7,018,373 B2 | 3/2006 | Suzuki |
| 7,052,454 B2 | 5/2006 | Taylor |
| 7,052,501 B2 | 5/2006 | McGuckin, Jr. |
| 7,090,637 B2 | 8/2006 | Danitz at al. |
| 7,115,125 B2 | 10/2006 | Nakao et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 7,618,437 B2 | 11/2009 | Nakao |
| 7,670,346 B2 | 3/2010 | Whitfield |
| 7,722,626 B2 | 5/2010 | Middleman et al. |
| 7,762,959 B2 | 7/2010 | Bilsbury |
| 7,785,251 B2 | 8/2010 | Wilk |
| 7,819,121 B2 | 10/2010 | Amer |
| 7,837,612 B2 | 11/2010 | Gill et al. |
| RE42,050 E | 1/2011 | Richard |
| 7,892,242 B2 | 2/2011 | Goldstein |
| 8,016,771 B2 | 9/2011 | Orban, III |
| 8,057,485 B2 | 11/2011 | Hollis et al. |
| 8,075,567 B2 | 12/2011 | Taylor et al. |
| 8,097,001 B2 | 1/2012 | Nakao |
| 8,152,820 B2 | 4/2012 | Mohamed et al. |
| 8,172,772 B2 | 5/2012 | Zwolinski et al. |
| 8,206,401 B2 | 6/2012 | Nakao |
| 8,337,510 B2 | 12/2012 | Rieber et al. |
| 8,343,031 B2 | 1/2013 | Gertner |
| 8,348,827 B2 | 1/2013 | Zwolinski |
| 8,388,630 B2 | 3/2013 | Teague et al. |
| 8,409,112 B2 | 4/2013 | Wynne et al. |
| 8,409,216 B2 | 4/2013 | Parihar et al. |
| 8,409,217 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,696,683 B2 | 4/2014 | LeVert |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,906,036 B2 | 12/2014 | Farascioni |
| 8,956,370 B2 | 2/2015 | Taylor et al. |
| 8,968,329 B2 | 3/2015 | Cabrera |
| 10,034,661 B2 | 7/2018 | Holsten et al. |
| 2002/0068943 A1 | 6/2002 | Chu et al. |
| 2002/0082516 A1 | 6/2002 | Stefanchik |
| 2003/0073970 A1 | 4/2003 | Suga |
| 2003/0100909 A1 | 5/2003 | Suzuki |
| 2003/0100919 A1 | 5/2003 | Hopkins et al. |
| 2003/0199915 A1 | 10/2003 | Shimm |
| 2003/0216773 A1 | 11/2003 | Shimm |
| 2004/0097960 A1 | 5/2004 | Terachi et al. |
| 2004/0138587 A1 | 7/2004 | Lyons |
| 2005/0085808 A1 | 4/2005 | Nakao |
| 2005/0165411 A1 | 7/2005 | Orban |
| 2005/0267492 A1 | 12/2005 | Poncet et al. |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2007/0186935 A1 | 8/2007 | Wang et al. |
| 2008/0188766 A1 | 8/2008 | Gertner |
| 2008/0221587 A1 | 9/2008 | Schwartz |
| 2008/0221588 A1 | 9/2008 | Hollis et al. |
| 2008/0234696 A1* | 9/2008 | Taylor ............... A61B 17/00234 606/114 |
| 2008/0300621 A1 | 12/2008 | Hopkins |
| 2008/0312496 A1 | 12/2008 | Zwolinski |
| 2009/0043315 A1 | 2/2009 | Moon |
| 2009/0082779 A1 | 3/2009 | Nakao |
| 2009/0182292 A1 | 7/2009 | Egle et al. |
| 2009/0192510 A1 | 7/2009 | Bahney |
| 2009/0240238 A1 | 9/2009 | Grodrian et al. |
| 2010/0000471 A1 | 1/2010 | Hibbard |
| 2010/0152746 A1 | 6/2010 | Ceniccola et al. |
| 2011/0087235 A1 | 4/2011 | Taylor et al. |
| 2011/0184311 A1 | 7/2011 | Parihar et al. |
| 2011/0184433 A1 | 7/2011 | Parihar et al. |
| 2011/0184434 A1 | 7/2011 | Parihar et al. |
| 2011/0184435 A1 | 7/2011 | Parihar et al. |
| 2011/0184436 A1 | 7/2011 | Shelton, IV et al. |
| 2011/0190779 A1 | 8/2011 | Gell et al. |
| 2011/0190781 A1 | 8/2011 | Collier et al. |
| 2011/0190782 A1 | 8/2011 | Fleming et al. |
| 2011/0264091 A1 | 10/2011 | Koppleman et al. |
| 2011/0299799 A1 | 12/2011 | Towe |
| 2012/0046667 A1 | 2/2012 | Cherry et al. |
| 2012/0083795 A1 | 4/2012 | Fleming et al. |
| 2012/0083796 A1 | 4/2012 | Grover et al. |
| 2012/0203241 A1 | 8/2012 | Williamson, IV |
| 2013/0023895 A1 | 1/2013 | Saleh |
| 2013/0103042 A1 | 4/2013 | Davis |
| 2013/0116592 A1 | 5/2013 | Whitfield |
| 2013/0190773 A1 | 7/2013 | Carlson |
| 2013/0218170 A1 | 8/2013 | Uznanski et al. |
| 2013/0245636 A1 | 9/2013 | Jansen |
| 2013/0274758 A1 | 10/2013 | Young et al. |
| 2013/0325025 A1 | 12/2013 | Hathaway et al. |
| 2014/0046337 A1 | 2/2014 | O'Prey et al. |
| 2014/0058403 A1 | 2/2014 | Menn et al. |
| 2014/0180303 A1 | 6/2014 | Duncan et al. |
| 2014/0222016 A1 | 8/2014 | Grover et al. |
| 2014/0236110 A1 | 8/2014 | Taylor et al. |
| 2014/0243865 A1 | 8/2014 | Swayze et al. |
| 2014/0249541 A1 | 9/2014 | Kahle et al. |
| 2014/0276913 A1 | 9/2014 | Tah et al. |
| 2014/0303640 A1 | 10/2014 | Davis et al. |
| 2014/0309656 A1 | 10/2014 | Gal et al. |
| 2014/0330285 A1 | 11/2014 | Rosenblatt et al. |
| 2014/0350567 A1 | 11/2014 | Schmitz et al. |
| 2014/0371759 A1 | 12/2014 | Hartoumbekis |
| 2014/0371760 A1 | 12/2014 | Menn |
| 2015/0018837 A1 | 1/2015 | Sartor et al. |
| 2015/0045808 A1 | 2/2015 | Farascioni |

FOREIGN PATENT DOCUMENTS

| | | |
|---|---|---|
| DE | 4204210 A1 | 8/1992 |
| DE | 19624826 A1 | 1/1998 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2436313 A2 | 4/2012 |
| FR | 1272412 A | 9/1961 |
| GB | 246009 A | 1/1926 |
| WO | 9315671 A1 | 8/1993 |
| WO | 9315675 A1 | 8/1993 |
| WO | 9509666 A1 | 4/1995 |
| WO | 0135831 A1 | 5/2001 |
| WO | 2004002334 A1 | 1/2004 |
| WO | 2004112571 A2 | 12/2004 |

(56) References Cited

FOREIGN PATENT DOCUMENTS

| WO | 2005112783 | A1 | 12/2005 |
|---|---|---|---|
| WO | 2006110733 | | 10/2006 |
| WO | 2007048078 | A1 | 4/2007 |
| WO | 2007048085 | A2 | 4/2007 |
| WO | 2008114234 | A2 | 9/2008 |
| WO | 2009149146 | A1 | 12/2009 |
| WO | 2011090862 | A2 | 7/2011 |

OTHER PUBLICATIONS

European Search Report EP 11250837.9 dated Sep. 10, 2013.
European Search Report EP 11250838.7 dated Sep. 10, 2013.
European Search Report EP 13170118.7 dated Dec. 5, 2013.
European Search Report EP 12165852 dated Jun. 20, 2012.
http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.
European Office Action dated Apr. 7, 2017, issued in EP Application No. 14 761 498.
Chinese Office Action dated Aug. 2, 2017, issued in CN Application No. 2014800584186.
Chinese Office Action dated Apr. 25, 2018, in Chinese Appln. No. 201480058418.

\* cited by examiner

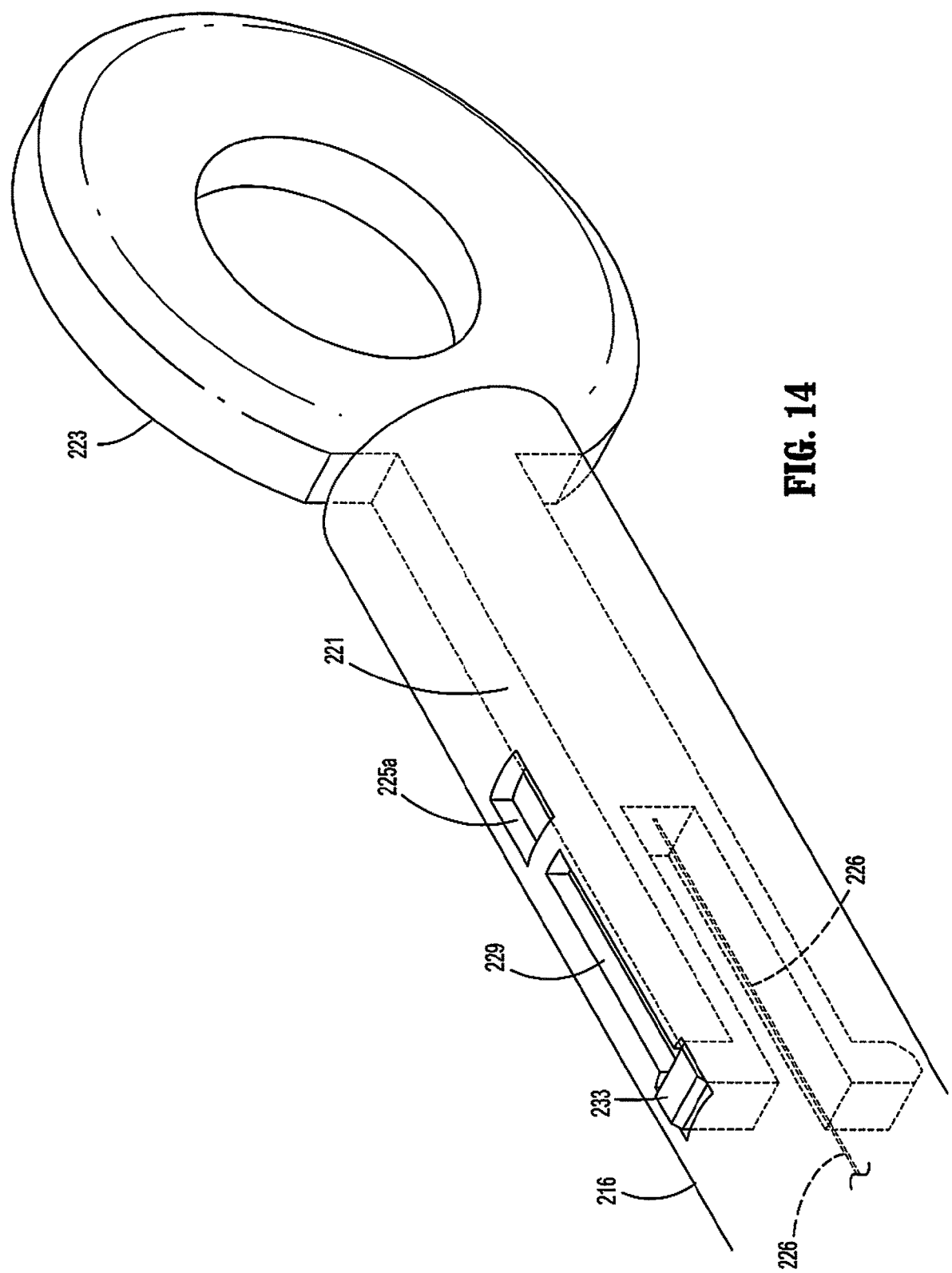

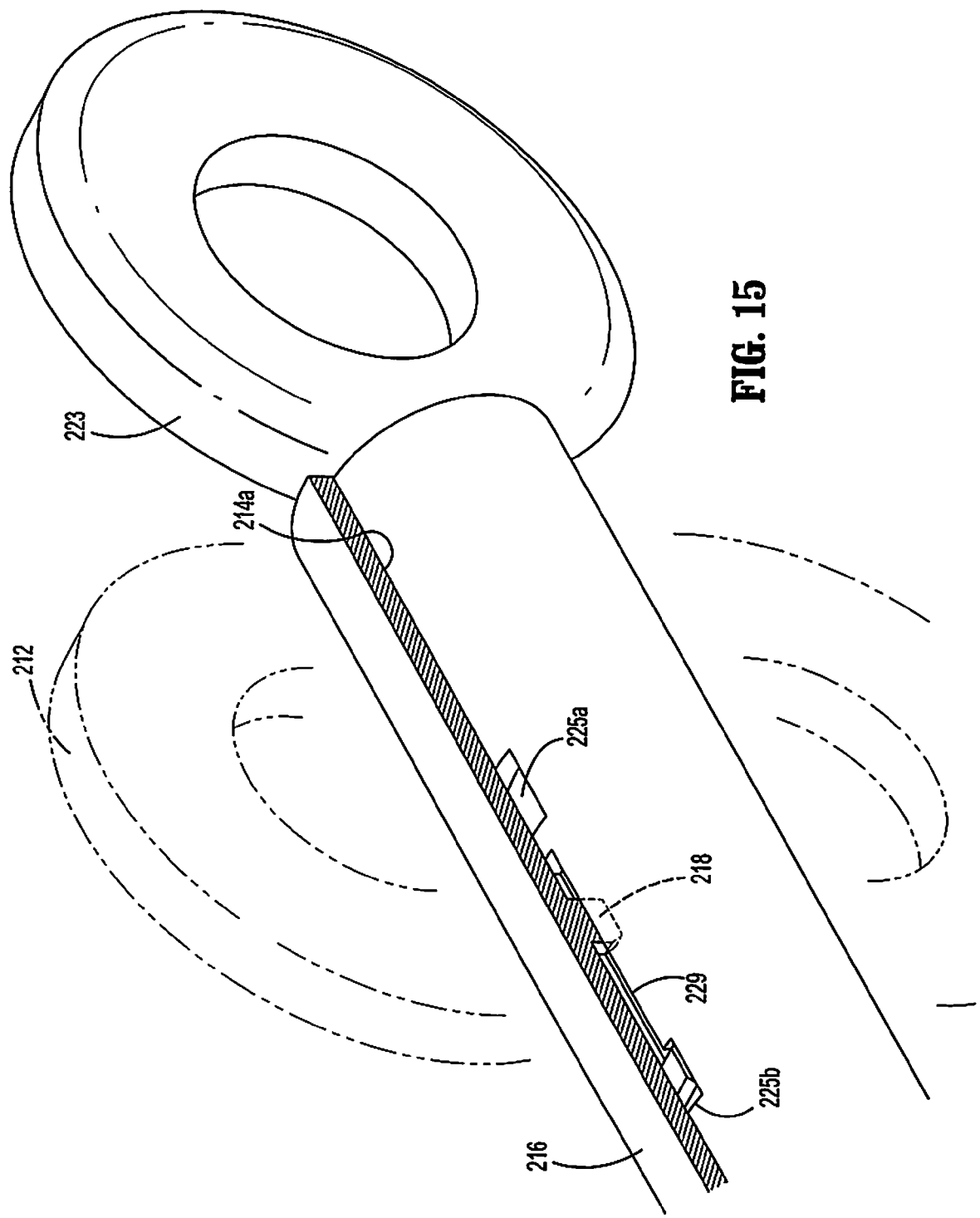

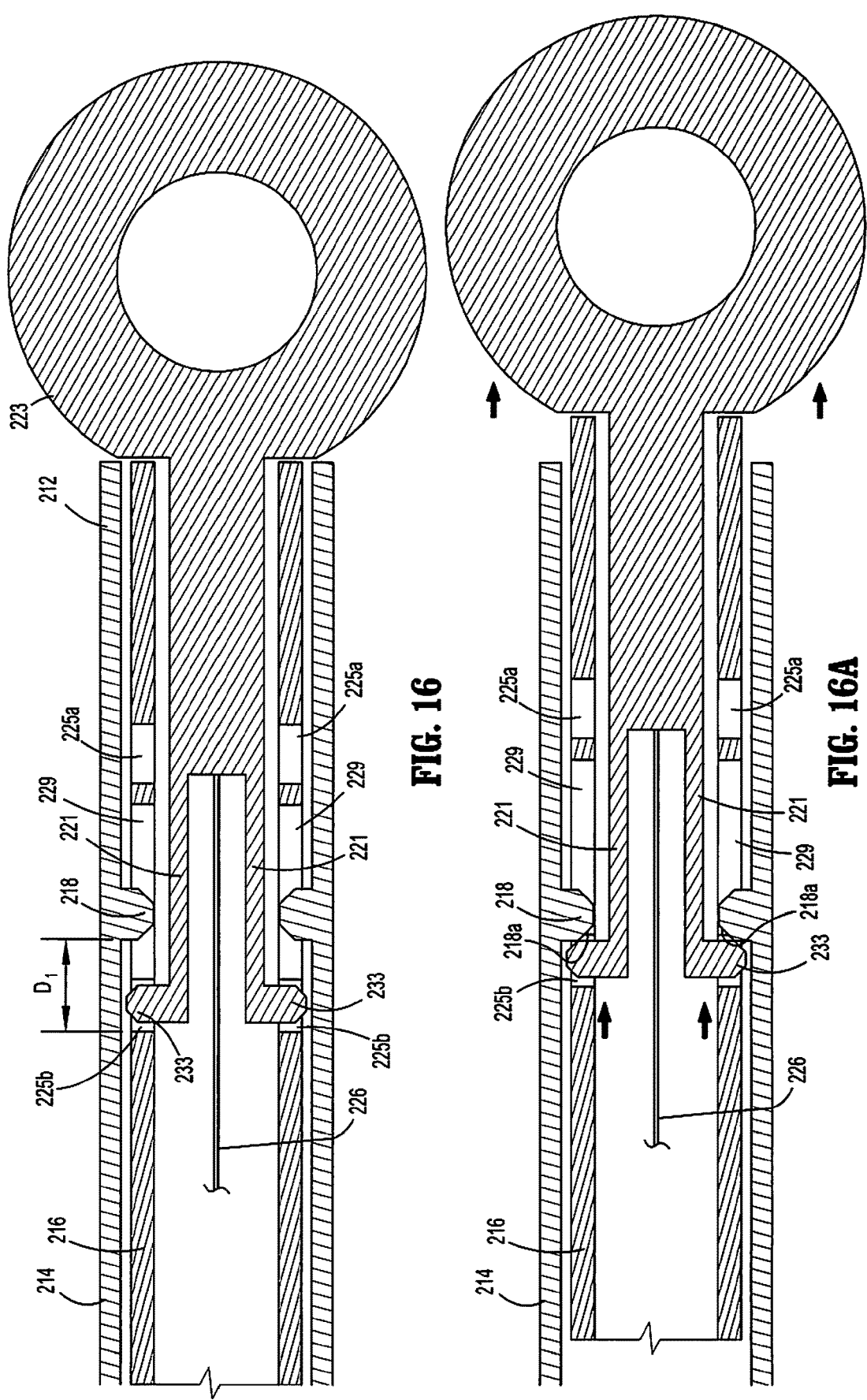

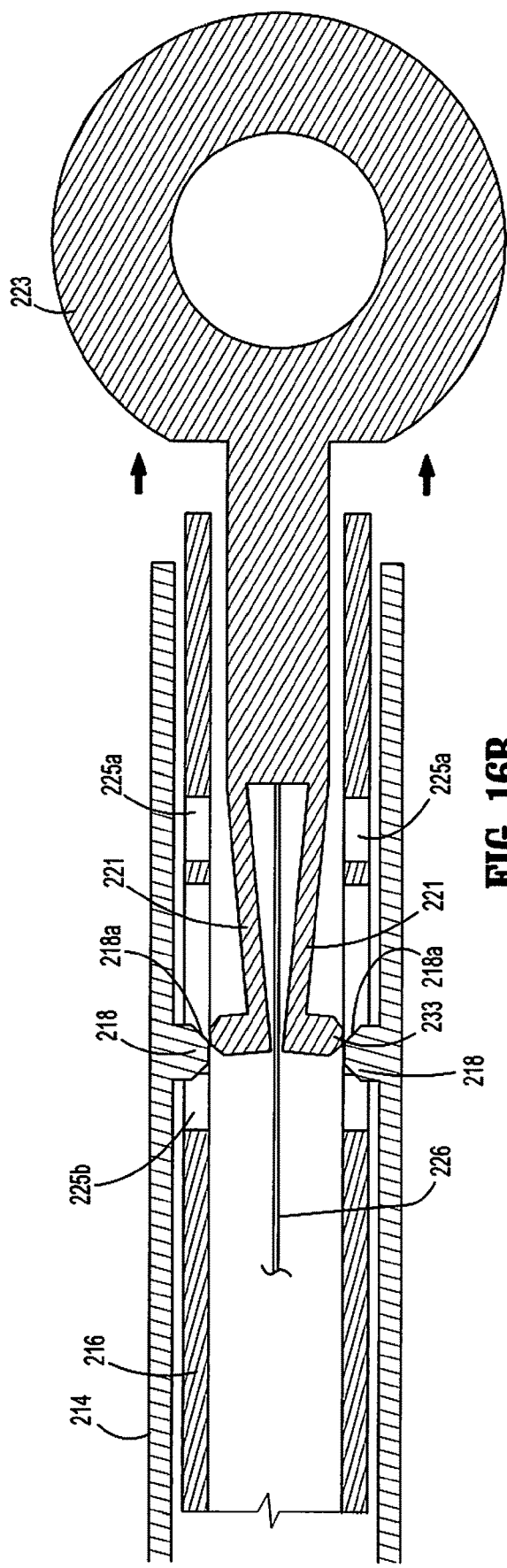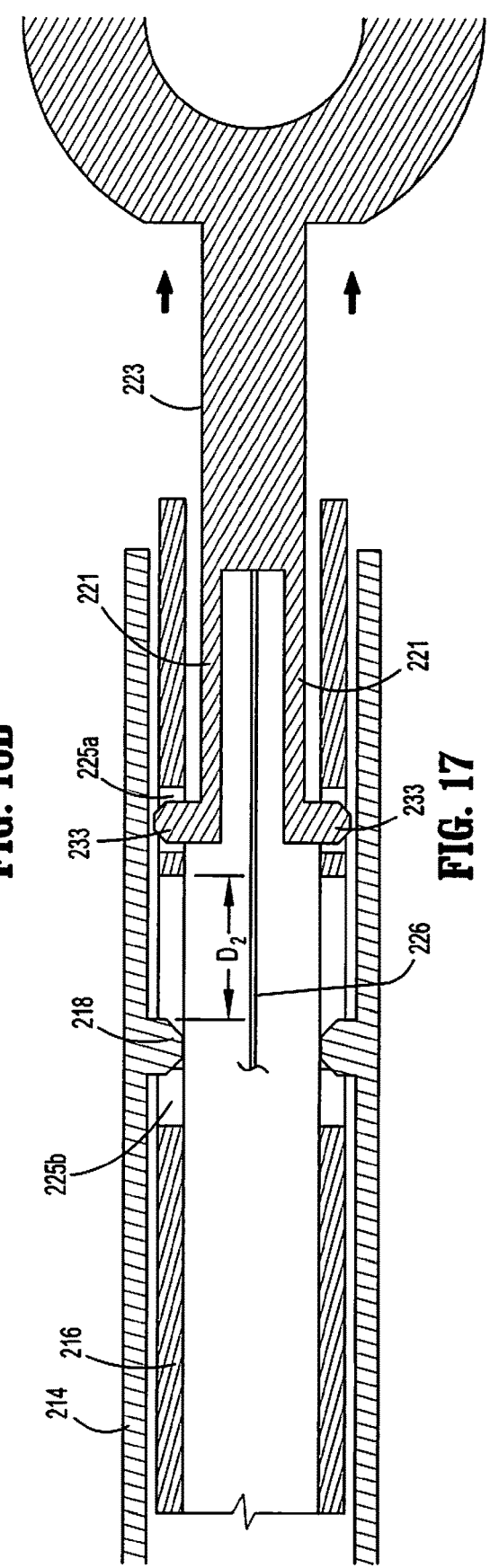
FIG. 16B
FIG. 17

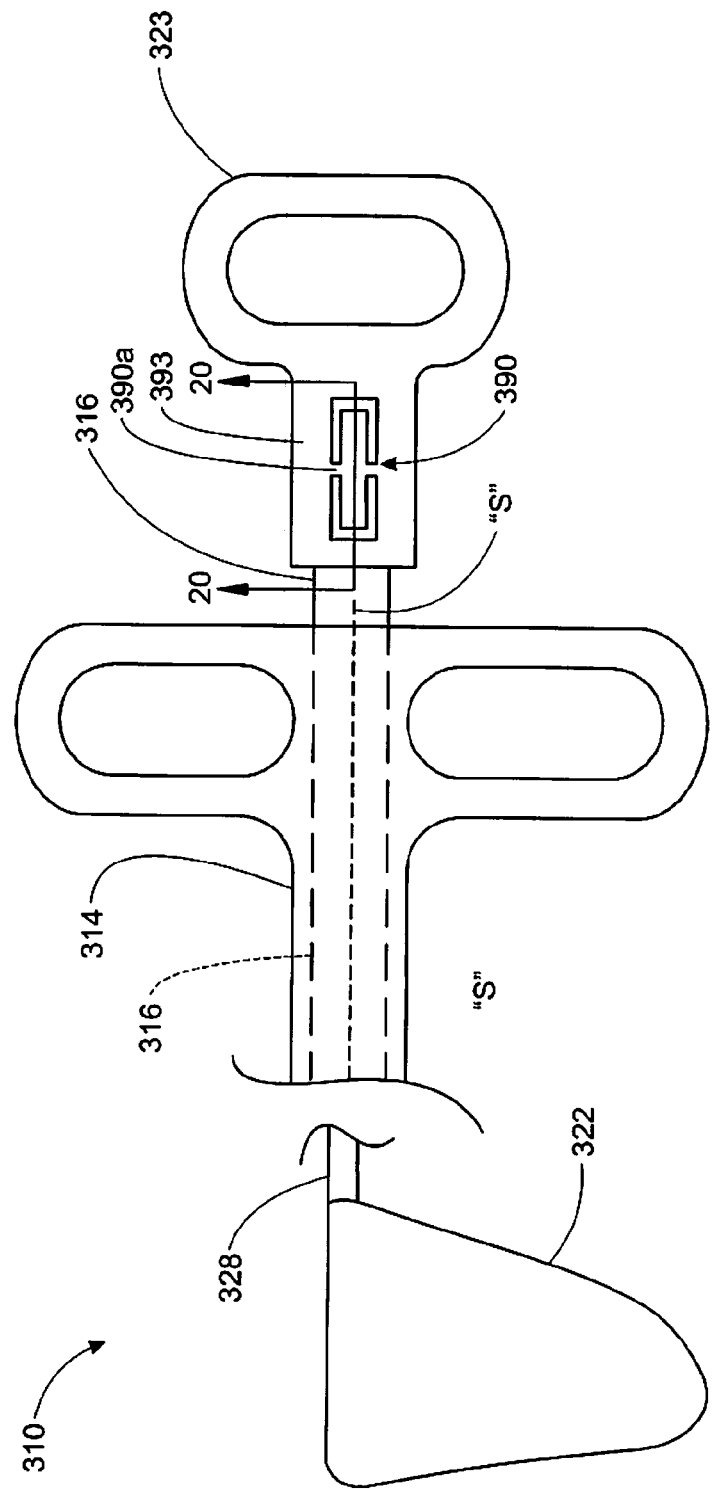
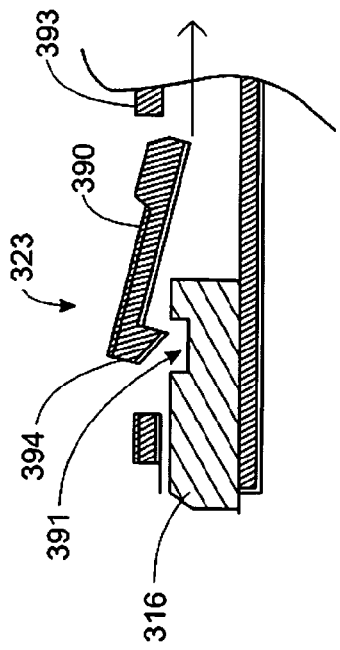
FIG. 19
FIG. 20
FIG. 21

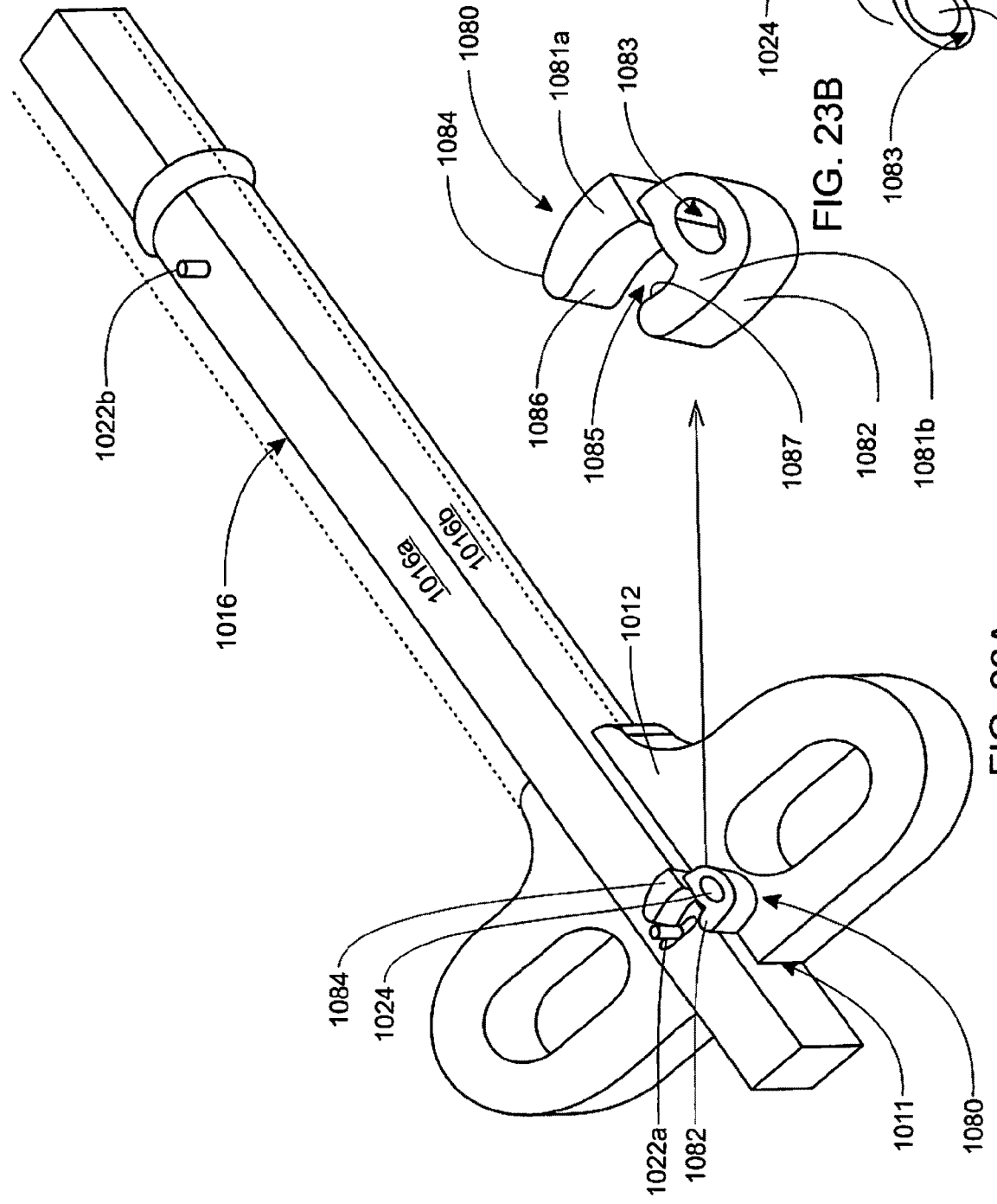

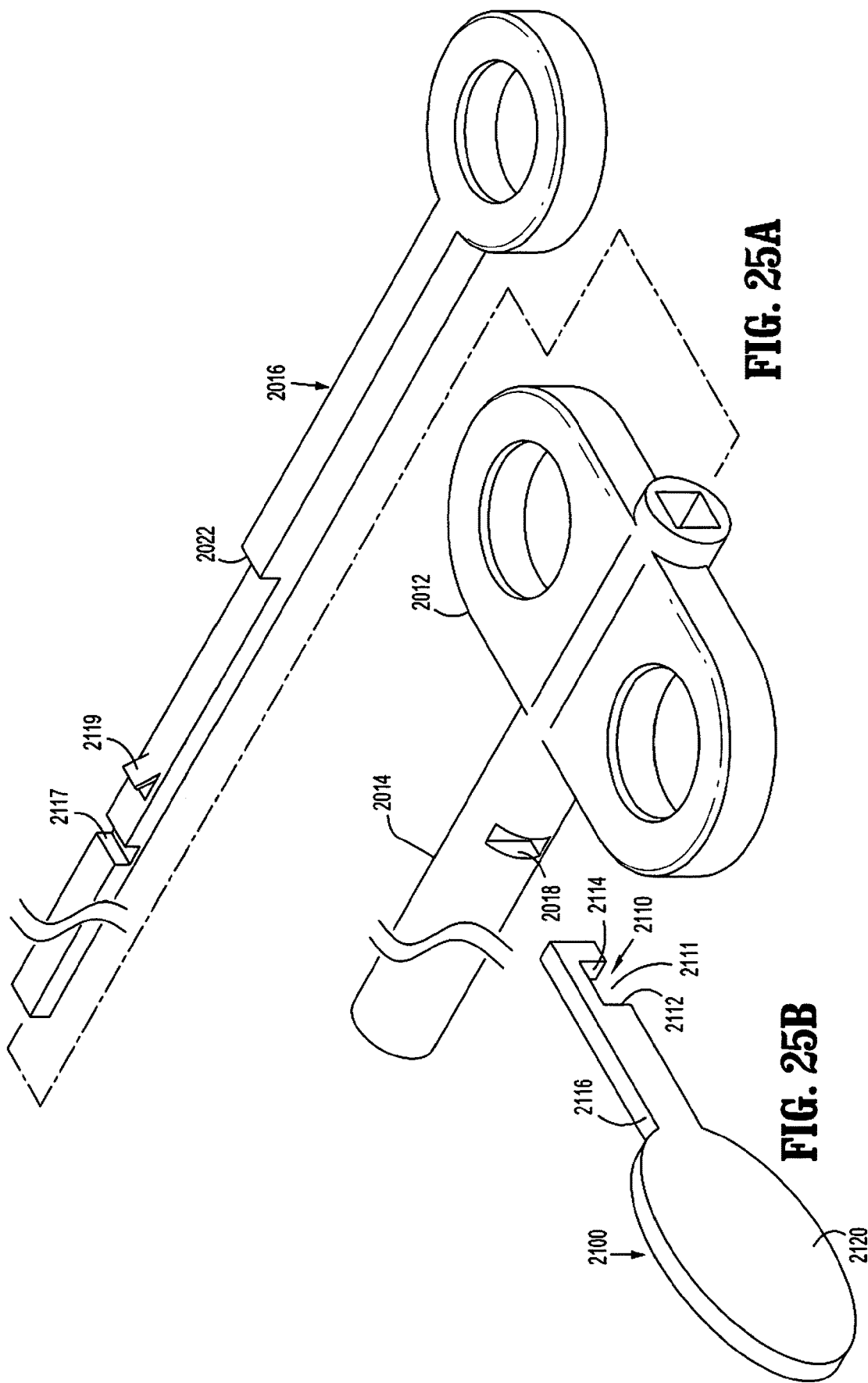

SPECIMEN RETRIEVAL DEVICE

CROSS-REFERENCE TO RELATED APPLICATIONS

This application is a divisional of U.S. patent application Ser. No. 14/910,740 filed Feb. 8, 2016, which is a National Stage Application of PCT/US14/52313 under 35USC § 371(a), which claims benefit of and priority to U.S. Provisional Patent Application Ser. Nos. 61/948,936 filed Mar. 6, 2014, 61/899,365 filed Nov. 4, 2013, 61/899,361 filed Nov. 4, 2013, 61/899,357 filed Nov. 4, 2013, 61/899,353 filed Nov. 4, 2013, 61/869,141 filed Aug. 23, 2013, the disclosures of each of the above-identified applications are hereby incorporated by reference in their entirety.

BACKGROUND

Technical Field

The present disclosure relates to specimen retrieval devices. More specifically, the present disclosure relates to specimen retrieval devices including a detachable pouch, structure to facilitate detachment of the pouch, and/or structure to prevent inadvertent detachment of the pouch.

Background of Related Art

Laparoscopic and endoscopic surgical procedures are minimally invasive procedures in which operations are carried out within the body by means of elongated instruments inserted through small entrance or access openings in the body, e.g., an opening defined by a natural passageway of the body, an opening created by a tissue piercing instrument (e.g., a trocar), etc.

Minimally invasive procedures are often used to partially or totally remove body tissue or organs from the interior of the body, e.g. nephrectomy, cholecystectomy, duodenectomy, ileectomy, jejunectomy and other such procedures. During such procedures, it is common that affected tissue or organs must be removed via the access opening in the skin, or through a cannula. Various types of retrieval devices are known in the art to facilitate these procedures.

Conventional retrieval devices typically include an elongated applicator including a handle at a proximal end that is operable to deploy a pouch or other suitable containment device from a distal shaft. The pouch may be perforated and releasably coupled to a support member along the perforations. As a result of the perforations on the pouch, the pouch may be detached from the support member by tearing along the perforations.

The pouch is typically folded or rolled and stored within an outer shaft during packaging and shipping of the retrieval device. However, shipping the pouch in this folded or rolled manner may result in undesirable memory wrinkles being formed thereon, which, in turn, may make it more difficult for a clinician to open the pouch when it is deployed from the applicator.

One or more devices or components may be utilized to separate the pouch from the spring to facilitate removal, e.g., a stripper plate. Typically, once the pouch is deployed from the distal shaft and the retrieval device is manipulated to capture a specimen, releasing the pouch from the support member may be facilitated by the stripper plate. As can be appreciated, it is advantageous to ship the stripper plate in a retracted orientation to reduce the risk of inadvertent detachment of the pouch from the spring. Thus, there exists a need to provide a retrieval device that can be packaged and shipped with the pouch in a deployed position and the stripper plate 14 in a retracted position. In addition, there exists a need for a retrieval device that includes structure to prevent inadvertent deployment of the stripper plate from the retracted position during shipping and during initial handling of the retrieval device.

SUMMARY

One aspect of the disclosure is directed to a specimen retrieval device including a housing, an outer shaft extending distally from the housing and defining a longitudinal bore and an inner shaft movably disposed within the longitudinal bore of the outer shaft. A retention member is movably supported on a distal end of the inner shaft and a pouch is supported on a distal end of the inner shaft. The retention member is movably supported in relation to the inner shaft from a first position preventing separation of the pouch from the distal end of the inner shaft to a second position permitting separation of the pouch from the inner shaft.

In some embodiments, the distal end of the inner shaft includes at least one protrusion and the pouch defines at least one opening. The at least one protrusion of the inner shaft is received within the at least one opening of the pouch to support the pouch on the distal end of the inner shaft.

In embodiments, the retention member is configured to engage the at least one protrusion to prevent separation of the pouch from the at least one protrusion.

In certain embodiments, each of the at least one protrusion defines a bore and the retention member is configured to extend through the bore to retain the pouch on the at least one protrusion.

In some embodiments, the at least one protrusion includes two protrusions and the at least one opening includes two openings.

In embodiments, the retention member includes a bifurcated member having a first portion configured to extend through the opening in one of the two protrusions and a second portion configured to extend through the opening in the other protrusion.

In certain embodiments, a sled is operably coupled to the retention member via at least one coupling device and the sled is movably supported on the inner shaft proximally of the retention member.

In some embodiments, the at least one coupling device is a wire having a distal end coupled to a proximal end of the retention member and a proximal end coupled to a distal end of the sled.

In embodiments, the housing defines a stop member and the sled includes a resilient finger portion that is positioned to engage the stop member when the inner shaft is in a fully retracted position such that upon movement of the inner shaft distally from the fully retracted position towards an extended position, the inner shaft initially moves independently of the sled and the retention member to disengage the retention member from the at least one protrusion of the inner shaft.

In certain embodiments, the sled is movably supported within a notch defined on the inner shaft. The notch may extend along a top wall portion of the inner shaft.

In some embodiments, the inner shaft includes a wall portion that is configured to urge the resilient finger portion of the sled downwardly when the inner shaft is moved distally in relation to the outer shaft from the fully retracted position towards the extended position to disengage the resilient finger portion from the stop member of the housing.

In embodiments, the stop member is defined along an interior wall of the housing.

In some embodiments, a cover plate is operably disposed adjacent the distal end of the inner shaft and is configured to secure the retention member to the inner shaft.

Another aspect of the disclosure is directed to a specimen retrieval device that includes a housing, an outer shaft extending distally from the housing and defining a longitudinal bore, a pouch including at least one tab, and an inner shaft disposed within the longitudinal bore of the outer shaft and releasably supporting the pouch at a distal end thereof. The inner shaft may include at least one protrusion configured to releasably engage the at least one proximal tab of the pouch. A sled and a retention member are slidingly disposed on the inner shaft and the retention member is configured to engage the at least one protrusion of the inner shaft to secure the pouch to the inner shaft. At least one coupling member is provided for coupling the sled to the retention member. A stop member is supported on the housing and is positioned distally of and in alignment with the sled when the inner shaft is in a fully retracted position, wherein distal translation of the inner shaft in relation to the outer shaft from the fully retracted position towards an extended position causes the sled to engage the stop member of the housing to cause the inner shaft to move distally independently of the sled and the retention member to effect disengagement of the retention member from the at least one protrusion of the inner shaft to facilitate release of the pouch from the inner shaft.

In embodiments, the sled includes a resilient finger portion configured to engage the stop member of the housing when the inner shaft is moved distally in relation to the outer shaft from the fully retracted position towards the extended position.

In certain embodiments, the sled is slidably received within a notch that is defined on the inner shaft. A top wall portion of the inner shaft may be configured to urge the resilient finger of the sled downwardly when the inner shaft is moved distally in relation to the outer shaft to disengage the resilient finger from the stop member.

In some embodiments, the stop member is defined along an interior wall of the housing.

In embodiments, the at least one protrusion defines a bore configured to receive a distal end of the retention member to releasably secure the pouch to the inner shaft such that distal movement of the inner shaft in relation to the retention member disengages the retention member from the bore of the at least one protrusion.

In certain embodiments, each of the at least one protrusion includes a proximal chamfer to facilitate separation of the pouch from the inner shaft.

In another aspect of the present disclosure, a specimen retrieval device includes a housing, an outer shaft extending distally from the housing and defining a longitudinal bore and a longitudinal axis, an inner shaft disposed within the longitudinal bore of the outer shaft, a support mechanism extending from a distal end of the inner shaft, a pouch supported on the support mechanism at the distal end of the inner shaft, and a stripper plate supported within a distal end of the outer shaft. The stripper plate defines a first aperture configured to receive the support mechanism and is movable in response to distal movement of the inner shaft from a retracted position disposed within the distal end of the outer shaft to a deployed position wherein the stripper plate is disposed outside of the outer shaft. When the stripper plate is in the deployed configuration, proximal movement of the inner shaft relative to the outer shaft causes the stripper plate to engage a distal end of the outer shaft and the pouch to engage a leading end of the stripper plate such that further proximal movement of the inner shaft effects separation of the pouch from the support mechanism of the inner shaft.

In some embodiments, the stripper plate has a generally elliptical configuration defining major and minor axes. The stripper plate is oriented within the distal end of the outer shaft in a retracted position to define a first angle with respect to the longitudinal axis of the outer shaft and is positioned externally of the outer shaft in a deployed position to define a second angle with respect to the longitudinal axis of the outer shaft.

In embodiments, a width of the minor axis is smaller than an inner diameter of the outer shaft and a width of the major axis is greater than the inner diameter of the outer shaft.

In certain embodiments, the stripper plate includes a second aperture wherein the first aperture of the stripper plate has a generally circumferential shape and is configured to receive the support mechanism and the second aperture has a generally triangular shape and is configured to receive a cinch of the specimen retrieval device.

In some embodiments, the second aperture is further defined by an upper first portion, an upper second portion and a lower portion. Each of the upper first and second portions is defined by generally circumferential walls and the lower portion is defined by a generally concave wall.

In embodiments, first and second opposing channels are provided between the upper first and second portions, respectively, and the lower portion wherein the upper first and second portions are configured to receive portions of the cinch of the specimen retrieval device. In embodiments, the upper first and second portions are sized proportionally to the cinch to exert a drag force thereupon as the cinch is being pulled through the first and second portions.

In some embodiments, the leading end of the stripper plate includes a generally planar configuration.

In certain embodiments, the stripper plate includes a trailing end and a beveled peripheral wall defining an angle in relation to the leading end of the stripper plate that ranges from 25 degrees to 45 degrees. In the retracted position, the first angle of the stripper plate may range from 1 degree to 75 degrees. In the deployed position, the second angle of the stripper plate may range from about 76 degrees to about 90 degrees.

In embodiments, a wedge member is releasably coupled to a proximal end of the inner shaft and is configured to prevent distal movement of the inner shaft relative to the outer shaft to a fully extended position to prevent the stripper plate from being moved to the deployed position.

In some embodiments, the at least one aperture of the stripper plate is further defined by first and second apertures wherein the first aperture of the stripper plate has a generally circumferential shape and is configured to receive the support mechanism and the second aperture has a generally triangular shape and is configured to receive a cinch of the specimen retrieval device.

In another aspect of the present disclosure, the specimen retrieval device includes a housing, an outer shaft extending distally from the housing and defining a longitudinal bore and a longitudinal axis, an inner shaft disposed within the longitudinal bore of the outer shaft, a pouch, a support mechanism secured to the distal end of the inner shaft configured to releasably support the pouch and a stripper plate supported on the support mechanism. The stripper plate has first and second apertures configured to receive the support mechanism and a cinch of the specimen retrieval device, respectively. The stripper plate is movable from a retracted position disposed within the outer shaft and oriented at a first angle relative to the longitudinal axis to a deployed position disposed outside of the outer shaft and oriented at a second angle relative to the longitudinal axis. When the stripper plate is in the deployed position, proximal movement of the inner shaft relative to the outer shaft causes a trailing end of the stripper plate to contact a distal end of the outer shaft and the pouch to engage a leading end of the stripper plate such that further proximal movement of the inner shaft in relation to the outer shaft from an extended position towards a retracted position uncouples the pouch from the support mechanism of the inner shaft.

In embodiments, the stripper plate includes a generally elliptical configuration defining a major and a minor axis. A width of the minor axis is smaller than an inner diameter of the outer shaft and a width of the major axis is greater than the inner diameter of the outer shaft.

In some embodiments, the first aperture of the stripper plate has a generally circumferential shape and is configured to receive the support mechanism and the second aperture has a generally triangular shape and is configured to receive a cinch of the specimen retrieval device.

In some embodiments, the second aperture is further defined by an upper first portion, an upper second portion and a lower portion. Each of the upper first and second portions is defined by generally circumferential walls and the lower portion is defined by a lower generally concave wall.

In certain embodiments, first and second opposing channels are provided between the upper first and second portions, respectively, and the lower portion.

In embodiments, the upper first and second portions are sized proportionally to the cinch to exert a drag force upon the cinch as the cinch is being pulled through the first or second portions.

In some embodiments, the leading end of the stripper plate has a generally planar configuration.

In certain embodiments, the stripper plate includes a generally oval shaped peripheral wall beveled at an angle that ranges from 25 degrees to 45 degrees in relation to the leading end of the stripper plate.

In embodiments, in the refracted position, the first angle of the stripper plate ranges from 1 degree to 75 degrees, and, in the deployed position, the second angle of the stripper plate ranges from 76 degrees to 90 degrees.

In some embodiments, a wedge member is releasably coupled to the inner shaft adjacent a proximal end of the inner shaft and is configured to prevent distal movement of the inner shaft relative to the outer shaft to a fully extended position to prevent the stripper shaft from being moved to the deployed position.

In embodiments, the first aperture of the stripper plate has a generally circumferential shape and is configured to receive the support mechanism and the second aperture has a generally triangular shape and is configured to receive a cinch of the specimen retrieval device.

In yet another aspect of the present disclosure, a specimen retrieval device includes an outer shaft defining a longitudinal bore and a longitudinal axis and including a blocking member, an inner shaft movably disposed within the longitudinal bore of the outer shaft and defining proximal and distal apertures, a support mechanism secured to a distal end of the inner shaft, a pouch releasably supported on the support mechanism, and an actuation device configured to engage the proximal end of the inner shaft. The actuation device includes at least one inwardly extending protrusion configured to be received within one of the proximal and distal apertures of the inner shaft to secure the actuation device to the inner shaft. In a partially retracted position of the inner shaft, the at least one inwardly extending protrusion of the actuation device is positioned within the distal aperture of the inner shaft to releasably secure the actuation device to the inner shaft in a first position, wherein proximal movement of the inner shaft relative to the outer shaft from the partially retracted position towards a fully retracted position moves the blocking member of the outer shaft into the distal aperture of the inner shaft to move the at least one protrusion of the actuation device from the distal aperture of the inner shaft to disengage the actuation device from the inner shaft. Upon disengagement of the at least one protrusion from the distal aperture, the actuation device is movable proximally independently of the inner shaft to a position in which the at least one protrusion of the actuation device is received in the proximal aperture of the inner shaft to resecure the actuation device to the inner shaft in a second position.

In some embodiments, the at least one protrusion is supported on a resilient arm of the actuation device.

In certain embodiments, the inner shaft further includes at least one groove that communicates with the distal aperture.

In embodiments, the at least one groove is configured to receive the at least one blocking member of the housing when the inner shaft is moved proximally in relation to the outer shaft from the partially retracted position to the fully retracted position of the inner shaft.

In some embodiments, a stripper plate is supported adjacent the support mechanism within the outer shaft in the partially retracted position of the inner shaft and the stripper plate is moved to a deployed position in response to movement of the inner shaft to a fully extended position.

In embodiments, the blocking member is positioned on an interior wall of the outer shaft.

In some embodiments, the proximal and distal apertures are further defined by a pair of proximal apertures and a pair of distal apertures, the at least one blocking member of the housing is further defined by a pair blocking members, and the at least one protrusion of the actuation device is further defined by a pair of protrusions.

In some embodiments, the outer shaft includes a housing portion and an outer shaft portion.

In another aspect of the present disclosure, the specimen retrieval device includes an outer shaft defining a longitudinal bore and having an inwardly extending blocking member, an inner shaft disposed within the longitudinal bore of the outer shaft and including proximal and distal apertures defined along the inner shaft, a support mechanism secured to a distal end of the inner shaft configured to releasably support a pouch of the specimen retrieval device, and an actuation device including at least one protrusion extending towards the inner shaft. The at least one protrusion is configured to be received within one of the proximal and distal apertures to releasably secure the actuation device to the inner shaft in two different positions. The at least one blocking member is aligned with the distal aperture of the inner shaft such that when the at least one protrusion is received within the distal aperture, proximal movement of the inner shaft in relation to the outer shaft moves the at least one blocking member into engagement with the at least one protrusion to cam the at least one protrusion of the actuation device from within the distal aperture of the inner shaft to disengage the actuation device from the inner shaft. Subsequent proximal movement of the actuation device relative to the inner and outer shafts causes the at least one protrusion to move into the proximal aperture of the inner shaft to resecure the actuation device to the inner shaft at a position further proximally of the housing.

In some embodiments, the at least one protrusion is supported on a resilient arm of the actuation device.

In embodiments, the inner shaft further includes at least one groove that communicates with the distal aperture. The at least one groove is configured to receive the at least one blocking member of the outer shaft when the inner shaft is moved distally in relation to the outer shaft.

In some embodiments, a stripper plate is supported adjacent a distal end of the inner shaft within the outer shaft.

In certain embodiments, the blocking member is positioned on an interior wall defining the longitudinal bore of the outer shaft.

In some embodiments, the at least one proximal and distal apertures are further defined by a pair of proximal apertures and a pair of distal apertures, the at least one blocking member of the housing is further defined by a pair blocking members, and the at least one protrusion of the actuation device is further defined by a pair of protrusions.

In yet another aspect of the present disclosure, a specimen retrieval device includes a housing, an outer shaft extending distally from the housing and defining a longitudinal bore, an inner shaft disposed within the longitudinal bore of the outer shaft, a support mechanism secured to a distal end of the inner shaft, a pouch releasably supported on the support mechanism and defining an opening, and an actuation device releasably coupled to a proximal end of the inner shaft. The actuation device includes a pivotal release mechanism having a mechanical interface configured to selectively engage a corresponding mechanical interface positioned on the inner shaft to releasably secure the actuation device to the inner shaft in a locked configuration. The release mechanism is movable from the locked configuration wherein the actuation device is operable to move the inner shaft in relation to the outer shaft to an unlocked configuration wherein the actuation device is separated from the inner shaft. A cinch has a proximal end secured to the actuation device and a distal end extending about the opening in the pouch. In the unlocked configuration, the actuation device is movable in relation to the inner shaft to retract the cinch to close the opening of the pouch.

In embodiments, the mechanical interface on the release mechanism is in the form of a detent and the mechanical interface on the inner shaft is in the form of an indent.

In some embodiments, the release mechanism is disposed on a top surface of the actuation device and is depressible to disengage the at least one mechanical interface of the release mechanism from the at least one mechanical interface on the inner shaft.

In certain embodiments, the release mechanism is overmolded to the actuation device.

In some embodiments, the release mechanism is pivotally coupled to the actuation device via a living hinge.

In embodiments, the cinch is operably coupled to a distal end of the actuation device.

In certain embodiments, the release mechanism is biased towards the locked configuration.

In yet another aspect of the present disclosure, a specimen retrieval device includes a housing, an outer shaft connected to and extending distally from the housing and defining a longitudinal bore and a longitudinal axis, an inner shaft movably disposed within the longitudinal bore of the outer shaft, a support mechanism supported on a distal end of the inner shaft, a pouch supported by the support mechanism adjacent a distal end of the inner shaft, and an actuation device releasably coupled to the inner shaft. The actuation device includes a release mechanism pivotally coupled thereto. The release mechanism includes at least one mechanical interface configured to selectively engage a corresponding mechanical interface positioned on the inner shaft to secure the actuation device to the inner shaft. The release mechanism is pivotal from a locked configuration wherein the actuation device is secured to the inner shaft and movement of the actuation device effects corresponding movement of the inner shaft to an unlocked configuration. A cinch has a proximal end secured to the actuation device and a distal end extending about an opening in the pouch. In the unlocked configuration of the release mechanism, the actuation device is separable from the inner shaft to allow movement of the actuation device in relation to the inner shaft to cinch the opening of the pouch.

In some embodiments, the mechanical interface on the release mechanism is in the form of a detent and the mechanical interface on the inner shaft is in the form of an indent.

In some embodiments, the release mechanism is disposed on a top surface of the actuation device and is depressible to disengage the at least one mechanical interface of the release mechanism from the at least one mechanical interface on the inner shaft.

In embodiments, the release mechanism is overmolded to the actuation device.

In some embodiments, the release mechanism is pivotally coupled to the actuation device via a living hinge.

In certain embodiments, the cinch is operably coupled to the distal end of the actuation device.

In another aspect of the present disclosure, a specimen retrieval device includes a housing, an outer shaft extending distally from the housing and defining a longitudinal bore, and an inner shaft movably disposed within the longitudinal bore of the outer shaft and including a handle. The inner shaft is movable between a fully retracted position and a fully extended position in which the handle is positioned adjacent the housing. A pouch is releasably supported at a distal end of the inner shaft. A lock-out device is supported on the housing and is movable from a locked position to an unlocked position. In the locked position, the lock-out device is positioned to prevent movement of the inner shaft to the fully extended position and in the unlocked position, the lock-out device is positioned to allow movement of the inner shaft to the fully extended position.

In some embodiments, the lock-out device is pivotally coupled to the housing via a pivot pin.

In embodiments, the lock-out device has a generally elongated configuration with a trailing end that is configured to engage a distal end of the handle of the inner shaft.

In certain embodiments, the lock-out device is seated within a notch defined within the housing.

In some embodiments, the notch is defined by at least one wall that is configured to contact at least a portion of the lock-out device and retain the lock-out device in the locked configuration.

In yet another aspect of the present disclosure, a specimen retrieval device includes a housing, an outer shaft connected to and extending distally from the housing and defining a longitudinal bore, an inner shaft movably disposed within the longitudinal bore of the outer shaft, a support mechanism supported on a distal end of the inner shaft, a pouch supported by the support mechanism, an actuation device operably coupled to a proximal end of the inner shaft, and a lock-out device pivotally supported on the housing. The lock-out device is movable from a locked configuration to prevent engagement between a proximal end of the housing and the actuation device to an unlocked configuration to allow engagement between the proximal end of the housing and the actuation device.

In embodiments, the lock-out device is pivotally coupled to the housing via a pivot pin.

In some embodiments, the lock-out device has a generally elongated configuration with a trailing end that is configured to engage a distal end of the actuation device.

In certain embodiments, the lock-out device is seated within a notch defined in the housing. The notch may be defined by at least one wall that is configured to contact at least a portion of the lock-out device and retain the lock-out device in the locked configuration.

In another aspect of the present disclosure, a specimen retrieval device includes a housing, an outer shaft extending distally from the housing and defining a longitudinal bore, an inner shaft movably disposed within the longitudinal bore of the outer shaft, a support mechanism secured to a distal end of the inner shaft, a specimen pouch supported by the support mechanism, first and second interfaces spaced longitudinally on the inner shaft, and a cam lock pivotally coupled to the housing and moveable from a first position, wherein the cam lock is positioned to engage the first interface of the inner shaft to prevent distal translation of the inner shaft relative to the housing to an extended position, to a second position wherein the cam lock is positioned to allow distal translation of the inner shaft relative to the housing to the extended position to facilitate deployment of the specimen pouch and wherein proximal translation of the inner shaft within the outer shaft from a partially retracted position to a fully retracted position causes the second interface of the inner shaft to engage and move the cam lock to the second position.

In some embodiments, the cam lock is rotatable from the first position to the second position about a pivot member coupled to the housing.

In embodiments, the cam lock defines a pivot hole and the pivot member is received within the pivot hole to pivotally couple the cam lock to the housing. At least one of the pivot hole and the pivot member is shaped such that rotation of the cam lock relative to the pivot causes the pivot to frictionally engage the cam lock to lock the cam lock in the second position.

In embodiments, the cam lock includes first and second portions, wherein in the first position of the cam lock, the first portion is positioned to cooperate with the first interface of the inner shaft to prevent distal translation of the inner shaft relative to the housing to the extended position and is positioned to cooperate with the second interface to rotate the cam lock to the second position upon proximal translation of the inner shaft from the partially retracted position to the fully refracted position to allow subsequent distal translation of the inner shaft relative to the housing.

In some embodiments, the second portion of the cam lock is positioned and configured to lock the cam lock in the second position.

In certain embodiments, the second portion of the cam lock is positioned offset relative to the first plane and is configured to engage a side of the inner shaft to prevent rotation of the cam lock from the first position in a direction away from the second position to prevent distal translation of the inner shaft.

In embodiments, the first portion of the cam lock has dimensions different from the second portion of the cam lock.

In yet another aspect of the present disclosure, a specimen retrieval device includes a housing, an outer shaft connected to and extending distally from the housing and defining a longitudinal bore extending therethrough, an inner shaft movably disposed within the longitudinal bore of the outer shaft and translatable therethrough, a support mechanism configured to releasably support a specimen pouch at a distal end of the inner shaft, a first interface disposed on the inner shaft, and a cam lock pivotally coupled to the housing and moveable from a first position wherein the cam lock prevents distal translation of the inner shaft relative to the housing to a second position wherein the cam lock allows distal translation of the inner shaft relative to the housing to facilitate deployment of the specimen pouch. The cam lock includes first and second portions. The first portion cooperates with the first interface to rotate the cam lock to the second position upon proximal translation of the inner shaft to allow subsequent distal translation of the inner shaft relative to the housing and the second portion of the cam lock cooperates with a side of the inner shaft to prevent initial distal translation of the inner shaft relative to the housing when the cam lock is disposed in the first position.

In some embodiments, a second interface is disposed on the inner shaft proximally of the first interface. The first portion of the cam lock cooperates with the second interface to prevent distal translation of the inner shaft when the cam lock is in the first position.

In embodiments, the first portion of the cam lock is disposed within a first plane and is configured to cooperate with the first and second interfaces positioned on a top of the inner shaft and the second portion is offset relative to the first plane and is configured to cooperate with a side of the inner shaft.

In another aspect of the disclosure, a specimen retrieval device includes a housing, an outer shaft extending distally from the housing and defining a longitudinal bore, an inner shaft movably disposed within the longitudinal bore of the outer shaft and defining a channel, a support mechanism supported on a distal end of the inner shaft, a specimen pouch supported at a distal end of the inner shaft, first and second interfaces disposed at respective proximal and distal ends of the channel of the inner shaft, and a cam lock pivotally coupled to the housing and moveable from a first position wherein the cam lock is positioned to prevent distal translation of the inner shaft relative to the housing to a second position wherein the cam lock is positioned to allow distal translation of the inner shaft relative to the housing to facilitate deployment of the specimen pouch. The cam lock includes first and second portions. The first portion extends into the channel and cooperates with the first interface to prevent initial distal translation of the inner shaft relative to the housing when the cam lock is disposed in the first position. The first portion also cooperates with the second interface to effect movement of the cam lock from the first position to the second position upon proximal translation of the inner shaft to allow distal translation of the inner shaft relative to the housing. A spring is coupled to the housing and cooperates with the second portion of the cam lock to retain the cam lock in the second position upon full proximal translation of the inner shaft relative to the housing.

In some embodiments, the second portion of the cam lock rotates against the bias of the spring as the cam lock moves from the first position to the second position. The second portion of the cam lock includes a distal end configured to lock against the spring once the cam lock is rotated to the second position.

In yet another aspect of the present disclosure, a method of preventing inadvertent deployment of a specimen pouch of a specimen retrieval device includes positioning a cam lock on a housing of the specimen retrieval device; movably positioning an inner shaft of the specimen retrieval device to move through the housing; positioning a pivotal cam lock on the housing; positioning a proximal interface on the inner shaft in a first position to prevent distal movement of the inner shaft in relation to the housing; positioning a distal interface on the inner shaft in a position to engage the cam lock when the inner shaft is moved proximally to effect movement of the cam lock from the first position to the second position, wherein in the second position of the cam lock, the cam lock allows for distal movement of the inner shaft; moving the inner shaft proximally to move the cam lock from the first position to the second position; and advancing the inner shaft distally in relation to the housing to deploy a specimen pouch from the specimen retrieval device.

In some embodiments, the method includes locking the cam lock in the second position.

In another aspect of the present disclosure, a specimen retrieval device includes a housing, an outer shaft connected to the housing and extending distally therefrom, the outer shaft defining a longitudinal bore, an inner shaft disposed within the longitudinal bore of the outer shaft and translatable therethrough, a support mechanism secured to a distal end of the inner shaft, a specimen pouch supported on the support mechanism at a distal end of the inner shaft, first and second interfaces disposed at respective proximal and distal ends of the inner shaft, and a cam lock pivotably coupled to the housing and rotatable from a first position wherein the cam lock prevents initial distal translation of the inner shaft relative to the housing to a second position wherein the cam lock allows distal translation of the inner shaft relative to the housing to facilitate deployment of the specimen pouch. The cam lock includes first and second portions extending therefrom. The first portion cooperates with the first interface to prevent initial distal translation of the inner shaft relative to the housing when the cam lock is disposed in the first position and the first portion cooperates with the second interface to effect rotation of the cam lock from the first position to the second position upon proximal translation of the inner shaft. A spring is coupled to the housing, wherein upon full proximal translation of the inner shaft within the outer shaft, a distal end of the second portion of the cam lock rotates against the bias of the spring and locks against the spring once the cam lock is rotated to the second position thereby locking the cam lock in the second position and allowing distal translation of the inner shaft relative to the outer shaft to facilitate deployment of the specimen pouch.

In yet another aspect of the disclosure, a specimen retrieval device includes a housing defining a slot, an outer shaft extending distally from the housing and defining a longitudinal bore, an inner shaft movably disposed within the longitudinal bore of the outer shaft and defining a channel and including a stop surface positioned proximally of the channel, a support mechanism secured to a distal end of the inner shaft, a specimen pouch supported on the support mechanism at a distal end of the inner shaft and a removable shipping wedge configured to be received through the slot in the housing. The removable shipping wedge includes an interface configured to slidably receive the inner shaft. The interface is configured to cooperate with the stop surface of the inner shaft to prevent full distal translation of the inner shaft in relation to the housing while allowing proximal translation of the inner shaft in relation to the housing. The inner shaft is movable proximally in relation to the housing to a fully retracted position to position the channel in alignment with the interface and facilitate removal of the removable shipping wedge from the specimen retrieval device through the slot in the housing to facilitate full distal translation of the inner shaft in relation to the housing and deployment of the specimen pouch.

In some embodiments, the inner shaft includes a flexible finger positioned proximally of the channel. The flexible finger extends outwardly from the inner shaft and is positioned to pass under the shipping wedge to a location proximal of the shipping wedge when the inner shaft is moved to the fully retracted position. The flexible finger is biased against the interface of the shipping wedge in the fully retracted position of the inner shaft to prevent distal movement of the inner shaft relative to the housing until the shipping wedge is removed from the specimen retrieval device.

In some embodiments, the interface includes opposing surfaces that define a notch that is shaped to slidably receive the inner shaft.

In embodiments, the specimen retrieval device includes a stripper plate disposed within the outer shaft that is selectively deployable with the specimen pouch. The inner shaft includes a proximal handle that is spaced from the housing a distance d when the shipping wedge is inserted within the groove of the housing. The distance d represents a dwell distance required to distally translate the inner shaft relative to the housing when the shipping wedge is removed to deploy the stripper plate from the outer shaft.

In another aspect of the present disclosure, a method of preventing inadvertent deployment of a specimen pouch of a specimen retrieval device includes providing a specimen retrieval device including a housing having a groove defined therein, an outer shaft connected to the housing and extending distally therefrom, the outer shaft defining a longitudinal bore extending therethrough, an inner shaft disposed within the longitudinal bore of the outer shaft and translatable therethrough from a fully retracted position to an extended position, the inner shaft defining a proximal stop surface, a support mechanism supported on a distal end of the inner shaft, a specimen pouch supported on the support mechanism at a distal end of the inner shaft, and a removable shipping wedge having an interface at a distal end thereof configured to receive an outer periphery of the inner shaft while allowing translation of the inner shaft therethrough; and inserting the shipping wedge through the groove in the housing such that the interface engages the stop surface of the inner shaft to prevent distal translation of the inner shaft relative to the housing to the extended position.

In another aspect of the present disclosure, a method of deploying of a specimen pouch of a specimen retrieval device includes providing a specimen retrieval device including a housing having a groove defined therein, an outer shaft connected to the housing and extending distally therefrom, the outer shaft defining a bore extending therethrough, an inner shaft disposed within the bore of the outer shaft and translatable therethrough, the inner shaft defining a slot, a support mechanism configured to releasably support a specimen pouch of the specimen retrieval device at a distal end thereof, a flexible finger disposed proximal to the slot on the inner shaft, a stop surface disposed at a proximal end of the inner shaft, and a removable shipping wedge including an interface at a distal end thereof configured to encompass the outer periphery of the inner shaft while allowing translation of the inner shaft therethrough; inserting the interface through the groove in the housing such that the interface engages the stop surface at the proximal end of the inner shaft to prevent initial distal translation of the inner shaft relative to the housing; proximally translating the inner shaft relative to the housing from a first position wherein the stop surface is engaged with the interface of the shipping wedge to prevent distal translation of the inner shaft to a second position wherein the interface of the shipping wedge is aligned with the slot of the inner shaft; removing the shipping wedge through the groove in the housing and the slot in the inner shaft; and distally translating the inner shaft relative to the housing to deploy the specimen pouch.

In some embodiments, the proximally translating step includes biasing the flexible finger against the interface of the shipping wedge and then releasing the flexible finger on a proximal side of the interface into engagement with the interface when the inner shaft is fully translated to the second position to prevent distal movement of the inner shaft until the shipping wedge is removed.

In another aspect of the present disclosure a specimen retrieval device includes a housing, an outer shaft extending distally from the housing and defining a longitudinal bore, and an inner shaft movably disposed within the longitudinal bore of the outer shaft. The inner shaft defines a cam slot along an outer periphery thereof including first and second portions and a channel connecting distal ends of the first and second portions. The second portion of the cam slot has a length greater than a length of the first portion. A support mechanism is secured to the distal end of the inner shaft and a specimen pouch is supported at a distal end of the inner shaft on the support mechanism. A torsion spring has a first end fixedly engaged with the housing and a second end slidably received within the cam slot and is in tension. The second end of the torsion spring is initially positioned at a proximal end of the first portion of the cam slot when the inner shaft is in a partially retracted position to prevent further distal translation of the inner shaft relative to the housing. The second end of the torsion spring is movable from the proximal end of the first portion of the cam slot to a distal end of the first portion of the cam slot upon retraction of the inner shaft from the partially retracted position to a fully retracted position, wherein when the second end of the torsion spring reaches the distal end of the first portion of the cam slot, the tension in the torsion spring causes the second end of the torsion spring to translate through the channel of the cam slot to the second portion of the cam slot. When the second end of the torsion spring is positioned in the second portion of the cam slot, the inner shaft may be distally translated along the second portion of the cam slot to an extended position relative to the housing to deploy the specimen pouch.

In some embodiments, a stripper plate is disposed within a distal end of the outer shaft proximally of the specimen pouch and is selectively deployable with the specimen pouch. The second portion of the cam slot has a length greater than the first portion of the cam slot by a distance "X" and wherein the distance "X" represents a dwell distance required to distally translate the inner shaft relative to the housing to deploy the stripper plate disposed within the outer shaft.

In embodiments, the inner shaft and the outer shaft are configured to prevent rotation of the inner shaft in relation to the outer shaft.

In certain embodiments, the distal end of the second portion of the cam slot is longitudinally aligned with the distal end of the first portion of the cam slot.

In some embodiments, a proximal end of the second portion of the cam slot extends further proximally than a proximal end of the first portion of the cam slot by a distance X, the distance X permitting the inner shaft to move to the extended position.

In yet another aspect of the present disclosure, a method of deploying a specimen pouch of a specimen retrieval device includes providing a specimen retrieval device including a housing, an outer shaft connected to the housing and extending distally therefrom, the outer shaft defining a bore extending therethrough, an inner shaft disposed within the bore of the outer shaft and translatable therethrough, the inner shaft including a support mechanism configured to releasably support a specimen pouch of the specimen retrieval device at a distal end thereof, the inner shaft including a cam slot defined in an outer periphery thereof, the cam slot including first and second portions and a channel defined therebetween; engaging a first end of a torsion spring to the housing and positioning a second end of the torsion spring to ride within the cam slot upon translation of the inner shaft with respect to housing, wherein the second end of the torsion spring is initially positioned at a proximal end of the first portion of the cam slot to prevent initial distal translation of the inner shaft relative to the housing; proximally translating the inner shaft with respect to the housing to move the second end of the torsion spring within the cam slot from a first position at the proximal end of the first portion of the cam slot to a second position at a distal end of the first portion of the cam slot to allow the second end of the torsion spring to transition under the bias of the torsion spring within the channel into the distal end of the second portion of the cam slot; and distally translating the inner shaft relative to the housing to deploy the specimen pouch.

In another aspect of the disclosure, a specimen retrieval device includes a housing, an outer shaft extending distally from the housing, the outer shaft defining a longitudinal bore, an inner shaft disposed within the longitudinal bore of the outer shaft and defining a cam slot that extends along a length of the inner shaft, the cam slot defining a proximal end and a distal end, and a removable shipping wedge. The removable shipping wedge includes a body having a flange extending from an upper surface thereof. The flange has a finger at a distal end thereof dimensioned to ride within the cam slot of the inner shaft. The finger is insertable into the cam slot through the notch. At least one support extends from the body and is configured to engage the housing. The finger of the shipping wedge is configured to be received within the proximal end of the cam slot to prevent distal translation of the inner shaft relative to the housing when the inner shaft is in a partially retracted position.

In some embodiments, the inner shaft supports a support mechanism which is configured to releasably support a specimen pouch of the specimen retrieval device at a distal end of the inner shaft. The inner shaft is moveable from a first position wherein the finger and the proximal end of the cam slot cooperate to prevent distal translation of the inner shaft relative to the housing to a second position at the distal end of the cam slot, wherein the orientation of the finger within the cam slot allows removal of the shipping wedge and subsequent distal translation of the inner shaft relative to the housing to facilitate deployment of the specimen pouch.

In some embodiments, the at least one support includes a pair of lateral supports extending from opposing ends of the body.

In embodiments, the distal end of the cam slot defines a notch configured to allow removal of the shipping wedge from the inner shaft and the housing.

In certain embodiments, the shipping wedge further includes a removal tab configured to be gripped to facilitate removal of the shipping wedge from the inner shaft and the housing.

In some embodiments, the distal end of the cam slot includes a ramp-like surface positioned proximally of the notch.

In embodiments, engagement of the finger and the ramp-like surface provides tactile feedback to a clinician during distal translation of the inner shaft relative to the housing.

In some embodiments, the bias of the finger against the ramp-like surface causes the finger to snap into the notch to provide the tactile feedback.

In certain embodiments, a disposition of the finger within the notch prevents the inner shaft from being translated distally relative to the housing until the shipping wedge is removed.

In embodiments, the housing includes finger rings extending from opposing sides of the body and each of the one or more supports is configured to engage a respective one of the finger rings to brace the shipping wedge against the housing.

In yet another aspect of the present disclosure, a specimen retrieval device includes a housing, an outer shaft connected to and extending distally from the housing and defining a bore extending therethrough, and an inner shaft movably disposed within the bore of the outer shaft and translatable therethrough. The inner shaft includes a cam slot having proximal and distal ends and supports a support mechanism configured to releasably support a specimen pouch at the distal end thereof. A removable shipping wedge includes a body having a flange extending from an upper surface thereof. The flange has a finger dimensioned to ride within the cam slot. The inner shaft is moveable from a first position wherein the finger and the proximal end of the cam slot cooperate to prevent distal translation of the inner shaft relative to the housing to a second position at the distal end of the cam slot wherein the orientation of the finger within the cam slot allows removal of the shipping wedge from the specimen retrieval device and subsequent distal translation of the inner shaft relative to the housing.

In embodiments, the shipping wedge further includes a removal tab configured to facilitate removal of the shipping wedge from the inner shaft and the housing.

In some embodiments, the distal end of the cam slot includes a transverse notch that facilitates removal of the shipping wedge from the inner shaft and the housing.

In certain embodiments, the distal end of the cam slot includes a ramp-like surface which is configured to bias the finger as the finger is translated therethrough.

In some embodiments, the bias of the finger against the ramp-like surface provides tactile feedback to the clinician during distal translation of the inner shaft relative to the housing.

In embodiments, the bias of the finger against the ramp-like surface causes the finger to snap into the notch.

In some embodiments, the finger when positioned within the notch prevents the inner shaft from being translated distally relative to the housing until the shipping wedge is removed.

In yet another aspect of the present disclosure, a method of preventing inadvertent deployment of a specimen pouch of a specimen retrieval device includes providing a specimen retrieval device including a housing, an outer shaft connected to the housing and extending distally therefrom, the outer shaft defining a bore extending therethrough, an inner shaft disposed within the bore of the outer shaft and translatable therethrough, the inner shaft including a cam slot defined therein that extends therealong, the cam slot including proximal and distal ends, and a removable shipping wedge including a body having a flange extending from an upper surface thereof having a finger at a distal end thereof dimensioned to ride within the cam slot, and at least one support extending from the body and configured to engage the housing; and engaging the removable shipping wedge to the housing and the inner shaft such that the finger of the flange is disposed in abutting relation with the proximal end of the cam slot preventing initial distal translation of the inner shaft relative to the housing.

In another aspect of the present disclosure, a method of deploying a specimen pouch of a specimen retrieval device includes providing a specimen retrieval device including a housing, an outer shaft connected to the housing and extending distally therefrom, the outer shaft defining a bore extending therethrough, an inner shaft disposed within the bore of the outer shaft and translatable therethrough, the inner shaft including a support mechanism configured to releasably support a specimen pouch of the specimen retrieval device at the distal end thereof, the inner shaft including a cam slot defined therein that extends therealong, the cam slot including a proximal end and a distal end having a notch defined therein, and a removable shipping wedge including a body having a flange extending from an upper surface thereof having a finger at a distal end thereof dimensioned to ride within the cam slot, and at least one support extending from the body and configured to engage the housing; engaging the removable shipping wedge to the housing and the inner shaft such that the finger of the spring-like flange is disposed in abutting relation with the proximal end of the cam slot preventing initial distal translation of the inner shaft relative to the housing; retracting the inner shaft relative to the housing such that the finger of the spring-like flanges rides along the cam slot and bottoms out in the notch at a distal end thereof; removing the shipping wedge from the housing and the inner shaft; and distally translating the inner shaft with respect the housing to deploy the specimen pouch.

In yet another aspect of the present disclosure, a stripper plate is disclosed for use with a specimen retrieval device having an elongated hollow outer shaft defining an inner diameter. The stripper plate includes a leading end including major and minor axes. A width of the major axis is greater than the inner diameter of the outer shaft and a width of the minor axis is smaller than the inner diameter of the outer shaft. The leading end includes first and second apertures defined therein and extending therethrough to a trailing end. The first aperture is configured to receive a support mechanism of the specimen retrieval device and the second aperture is configured to receive a suture. The stripper plate is deployable from a retracted configuration within an inner periphery of the outer shaft to a deployed configuration outside the outer shaft, wherein, when the stripper plate is in the deployed configuration, the leading end of the stripper plate is configured to uncouple a specimen pouch from the support mechanism.

In some embodiments, the stripper plate is oriented at a first angle relative to a longitudinal axis defined through the elongated hollow outer shaft when in the retracted configuration and wherein the stripper plate is oriented at a second angle relative to a longitudinal axis when disposed in the deployed configuration.

In embodiments, the leading end of the stripper plate includes two second apertures, each second aperture being configured to receive a respective portion of the suture.

In certain embodiments, the stripper plate defines a beveled peripheral wall that extends between the leading end and trailing end.

In some embodiments, the bevel of the peripheral wall defines an angle with the leading end that facilitates proper orientation of the stripper plate at the first angle within the inner periphery of the outer shaft.

In embodiments, the angle of the bevel of the peripheral wall is in the range of 25 degrees to 45 degrees.

In some embodiments, the first angle of the stripper plate ranges from 1 degree to 75 degrees.

In certain embodiments, the second angle of the stripper plate ranges from 76 degrees to 90 degrees.

In embodiments, the leading end of the stripper plate includes a chamfered front edge to facilitate deployment of the stripper plate from the outer shaft.

In some embodiments, the first aperture includes a circular configuration. Alternately, the first aperture includes a rectilinear configuration.

In certain embodiments, when the stripper plate is deployed and the stripper plate is forced proximally, the width of the major axis prevents the stripper plate from re-entering the inner periphery of the outer shaft.

In yet another aspect of the present disclosure, a stripper plate is described for use with a specimen retrieval device having an elongated hollow outer shaft defining an inner diameter. The stripper plate includes a leading end including major and minor axes. A width of the major axis is greater than the inner diameter of the outer shaft and a width of the minor axis is smaller than the inner diameter of the outer shaft. The leading end includes first and second apertures defined therein and extending therethrough to a trailing end. The first aperture is configured to receive a support mechanism of the specimen retrieval device and the second aperture is configured to receive a suture. The stripper plate has a peripheral wall defined between the leading end and the trailing end that is beveled to facilitate deployment of the stripper plate from a refracted configuration within an inner periphery of the outer shaft to a deployed configuration outside the outer shaft.

In some embodiments, the leading end of the stripper plate is configured to uncouple a specimen pouch from the support mechanism.

In embodiments, the leading end includes a top portion and a bottom portion and wherein the bevel of the peripheral wall extends from both the top and bottom portions of the leading end at the same angle towards the trailing end.

In certain embodiments, the trailing end includes a bump-out extending outwardly therefrom and surrounding the first aperture. The bump-out faces proximally when the stripper plate is disposed in the retracted configuration. The bump-out is configured to engage the inner periphery of the outer shaft to center the stripper plate therein.

In some embodiments, the bump-out includes a semi-circular configuration.

In embodiments, the width of the major axis of the stripper plate prevents the stripper plate from re-entering the inner periphery of the outer shaft.

In yet another aspect of the present disclosure, a stripper plate is described for use with a specimen retrieval device having an elongated hollow outer shaft defining an inner diameter, the stripper plate. The stripper plate includes an elongated cylindrical portion defined by opposing end portions and has a length L. The cylindrical portion includes an aperture defined therethrough configured to receive a suture and a relief defined along at least a portion of an outer peripheral surface thereof proximate the aperture. The relief is configured to facilitate passage of the suture through the aperture. The stripper plate is deployable from a retracted configuration within an inner periphery of the outer shaft to a deployed configuration outside the outer shaft. The length L is greater than the inner diameter of the outer shaft such that once the stripper plate is deployed from the retracted configuration the stripper plate is prevented from reentering the inner periphery.

In some embodiments, the stripper plate is configured such that, the opposing end portions contact either side of the outer shaft to facilitate uncoupling of a specimen pouch from a pouch support mechanism.

In embodiments, the outer end portions include a first diameter and the elongated cylindrical portion includes a middle portion having a second diameter that is greater than the first diameter.

In some embodiments, the middle portion includes the aperture defined therethrough.

In certain embodiments, the elongated cylindrical portion is tapered from the middle portion to the outer end portions.

In some embodiments, at least one of the outer end portions includes a recess defined therein configured to engage an inner peripheral edge of the outer shaft to facilitate uncoupling a specimen pouch from a pouch support mechanism.

In embodiments, each of the outer end portions includes a recess defined therein. Each respective recess is configured to engage opposing portions of the inner peripheral edge of the outer shaft.

In yet another aspect of the present disclosure, a stripper plate is described for use with a specimen retrieval device having an elongated hollow outer shaft defining an inner diameter. The stripper plate includes an elongated cylindrical portion defined by leading and trailing ends. The elongated cylindrical portion includes an aperture defined therethrough configured to receive a support mechanism of the specimen retrieval device. The stripper plate is deployable from a retracted configuration within an inner periphery of the outer shaft to a deployed configuration outside the outer shaft. The trailing end includes at least one elongated slit defined therein and extending at least partially toward the leading end. The at least one elongated slit is configured to allow the stripper plate to flex inwardly to facilitate insertion of the stripper plate into the inner periphery of the outer shaft. At least one tab-like living hinge is disposed on an outer peripheral surface of the elongated cylindrical portion. The at least one living hinge is biased to self-deploy and extend outwardly from the outer peripheral surface of the elongated cylindrical portion once the stripper plate is deployed.

In some embodiments, the at least one elongated slit includes a plurality of elongated slits.

In embodiments, the plurality of tab-like living hinges is interposed between the plurality of elongated slits.

In some embodiments, the leading end of the stripper plate faces proximally within the inner periphery of the outer shaft when disposed in the refracted configuration.

In certain embodiments, the stripper plate is positioned in a compressed condition against the bias of the plurality of slits within the inner periphery of the outer shaft.

In embodiments, the plurality of tab-like living hinges disposed along the outer peripheral surface of the elongated cylindrical portion is configured to self-deploy from a flush configuration with respect to the outer peripheral surface of the elongated cylindrical portion when the stripper plate is disposed in the refracted configuration within the inner periphery of the outer shaft to an extended configuration relative to the outer peripheral surface of the elongated cylindrical portion when the stripper plate is externalized to the deployed configuration.

In some embodiments, when the stripper plate is deployed and the stripper plate is forced proximally, the tab-like living hinges are configured to contact an inner peripheral edge of the outer shaft to facilitate uncoupling of a specimen pouch from a pouch support mechanism.

In certain embodiments, when the stripper plate is deployed and the stripper plate is forced proximally, the tab-like living hinges prevent the stripper plate from re-entering the inner periphery of the outer shaft.

BRIEF DESCRIPTION OF THE DRAWINGS

Embodiments of the presently disclosed specimen retrieval device are described hereinbelow with reference to the drawings wherein:

FIG. 14 is an enlarged perspective view of a proximal end of the specimen retrieval device shown in FIG. 12A illustrating the inner shaft and actuation device with the actuation device engaged with the distal apertures of the inner;

FIG. 15 is an enlarged perspective view of the proximal end of the specimen retrieval device shown in FIG. 12A with the outer shaft shown partially in cross-section;

FIG. 16 is a cross-sectional view of the proximal end of the specimen retrieval device shown in FIG. 12A with the inner shaft shown in a partially retracted configuration and the actuation device received in the distal apertures of the inner shaft;

FIG. 16A is a cross-sectional view of the proximal end of the specimen retrieval device shown in FIG. 12A as the inner shaft is moved from the partially retracted position towards the fully retracted position as the detents on the outer shaft engage the protrusions on the arms of the actuation device;

FIG. 16B is a cross-sectional view of the proximal end of the specimen retrieval device shown in FIG. 12A as the inner shaft is moved from the partially retracted position towards the fully retracted position after the detents on the outer shaft have urged the protrusions on the arms of the actuation device from the distal apertures;

FIG. 17 is a cross-sectional view of the proximal end of the specimen retrieval device shown in FIG. 12A with the inner shaft in the fully retracted position with the protrusions on the arms of the actuation device received in the proximal apertures of the inner shaft;

FIG. 19 is a schematic view of a specimen retrieval device according to another embodiment of the present disclosure with parts separated;

FIG. 20 is a cross-sectional view taken along line segment 20-20 in FIG. 19 with an actuation device and inner shaft of the specimen retrieval device shown in a locked configuration for moving the inner shaft in relation to an outer shaft of the specimen retrieval device;

FIG. 21 a cross-sectional view of the actuation device and inner shaft with the actuation device shown in an un-locked configuration for cinching a pouch of the specimen retrieval device shown in FIG. 19;

FIG. 23A is a schematic view of a specimen retrieval device according to another embodiment of the present disclosure having an inner shaft, a housing and a cam lock configured to prevent inadvertent initial distal advancement of the inner shaft relative to the housing;

FIG. 23B is an enlarged view of a cam lock of FIG. 23A;

FIG. 23C is a greatly-enlarged view of another embodiment of the present disclosure showing the engagement of a pivot disposed on the housing to an inner periphery of a pivot hole defined in the cam lock when the cam lock is moved from a first position to a second position;

FIG. 25A is an exploded perspective view of a specimen retrieval device according to another embodiment of the present disclosure;

FIG. 25B is a side perspective view of a removable shipping wedge usable with the specimen retrieval device of FIG. 25A;

DETAILED DESCRIPTION OF THE EMBODIMENTS

Figure 1:
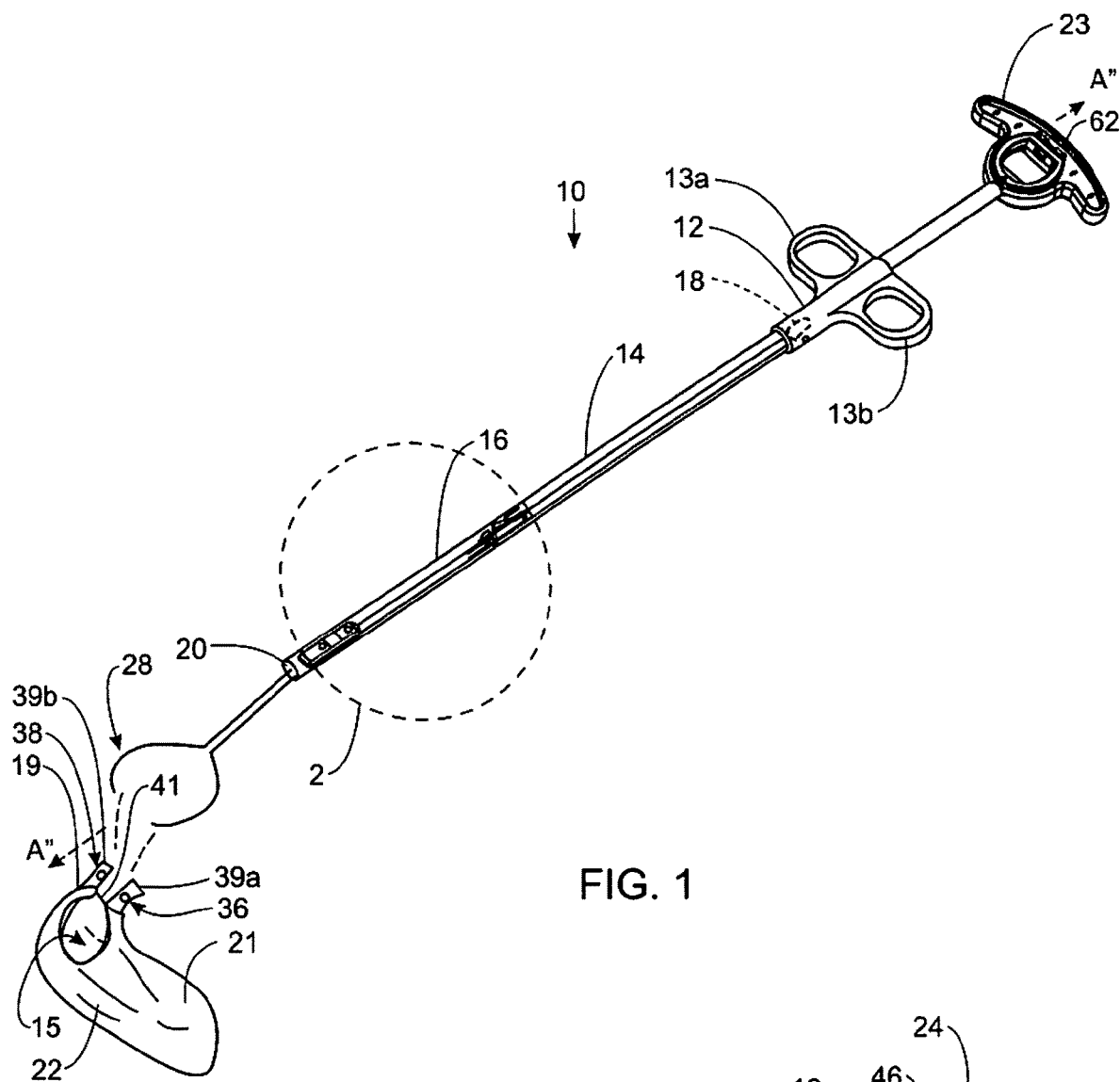
FIG. 1 is a perspective view of a specimen retrieval device in accordance with an embodiment of the present disclosure.

Embodiments of the present disclosure will now be described in detail with reference to the drawings in which like reference numerals designate identical or corresponding elements in each of the several views. As used herein, the term distal refers to that portion of the instrument which is farthest from the clinician, while the term proximal refers to that portion of the instrument which is closest to the clinician. In the following description, well-known functions or constructions are not described in detail to avoid obscuring the present disclosure in unnecessary detail.

As used herein with reference to the present disclosure, the terms laparoscopic and endoscopic are interchangeable and refer to instruments having a relatively narrow operating portion for insertion into a cannula or small incision in the skin. Laparoscopic and endoscopic also refer to minimally invasive surgical procedures. It is believed that the present disclosure may find use in any procedure where access to the interior of the body is limited to a relatively small incision, with or without the use of a cannula as in minimally invasive procedures. In addition, as used herein, the term clinician refers to medical staff including doctors, nurses and support personnel.

With reference to FIGS. 1-6, and initially with reference to FIG. 1, a specimen retrieval device 10 according to an embodiment of the present disclosure is illustrated. Specimen retrieval device 10 includes a housing 12, an outer shaft 14 and an inner shaft 16. Specimen retrieval device 10 (and components associated therewith) may be formed from any suitable biocompatible material, e.g., plastic. In an embodiment, an injection molding manufacturing process may be utilized to form housing 12, outer shaft 14 and inner shaft 16.

Housing 12 and outer shaft 14 define a longitudinal bore and have a generally elongated configuration. The longitudinal bore is configured to slidably receive the inner shaft 16. The housing 12 may be formed as a unitary component or as two separate half components that are coupled to one another by one or more suitable coupling methods (e.g., one or more suitable adhesives). In the latter instance, an indent/detent configuration (not explicitly shown) may be utilized to facilitate coupling the two separate half components. Housing 12 includes a handle, e.g., a pair of opposing lateral loops 13a, 13b (FIG. 1), that allow a clinician to grasp and manipulate the specimen retrieval device 10. Alternately, other handle configurations are envisioned.

One or more stop members, e.g., a boss (or recess) 18 (shown in phantom in FIGS. 1 and 3-5), is defined along an interior wall of the housing 12 and is configured to releasably engage the inner shaft 16 to limit distal translation of the inner shaft 16 in relation to the outer shaft 14 as will be discussed in further detail below. Other devices and/or components (e.g., a detent, protrusion, or the like) may be utilized in place of the boss 18 to engage the inner shaft 16.

The outer shaft 14 extends distally from housing 12 and includes a generally tubular configuration, which as discussed above, defines the longitudinal bore. The outer shaft 14 is configured to slidably receive the inner shaft 16 and defines a longitudinal axis "A-A" therethrough. Outer shaft 14 is dimensioned for insertion through a trocar, cannula or natural body orifice for endoscopic or laparoscopic procedures. An aperture 20 of suitable configuration is provided at a distal end of the outer shaft 14 and is dimensioned and configured to allow ingress and egress of the inner shaft 16 including a pouch 22 (FIG. 1). The outer shaft 14 is coupled to housing 12 via one or more suitable coupling methods (e.g., welding, etc. adhesives). Alternately, the outer shaft 14, may be monolithically formed with housing 12.

Figure 2:
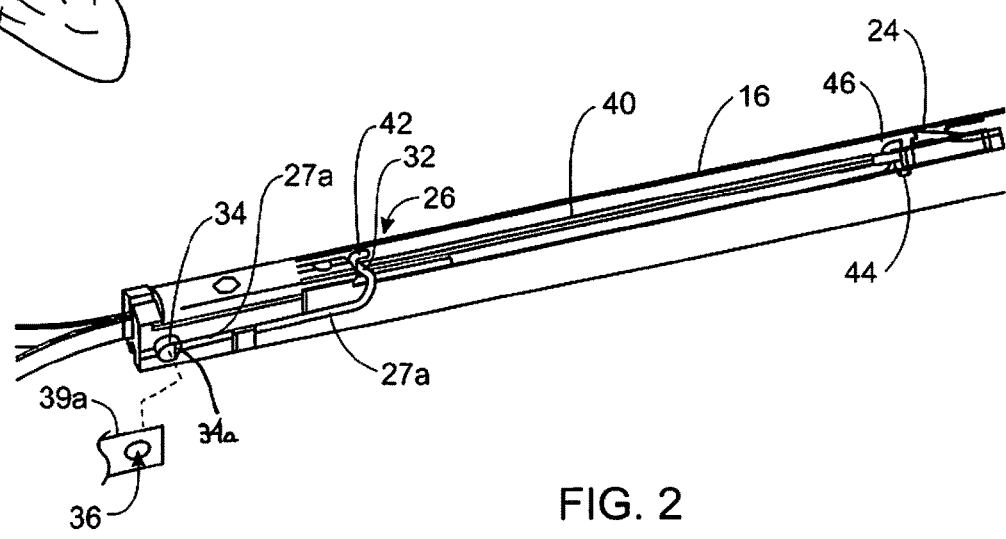
FIG. 2 is the indicated area of detail shown in FIG. 1.
Figure 3:
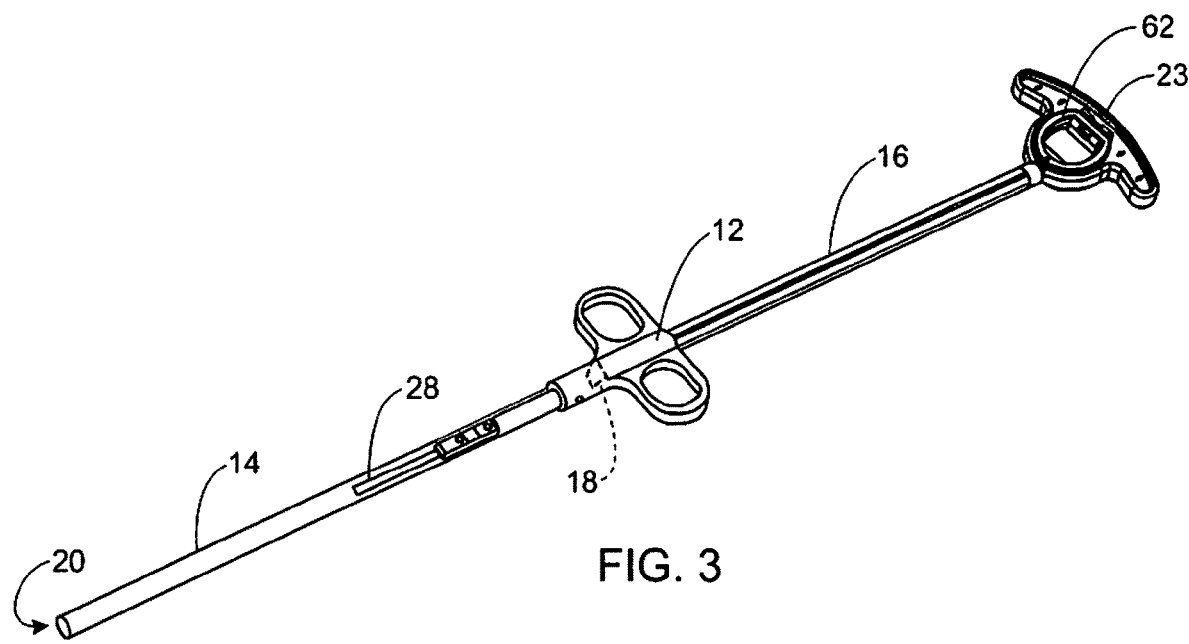
FIG. 3 is a perspective view of the specimen retrieval device shown in FIG. 1 with an inner shaft of the specimen retrieval device shown in a fully retracted configuration.
Figure 4:
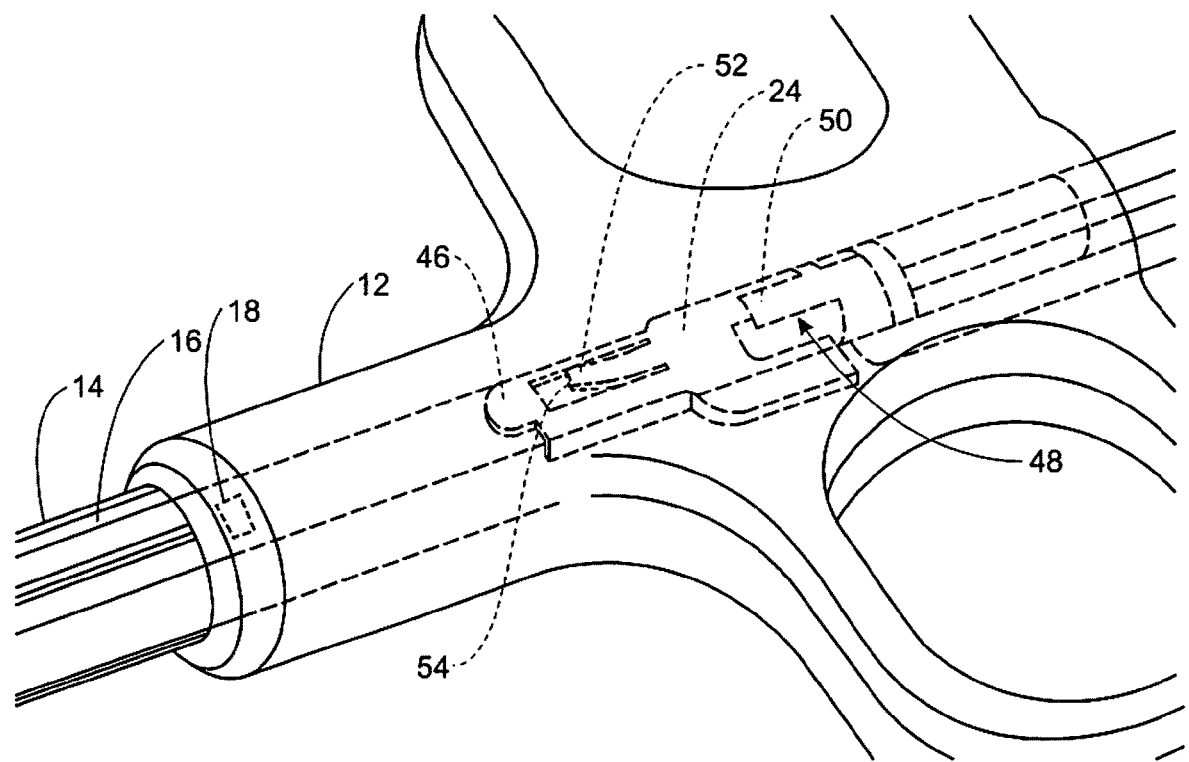
FIG. 4 is an enlarged partial perspective view of a housing of the specimen retrieval device shown in FIG. 1 with a sled of the inner shaft and a stop member of the housing shown in phantom to illustrate a position of the sled in relation to the stop member when the inner shaft is in the fully retracted configuration.

Continuing with reference to FIGS. 1-6, the inner shaft 16 has a generally elongated configuration and is movably positioned within the outer shaft 14. The inner shaft 16 is translatable within the outer shaft 14 to move the pouch 22 from a fully retracted configuration to an extended or deployed configuration. In the fully retracted configuration, the pouch 22 is disposed at least partially within a distal end of the outer shaft 14 for positioning the specimen retrieval device 10 through an access port (FIGS. 3 and 4 show the inner shaft 16 in a fully retracted configuration; the pouch 22 is not shown in FIG. 3 for clarity). In the extended or deployed configuration, the pouch 22 is disposed outside of the outer shaft 14 for positioning target tissue within pouch 22.

Figure 6:
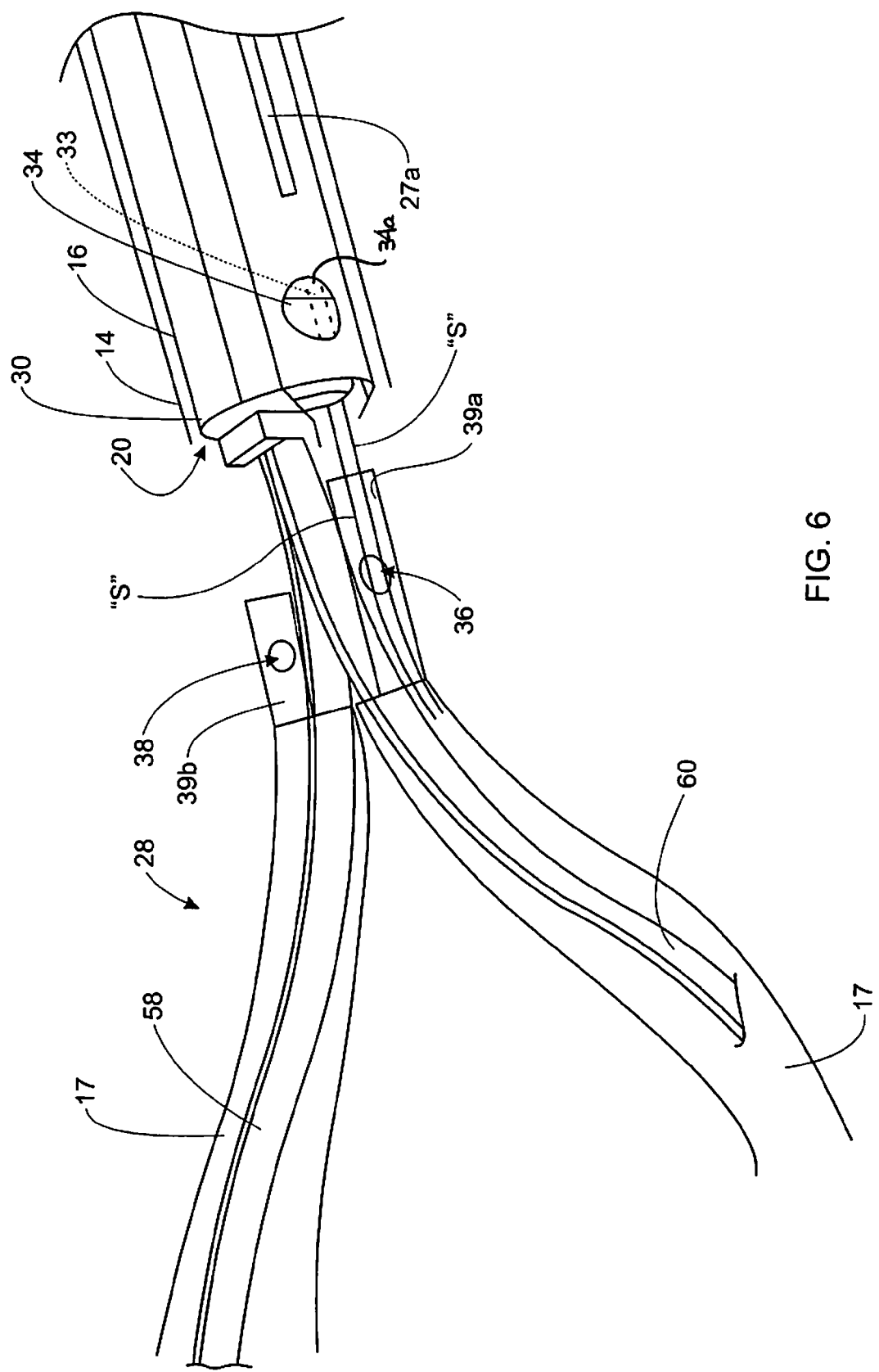
FIG. 6 is an enlarged partial perspective view of a distal end of the specimen retrieval device with a support mechanism of the inner shaft in a deployed configuration.

In accordance with the present disclosure, as the pouch 22 is moved from the fully retracted configuration to the extended configuration, the pouch 22 is moved to a release configuration to facilitate uncoupling of the pouch 22 from the inner shaft 16 so that the pouch 22 may be cinched and removed from a patient as will be discussed in detail below. To this end, the inner shaft 16 supports a sled 24 that is coupled to a retention member 26 (FIG. 2) by a coupling member 40. The retention member 26 and the sled 24 are configured to facilitate detachment of the pouch 22 from a support mechanism 28 provided at a distal end 30 (FIG. 6)

of the inner shaft 16 (See FIG. 3) upon movement of the inner shaft 16 from the fully retracted position to the extended position.

Figure 2A:
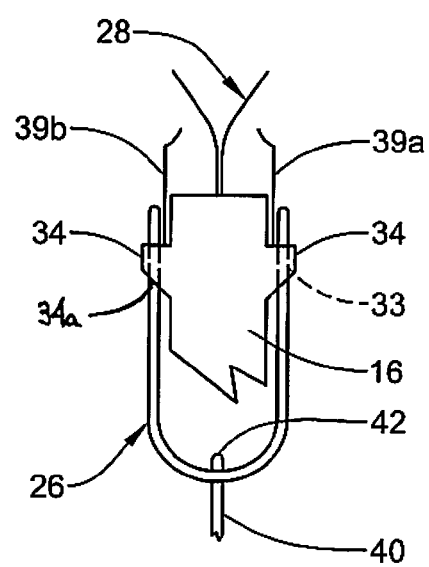
FIG. 2A is an enlarged schematic view of the connection of the pouch with the inner shaft with the retention member in a locked position.

Referring to FIGS. 2 and 2A, the retention member 26 includes a bifurcated configuration having left and right side portions 27a, 27b, respectively that are joined at a proximal end 32 of the retention member 26. The left and right side portions 27a and 27b can include wires, rods or the like. With the retention member 26 in a distal most position (as shown in FIG. 2A), the left and right side portions 27a, 27b of retention member 26 extend through corresponding slots 33 defined in side protrusions 34 of inner shaft 16. Each side protrusion 34 is configured to be releasably received within a corresponding aperture 3638 (FIG. 1) defined through tab portions 39a and 39b of the pouch 22 (FIGS. 1, 2 and 6). The left and right tab portions 39a, 39b of the pouch 22 are provided adjacent a proximal end 41 (FIG. 1) of the pouch 22 and extend proximally therefrom for releasably coupling to the corresponding side protrusions 34 on the inner shaft 16. With the retention member 26 in the distal most position, the left and right side portions 27a, 27b of the retention member 26 prevent tab portions 39a, 39b from becoming disengaged from protrusions 34. The retention member 26 is movable from the distal most position to a proximal most position in relation to the inner shaft 16 to allow a clinician to uncouple the pouch 22 from the support mechanism 28, as will be described in greater detail below.

Figure 5:
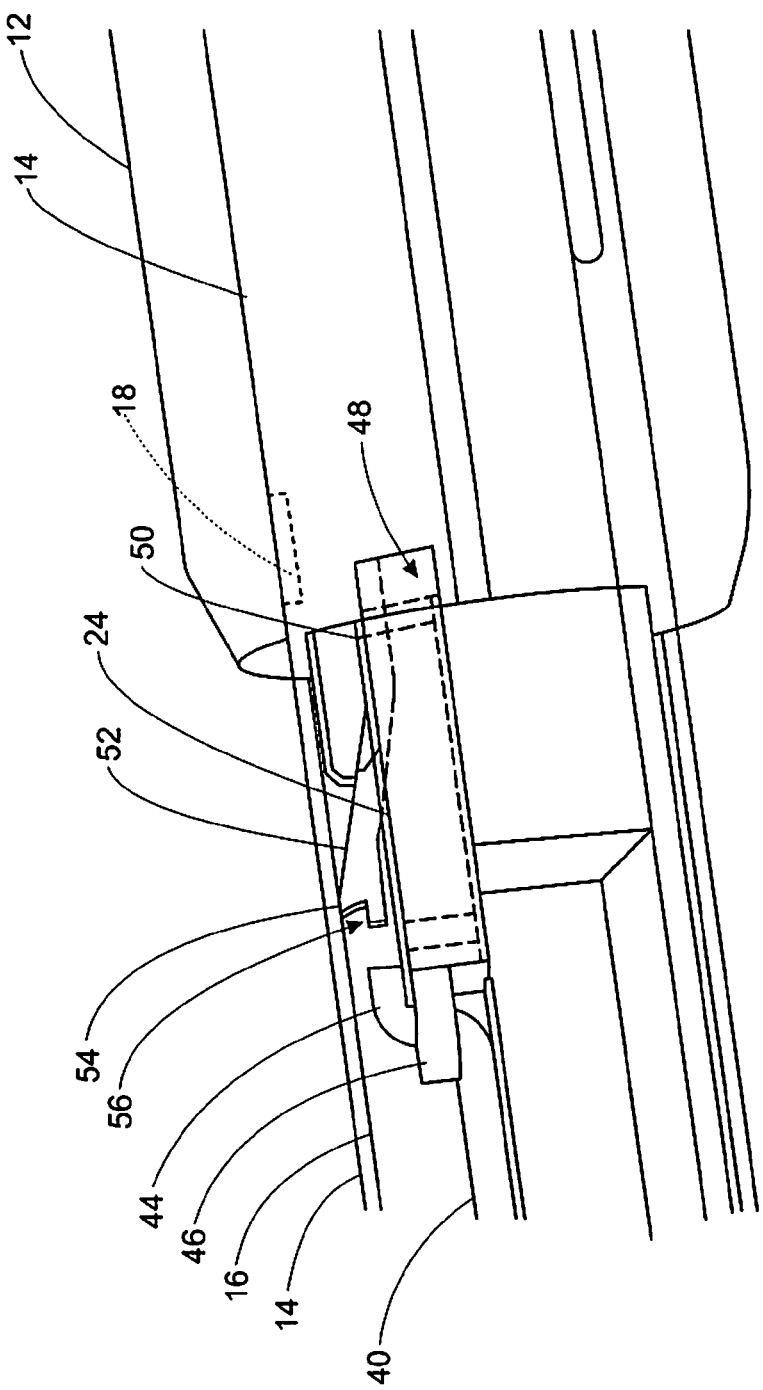
FIG. 5 is an enlarged perspective view of a distal end of the housing with a portion of an outer shaft which extends from the housing removed to illustrate a spatial relationship of the components of the sled subsequent to the sled being moved distally in relation to the stop member.

Referring to FIGS. 2 and 5, the coupling member 40, which may be in the form of a wire, cable, rod or the like, is configured to couple the retention member 26 to the sled 24. Specifically, the coupling member 40 includes a distal hook portion 42 (FIG. 2) that is coupled to the proximal end 32 of the retention member 26, either fixedly or releasably, and a proximal hook portion 44 (FIG. 5) that is coupled to a distal end 46 of the sled 24, either fixedly or releasably. Those skilled in the art will appreciate other coupling methods that may be utilized to couple the coupling member 40 to the retention member 26 and the sled 24. For example, the proximal and distal hook portions 44, 42 may be eliminated and proximal and distal ends of the coupling member 40 may be soldered, brazed or welded directly to the respective proximal and distal ends 32, 46 of the retention member 26 and sled 24.

Referring to FIGS. 2 and 4-5, the sled 24 has a generally elongated configuration and is seated within a notch 48 (FIGS. 4 and 5) that is defined by a top wall portion 50 of the inner shaft 16. The sled 24 is slidable along the notch 48 to move between distal and proximal positions within the notch 48. The sled 24 includes a resilient finger portion 52 including a distal end 54 configured to contact the boss 18 of the housing 12. An optional cutout 56 (FIG. 5) of suitable configuration may be provided at the distal end 54 of finger portion 52 to engage a corresponding mechanical interface provided on the boss 18 to facilitate engagement of the resilient finger portion 52 with the boss 18. The distal end 46 of the sled 24 defines an aperture (not explicitly shown) that is configured to receive the proximal hook portion 44 of coupling member 40. As can be appreciated, in embodiments where the proximal hook portion 44 is not utilized with the coupling member 40, the sled 24 may be formed without the aperture and the proximal end of the coupling member 40 may be attached to the sled 24 in any known manner, e.g., via welding.

Referring to FIGS. 1 and 6, the support mechanism 28 includes two flexible or resilient members 58 and 60 that form an open fork configuration. The flexible or resilient members 58, 60 can be formed from spring steel, Nitinol™ or the like. In the illustrated embodiment, the resilient members 58, 60 are joined at a proximal end of the support mechanism 28 and are coupled to the distal end 30 of the inner shaft 16 via one or more suitable coupling methods. In the illustrated embodiment, for example, the distal end 30 of the inner shaft 16 is overmolded about the proximal end of the resilient members 58 and 60 of the support mechanism 28.

The resilient members 58, 60 are configured to move from a stressed or non-expanded state when the pouch 22 is in a retracted configuration positioned within the outer shaft 14 to an unstressed or expanded state when pouch 22 is deployed from outer shaft 14. In the unstressed or expanded condition, resilient members 58, 60 collectively form a generally circular or hoop-like configuration for supporting a periphery of an opening 15 of pouch 22, see FIG. 1 for example. Persons skilled in the art will recognize that resilient members 58, 60 can form a multitude of configuration shapes, such as generally elliptical.

In accordance with the present disclosure, resilient members 58, 60 are configured to releasably couple the pouch 22 to a distal end of inner shaft 16. Specifically, resilient members 58, 60 may be fed through a tubular portion or sleeve 17 (FIG. 6) of suitable configuration that is provided about an upper end of the pouch 22. When the retention member 26 is disengaged from side protrusion 24 of inner shaft 16, proximal movement of the inner shaft 16 within the outer shaft 14 causes a proximal portion 41 of pouch 22 to contact a distal end of the outer shaft 14. After the pouch 22 engages the distal end of the outer shaft 16, further proximal movement of the inner shaft 16 proximally into outer shaft 14 causes the resilient members 58, 60 to slide out of the sleeve 17 of the pouch 22 to uncouple the pouch 22 from the resilient members 58, 60 as discussed in further detail below.

Referring again to FIG. 1, a handle, e.g., a finger loop 23, is provided at a proximal end of the inner shaft 16 and is configured to facilitate movement of the inner shaft 16 in relation to the outer shaft 14 and the housing 12, e.g., via manual grasping by the clinician. Other handle configurations are envisioned. A cinch puller 62 is removably coupled to the finger loop 23 via a press-fit or friction engagement and is configured to close pouch 22 after a tissue specimen is positioned therein as is known in the art. More specifically, the cinch puller 62 is connected to a suture "S". A distal end of the suture "s" is coupled to the pouch 22 (FIG. 6). For example, the suture "S" can extend about the opening 15 of pouch 22 through the cuff 17 as is known in the art. In embodiments, the cinch may be in the form of a thread, wire, cable or the like. In use, after the pouch 22 is in abutment with the distal end of the outer tube 14 and the pouch 22 is uncoupled from the support mechanism 28, the cinch puller 62 can be pulled proximally in relation to the outer tube 14 to draw the suture "S" proximally to close the opening 15 (FIG. 1) of pouch 22.

The pouch 22 may be made from any suitable biocompatible material (e.g., nylon, urethane, ripstop nylon or latex) capable of forming a flexible collapsible member, or membrane. Pouch 22 includes a generally tubular or elongated configuration that is defined by an openable and closable upper portion (or mouth) 19 which defines the opening 15 and a closed lower portion 21 (FIG. 1). The upper portion 19 includes the sleeve 17 that is configured to receive resilient members 58, 60 therein and a distal portion of the suture "S" (FIG. 6). In the illustrated embodiment, the distal portion of the suture "S" is positioned through one end of the sleeve 17 and is coupled to the pouch 22 or a distal end of the retrieval device 10 at the other end of the sleeve 17. Thus, when the cinch puller 62 is pulled proximally, the suture "S" closes the opening 15 of the upper portion 19.

The specimen retrieval device 10 may be packaged and shipped with the pouch 22 in a deployed configuration and the inner shaft 16 in a partially retracted position. As discussed above, shipping the specimen retrieval device 10 with the pouch 22 deployed will minimize the likelihood of formation of memory wrinkles in the pouch 22. Prior to use, the inner shaft 16 may be moved proximally in relation to the outer shaft 14 from the partially retracted position to a retracted position to position the pouch 22 within the outer shaft 14 to facilitate insertion of the outer shaft 14 through a small incision or cannula. As the inner shaft 16 is moved proximally from the partially retracted position towards the fully retracted position in relation to the outer shaft 14, the resilient finger portion 52 of sled 42 is deflected downwardly via engagement with the boss 18 to allow the sled 24 to move to a proximal side of the boss 18. In doing so, the pouch 22 is drawn at least partially into the outer shaft 14. In this position, the sled 24 is positioned at a distal end of the notch 48 defined on the inner shaft 16. Thereafter, the outer shaft 14 may be inserted through a natural or man-made orifice on a patient and positioned adjacent target tissue. As discussed below, movement of the retention member 26 in relation to the inner shaft 16 effects disengagement of the retention member 26 from the side protrusions 34 of the inner shaft 16. More specifically, when the inner shaft 16 is moved distally in relation to the outer shaft 14 to deploy the pouch 22 from the outer shaft 14, the distal end 54 of the finger portion 52 (FIG. 4) of sled 24 will temporarily engage the boss 18 to prevent the sled 24 and the retention member 26 from moving distally with the inner shaft 16. Movement of the inner shaft 26 independently of the sled 24 and the retention member 26 causes the portions 27a, 27b of the retention member 26 to disengage from the slots 33 of side protrusions 34 when the inner shaft 16 is moved towards the extended position.

The distal end 54 of the finger portion 52 remains engaged with the boss 18 until distal translation of the inner shaft 16 in relation to sled 24 and the outer shaft 14 causes the top wall 50 (FIG. 4) of the inner shaft 16 that defines the notch 48 to contact the finger portion 52. The top wall 50 slides along a top surface of the finger portion 52 and urges the finger portion 52 downwardly out of engagement with the boss 18 so that the sled 24 may again move distally with the inner shaft 16 in relation to the outer shaft 14 (FIG. 5). Continued distal movement of the inner shaft 16 in relation to the outer shaft 14 ultimately moves the pouch 22 to the deployed configuration (FIG. 6 illustrates the top portion of the pouch 22 for clarity).

After the pouch 22 is deployed and the surgical procedure is completed, the inner shaft 16 can be withdrawn into the outer shaft 14 to separate the pouch 22 from the inner shaft 16. Such a separating force is generated by a clinician pulling proximally on the handle 23 at the proximal end of the inner shaft 16. More specifically, once the tab portions 39a, 39b of the pouch 22 are no longer locked onto the left and right protrusions 34 of the inner shaft 16 by the retention member 26, pulling the inner shaft 16 proximally in relation to the outer shaft 14 causes the proximal end of pouch 22 to abut the distal end of the outer shaft 14. As a result, when the inner shaft 16 is withdrawn back into the outer shaft 14, the tab portions 39a and 39b are disengaged from the protrusions 34 to separate the pouch 22 from the inner shaft 16. The protrusions 34 may have proximal chamfers 34a (FIG. 6) to facilitate separation from tab portions 39a, 39b. Thereafter, the resilient members 58, 60 of the support mechanism 28 are caused to slide out of the sleeve 17 of the pouch 22 as the inner shaft 16 is retracted into the outer shaft 14, until resilient members 58, 60 of the support mechanism 28 are no longer supporting the pouch 22.

Once the pouch 22 has been de-coupled from the inner shaft 16, a clinician may detach the cinch puller 62 from the finger loop 23 of the inner shaft 16. In an embodiment, the suture "S" may be detached from the inner shaft 16 and the inner shaft can be withdrawn from the outer shaft 14. With the inner shaft 16 removed, the remaining portion of the suture "S" extends longitudinally through the outer shaft 14. Pulling the suture "S" causes the suture "S" to tighten about the opening 15 of the pouch 22 to close the opening 15. The outer shaft 14 may then be withdrawn from the surgical site, leaving just the closed pouch 22 within the surgical site and a portion of the suture "S" extending through the incision.

Unlike conventional specimen retrieval devices that are typically shipped for use with a pouch that is folded or rolled and stored within an outer shaft of the specimen retrieval device, the present specimen retrieval device 10 may be shipped for use with the pouch 22 in an unfolded and deployed configuration, e.g., outside of the outer shaft 14. Such an arrangement may overcome drawbacks typically associated with conventional specimen retrieval devices, e.g., the likelihood of memory wrinkles being formed on pouch 22 is reduced, if not eliminated.

From the foregoing and with reference to the various drawings, those skilled in the art will appreciate that certain modifications can also be made to the present disclosure without departing from the overall scope. For example, one or more devices or components may be utilized to assist in separating the pouch 22 from the resilient members 58, 60 of the support mechanism 28.

Figure 7:
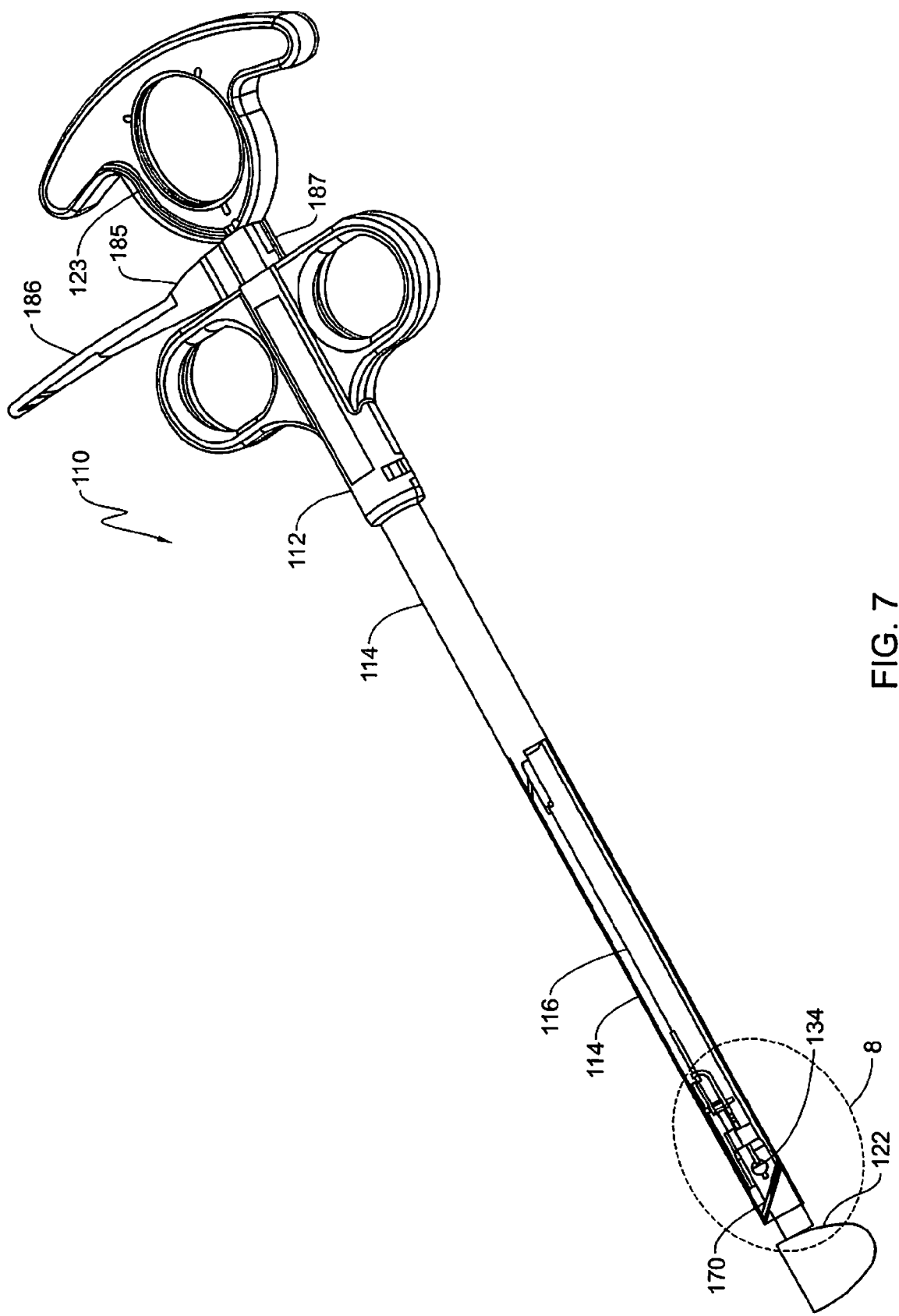
FIG. 7 is a perspective view of a specimen retrieval device in accordance with another embodiment of the present disclosure.
Figure 8:
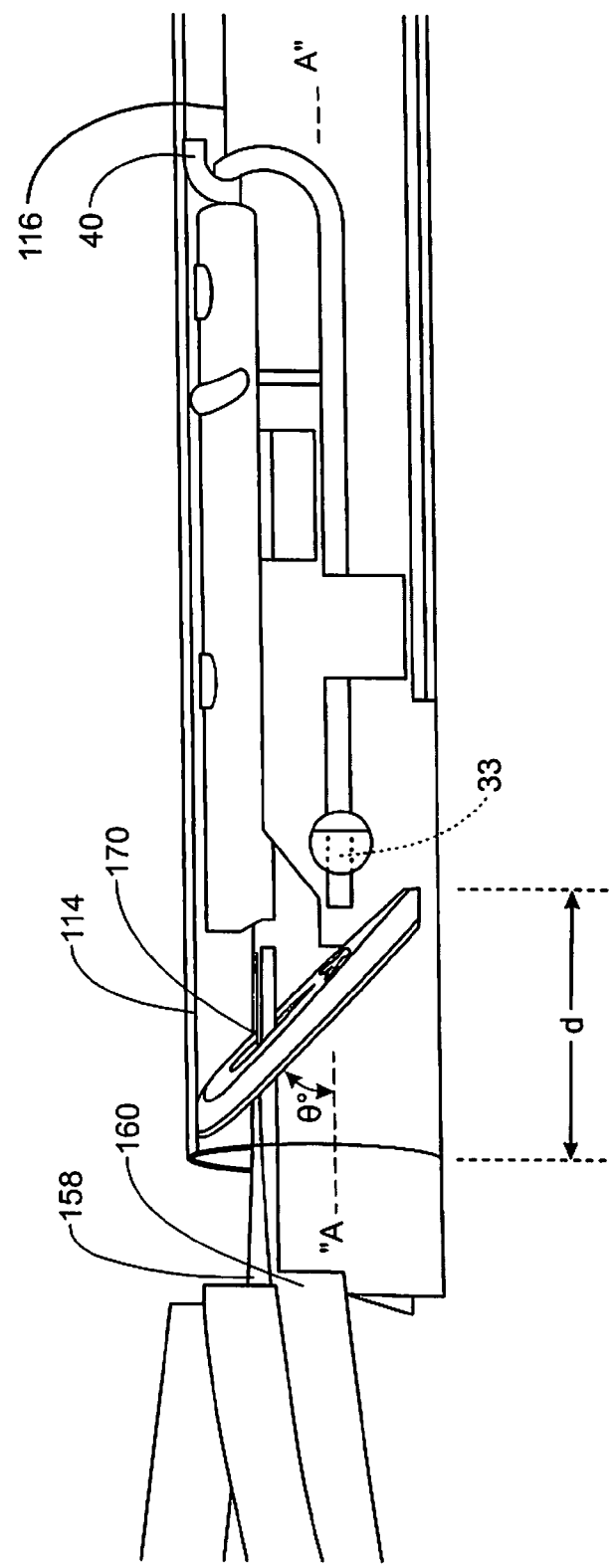
FIG. 8 is the indicated area of detail shown in FIG. 7.

For example, FIG. 7 illustrates, a specimen retrieval device 110 which includes a stripper plate 170. The stripper plate 170 is configured to be received within an outer shaft 114 of the specimen retrieval device 110 and be deployed when the inner shaft 116 is moved to a fully extended position to assist in separating the pouch 122 from the support mechanism 128 (FIG. 8). Specimen retrieval device 110 is similar to the specimen retrieval device 10. Accordingly, only those features unique to specimen retrieval device 110 are described herein.

Figure 11:
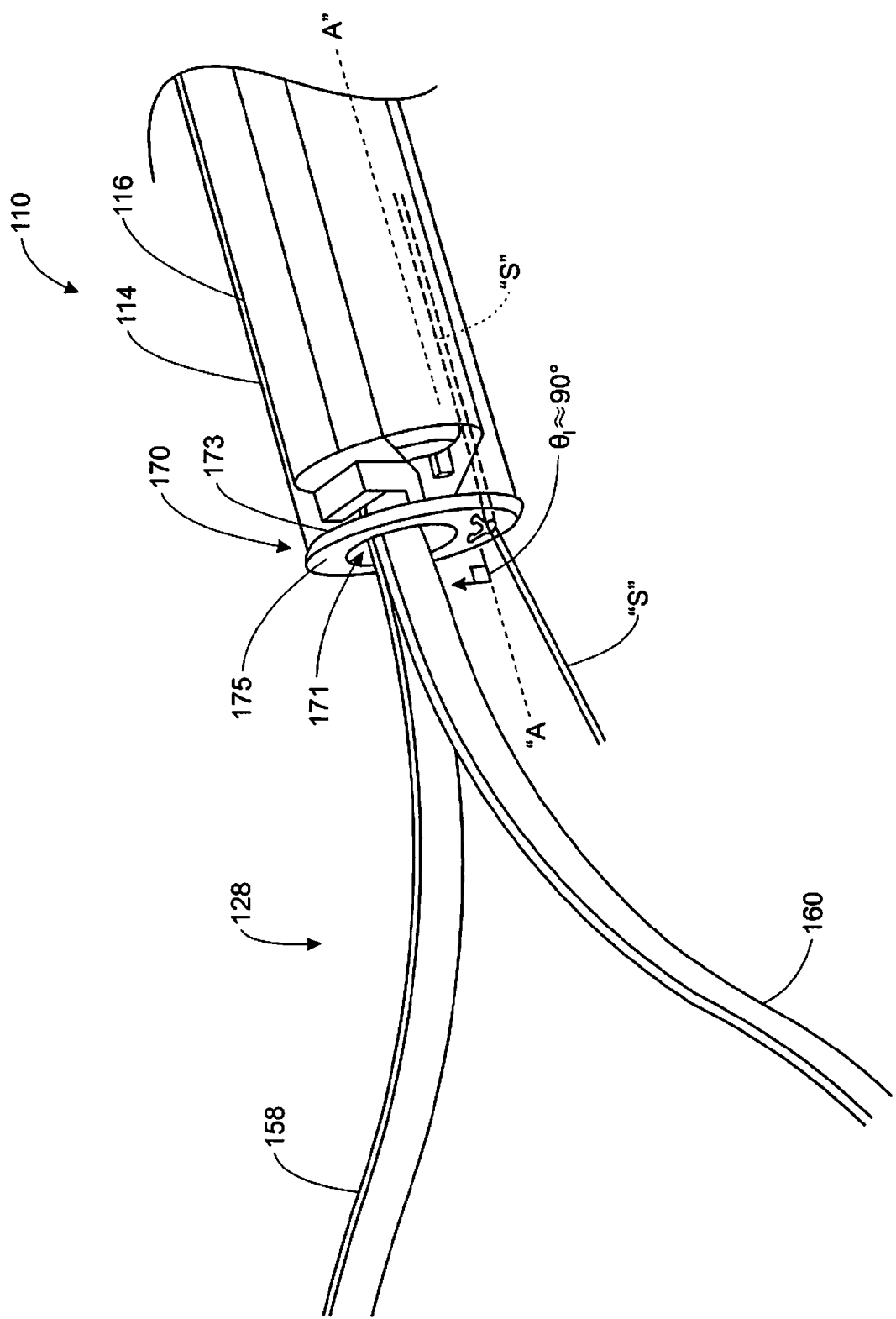
FIG. 11 is the indicated area of detail shown in FIG. 10.

Referring to FIGS. 7 and 8, the stripper plate 170 is movable from a retracted configuration wherein the stripper plate 170 is disposed within a distal end of the outer shaft 114 of the specimen retrieval device 110 to a deployed configuration wherein the stripper plate 170 is disposed outside of the outer shaft 114 (FIG. 11). As will be discussed in further detail below, in the retracted configuration, the stripper plate 170 may be oriented at a first angle 0° relative to a longitudinal axis "A-A" defined through the outer shaft 114 (as shown in FIG. 8). The first angle 0° of the stripper plate 170 may range from about 1 degree to about 75 degrees.

Figure 9A:
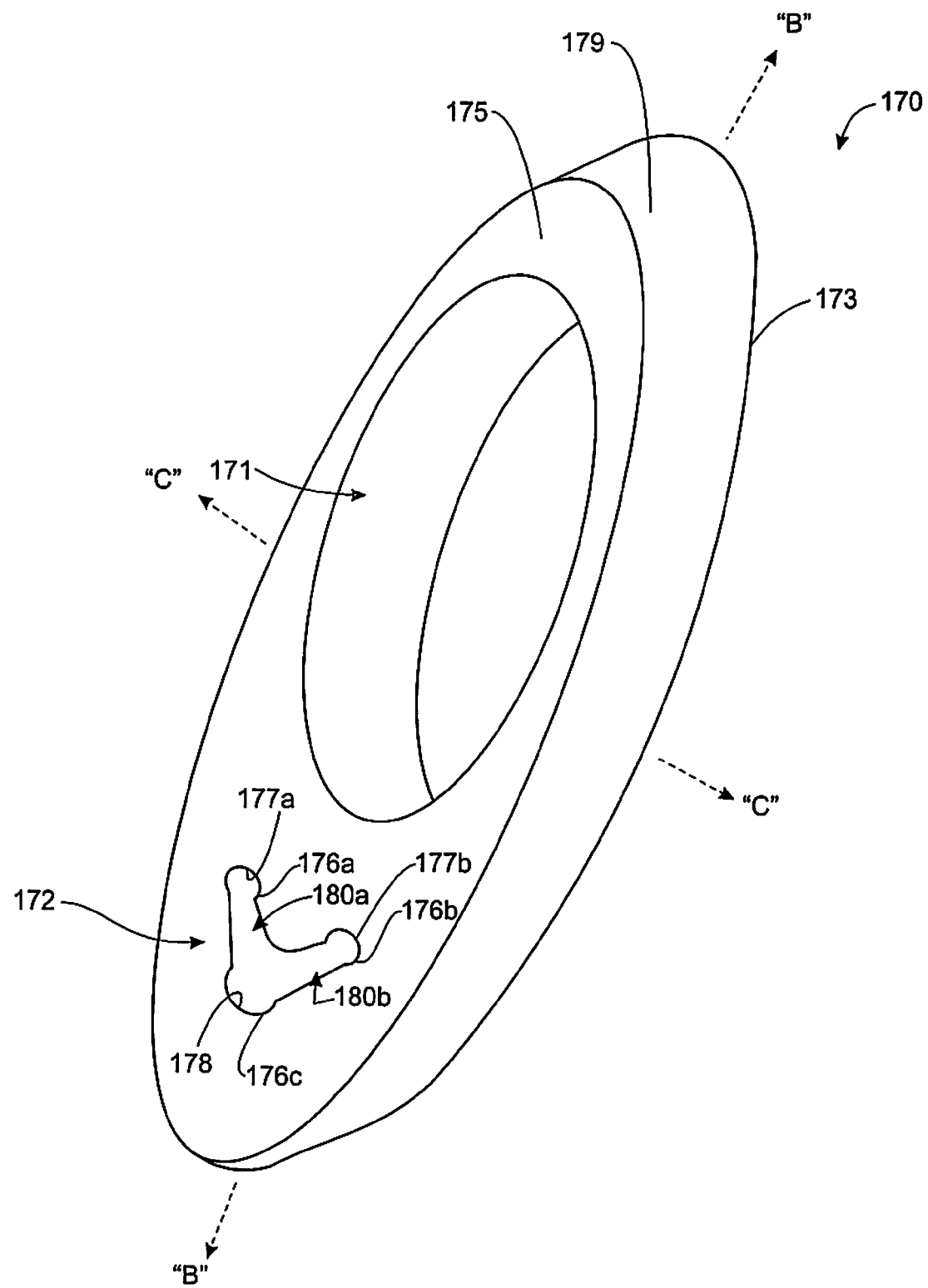
FIG. 9A is an enlarged perspective view of a stripper plate configured for use with the specimen retrieval device shown in FIG. 7.
Figure 9B:
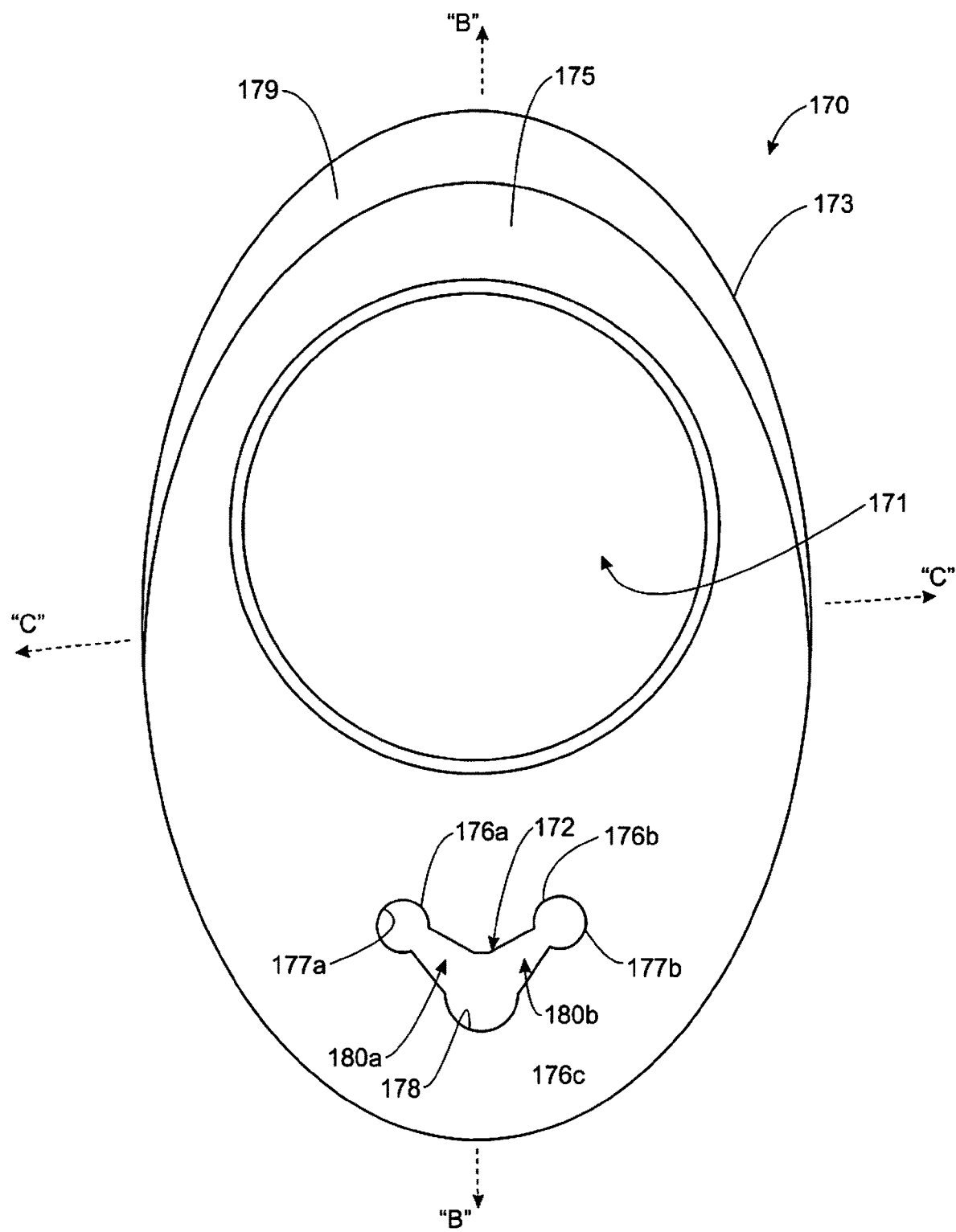
FIG. 9B is an enlarged front end view of the stripper plate shown in FIG. 9A.

Referring to FIGS. 9A-9B, in embodiments, the stripper plate 170 includes a generally elliptical configuration defining a major axis "B-B" and minor axis "C-C." A width of the minor axis "C-C" is smaller than an inner diameter of the outer shaft 114 and a width of the major axis "B-B" is greater than the inner diameter of the outer shaft 114. It is noted that having the major axis "B-B" greater than the inner diameter of the outer shaft 114 prevents the stripper plate 170 from being moved back into the outer shaft 114 after the stripper plate 170 has been deployed from the outer shaft 114. A leading end 175 of the stripper plate 170 includes a generally planar configuration with a generally oval shaped peripheral wall 179 which extends between the leading end 175 and a trailing end 173 of the stripper plate. The peripheral wall 179 may be beveled at an angle that ranges from about 25 degrees to about 45 degrees in relation to the planar leading end 175 of the stripper plate 170 to allow the peripheral wall 179 to frictionally engage an inner surface of outer shaft 114 (FIG. 8). As shown, the angle of peripheral wall 179 of the stripper plate 170 is substantially parallel to the inner surface of the outer shaft 114 to allow the stripper plate 170 to be deployed from the outer shaft as will be discussed in further detail below.

Continuing with reference to FIGS. 9A-9B, the stripper plate 170 includes first and second apertures 171, 172 defined therethrough. The first aperture 171 of the stripper plate 170 has a generally circular shape and is configured to receive the resilient members 158, 160 of the support mechanism 128 (FIG. 8).

The second aperture 172 has a generally triangular shape and is configured to receive the suture "S" of the specimen retrieval device 110 (FIG. 11). In embodiments, the second aperture 172 may be further defined by an upper first portion 176a, an upper second portion 176b and a lower portion 176c. Each of the upper first and second portions 176a, 176b may be defined by generally circumferential walls 177a, 177b and the lower portion 176c may be defined by a lower generally concave wall 178. The upper first and second portions 176a, 176b are sized proportionally to the suture "S" to exert a drag force on the suture "S" as the suture "S" is being pulled through the first or second portions 176a, 176b. In one embodiment, the suture "S" passes through one of the first or second portions 176a, 176b, extends through the sleeve and about the opening in the pouch 122, and then passes back through the other opening 176a, 176b of the stripper plate 170 where the suture "S" is secured to the trailing end 173 of the stripper plate 170. When the suture "S" is pulled proximally, the suture "S" cinches the opening is in the pouch 122.

First and second opposing channels 180a, 180b are provided between the upper first and second portions 176a, 176b, respectively, and the lower portion 176c of the stripper plate 170. The first and second opposing channels 180a, 180b help guide the suture "S" into the upper first portion 176a and upper second portion 176b, respectively, as the suture "S" is being pulled proximally to close the pouch 122 (see FIG. 7 for example) of the specimen retrieval apparatus 110. Persons skilled in the art will recognize that first and second apertures 171 and 172 may each be of any known configuration, such as circular, oval, square, rectangular, Y-shaped or X-shaped, with either sharp or curved/concave corners or edges. Furthermore, the inner walls of each of the first and second apertures 171 and 172 may be angled, for example inward or outward, relative to the front face of the stripper plate 170.

Figure 9C:
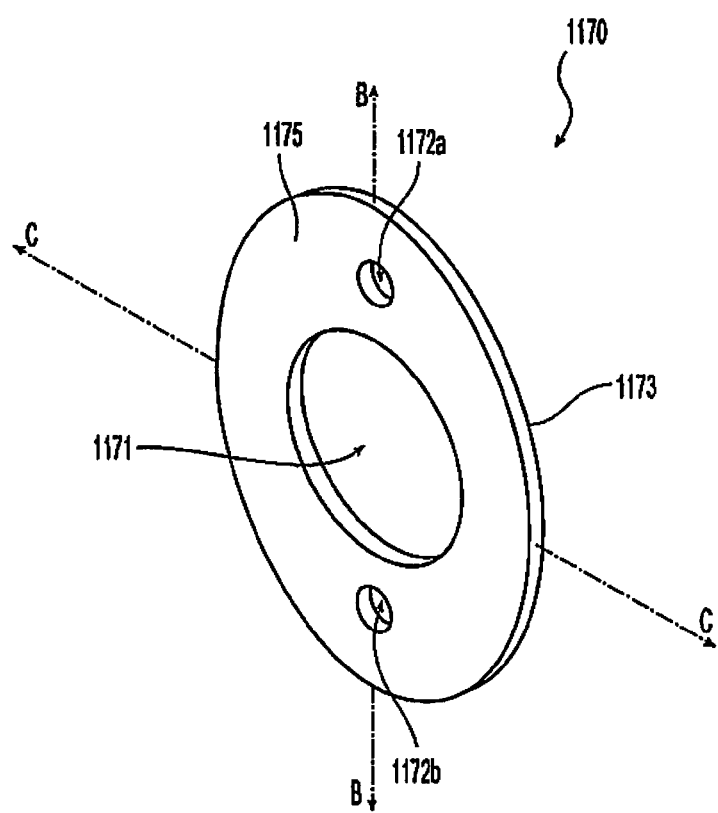
FIGS. 9C-9G are perspective views of other embodiments of stripper plates according to the present disclosure.
Figure 9D:
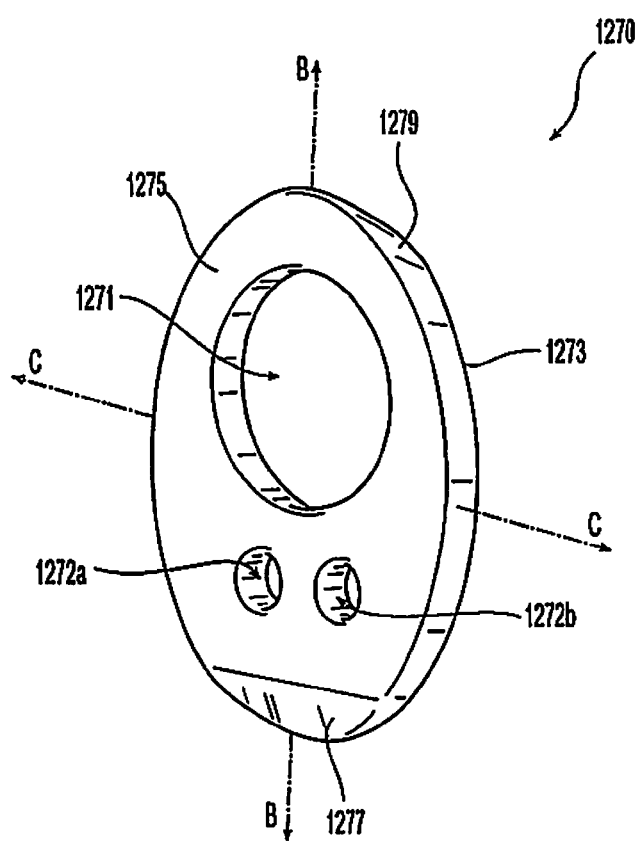
Figure 9E:
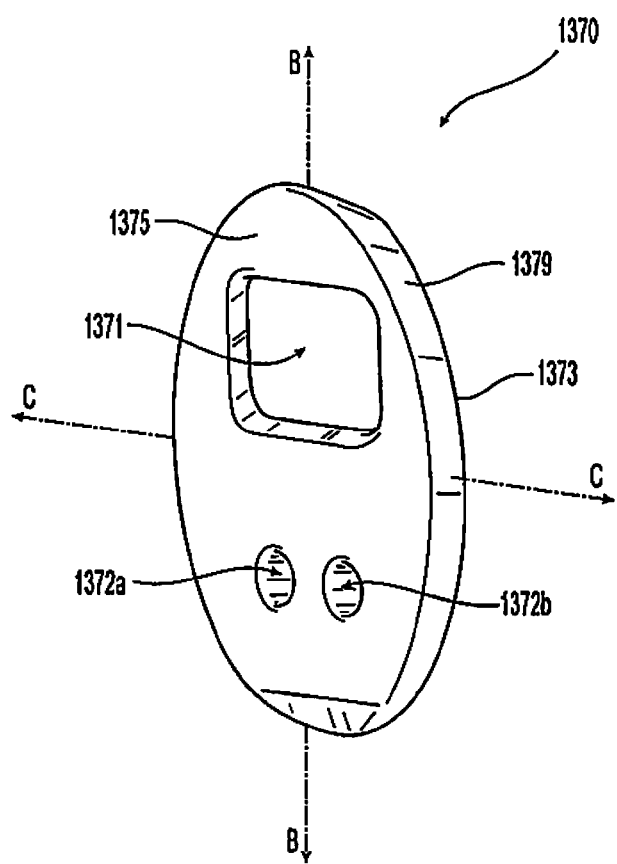
Figure 9F:
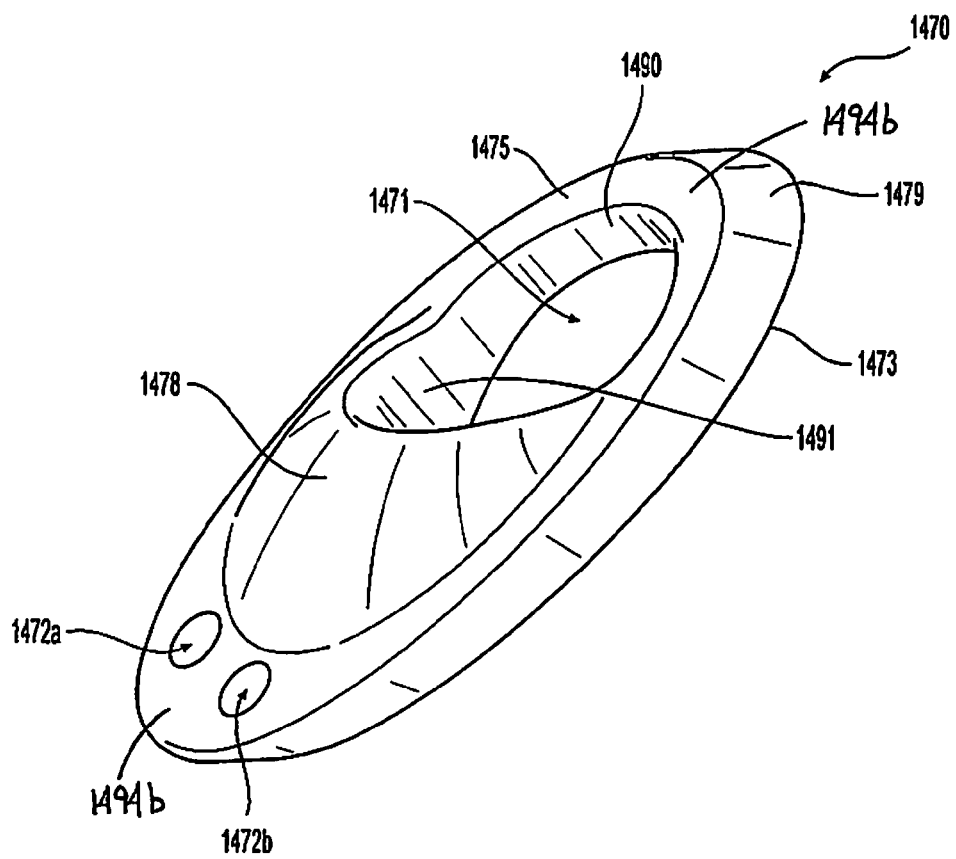
Figure 9G:
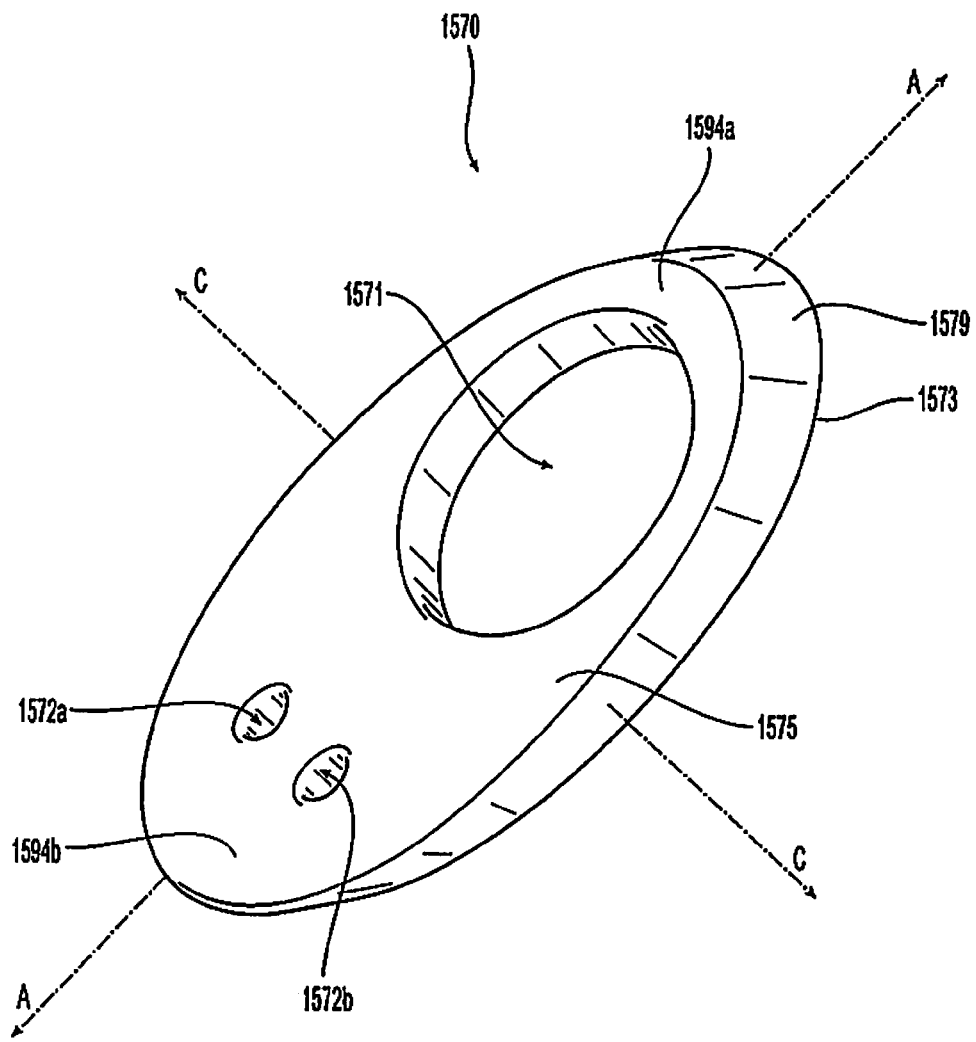
Figure 9H:
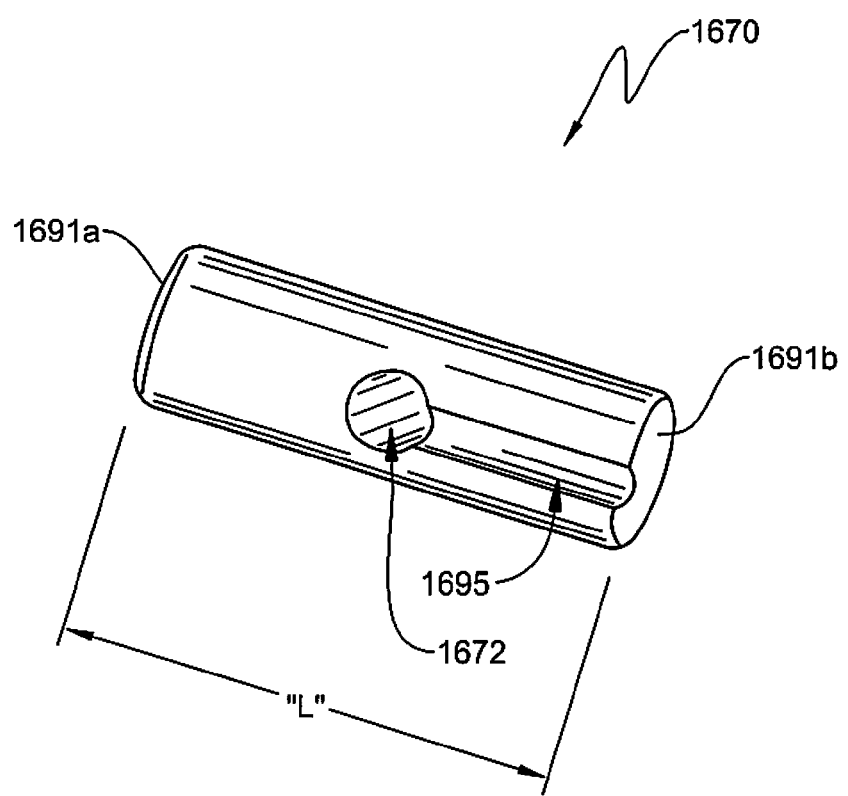
FIGS. 9H-9J are perspective views of cylindrically-shaped embodiments of stripper plates according to the present disclosure.
Figure 9I:
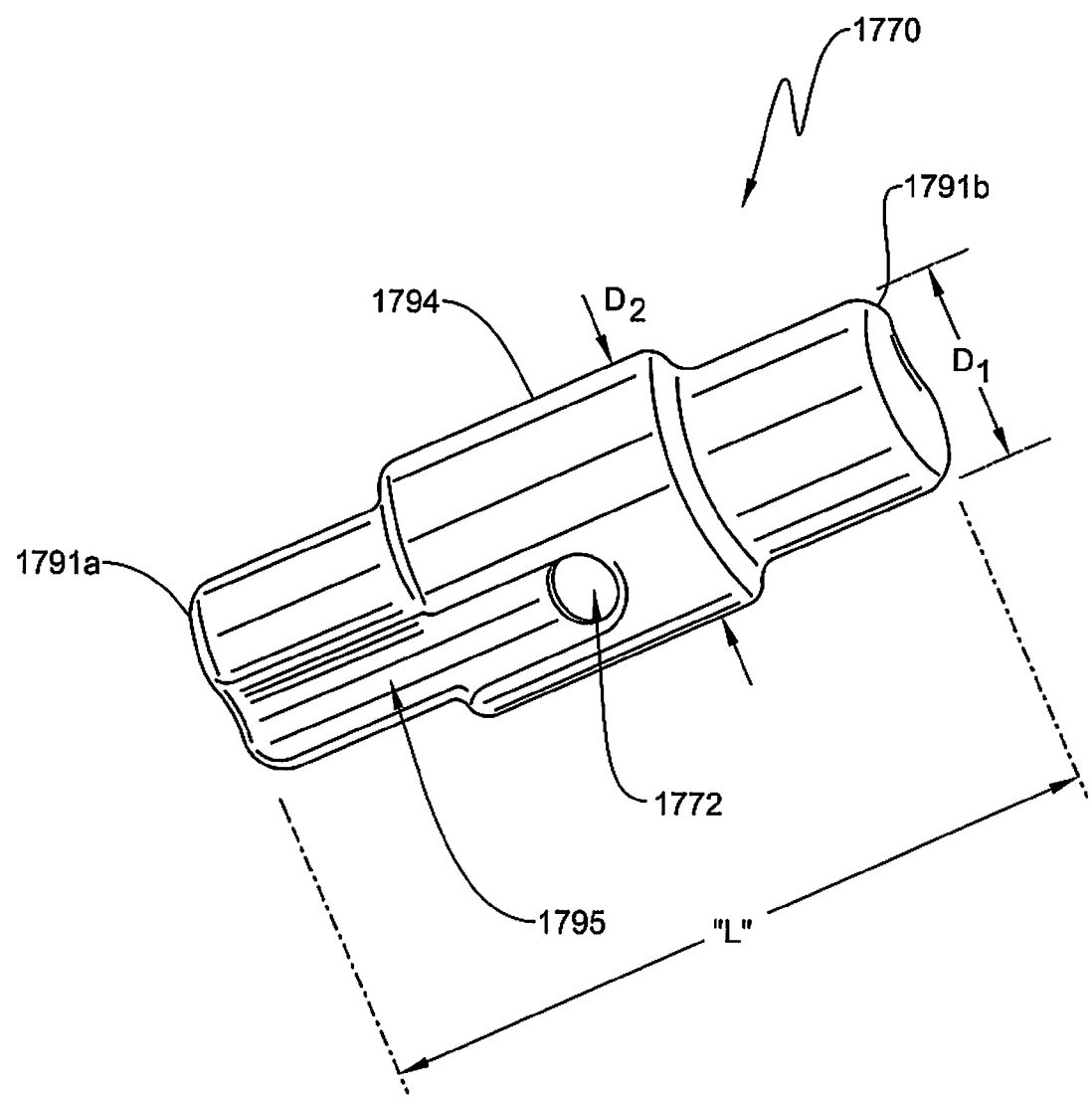
Figure 9J:
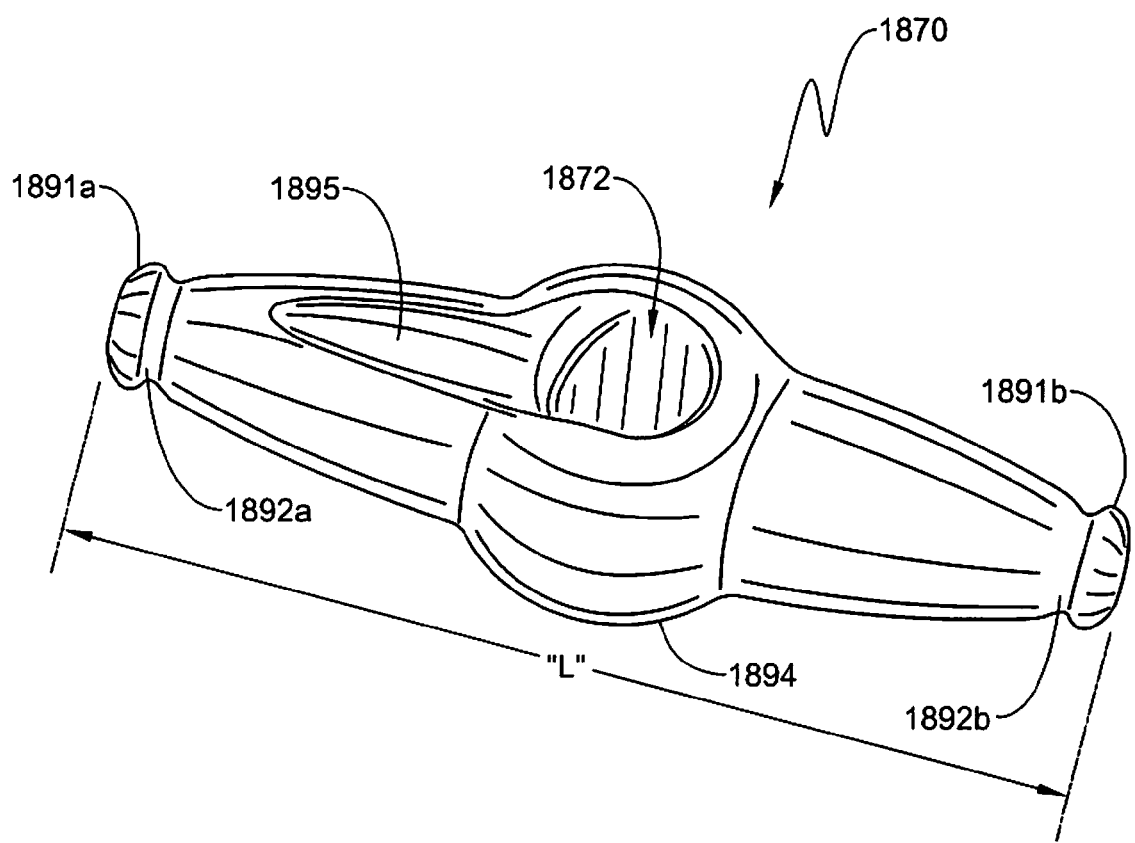
Figure 9K:
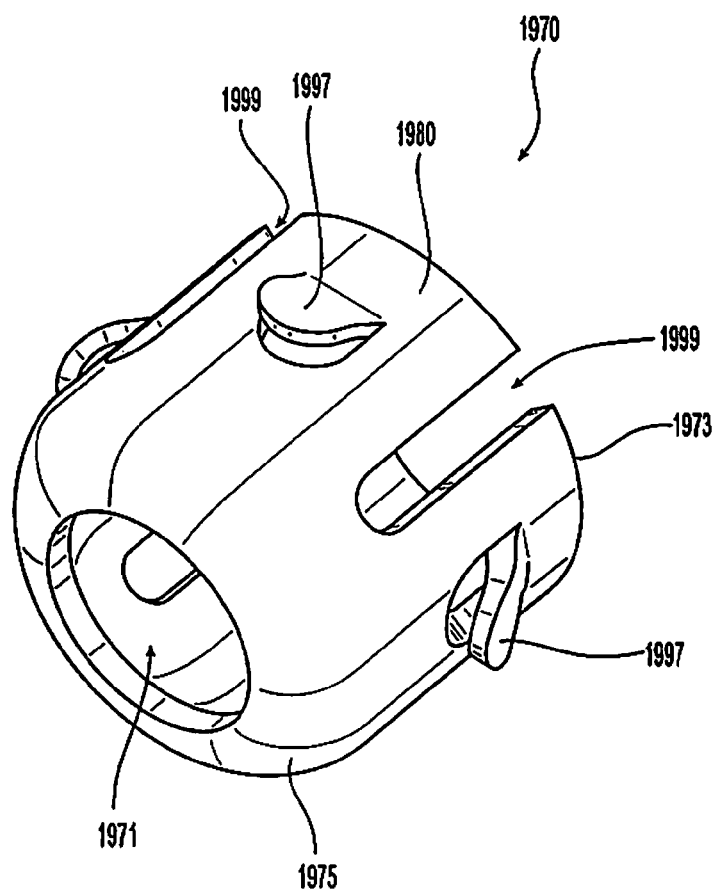
FIG. 9K is a perspective view of another embodiment of a stripper plate according to the present disclosure.
Figure 10:
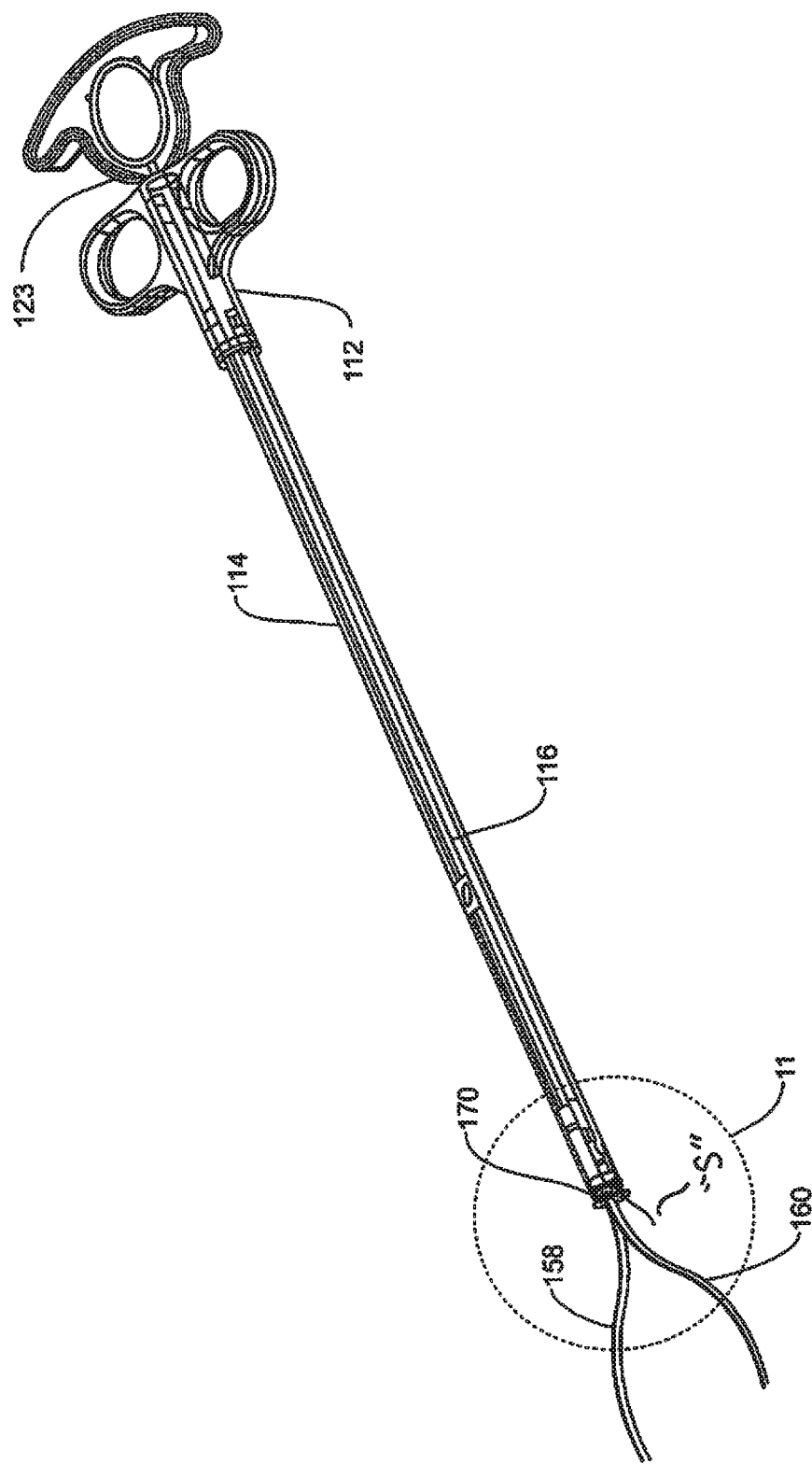
FIG. 10 is a perspective view of the specimen retrieval device shown in FIG. 10 with the stripper plate shown in an extended position.

Referring to FIGS. 10-11, the stripper plate 170 is supported on the resilient members 158, 160 of the support mechanism 128 which is configured to support the pouch 122. In the embodiment illustrated in FIGS. 7-11, the tab portions 39a, 39b (FIG. 1) of the pouch 122 are configured to extend around the minor axis "C-C" (FIG. 9A) of the stripper plate 170 for coupling to the side protrusions 134 (FIG. 8) provided on an inner shaft 116 of the specimen retrieval device 110.

As will be described in further detail below, in use of the specimen retrieval device 110, the inner shaft 116 is movable from a partially retracted position to a fully retracted position and then to a fully extended position. In the partially retracted position of the inner shaft 116 (FIGS. 7 and 12A), which is the shipping position, the pouch 122 is deployed but the stripper plate 170 is positioned within the outer shaft 114. In this position, as will be discussed in further detail below, a locking member prevents advancement of the inner shaft 114 to the fully extended position until the inner shaft 116 is first moved to the fully retracted position. Movement of the inner shaft 116 to the fully retracted position, which in some embodiments releases the locking member, draws the pouch into the outer shaft 114 to facilitate insertion of the outer shaft 114 through a small incision or cannula. Movement of the inner shaft 116 from the fully retracted position to the extended position (FIGS. 11 and 12B) redeploys the pouch 122, deploys the stripper plate 170 and, as discussed above with regard to FIGS. 1-6, disengages the retention member 26 from the protrusions 34 (FIG. 2A) to facilitate separation of the pouch 122 from the inner shaft 116.

FIGS. 9C-9K show alternate embodiments of stripper plates 1170, 1270, 1370, 1470, 1570, 1670, 1770, 1870, and 1970 for use with the present disclosure. As can be appreciated, any one of these disclosed stripper plates 1170, 1270, 1370, 1470, 1570, 1670, 1770, 1870, and 1970 may be utilized with any one of the specimen retrieval devices shown and described in this application, e.g., specimen retrieval devices 10 and/or 110, to assist in separating the pouch 122 from the resilient members 58, 60 and 158, 160 of the support mechanism 28, 128.

Referring to FIG. 9C, the stripper plate 1170 includes a generally elliptical configuration defining a major axis "B-B" and minor axis "C-C." Much like stripper plate 170, the width of the minor axis "C-C" is smaller than an inner diameter of the outer shaft 114 and a width of the major axis "B-B" is greater than the inner diameter of the outer shaft 114. Once again, it is noted that having the major axis "B-B" greater than the inner diameter of the outer shaft 114 ensures that the stripper plate 1170 cannot be moved back into the outer shaft 114 after the stripper plate 1170 has been deployed from the outer shaft 114.

Stripper plate 1170 includes a first aperture 1171 and a pair of second apertures 1172a, 1172b defined therethrough. The first aperture 1171 of the stripper plate 1170 has a generally circumferential shape and is configured to receive the resilient members 158, 160 of the support mechanism 128 (see FIGS. 10-11 for example).

The pair of second apertures 1172a and 1172b extend through the stripper plate 1170 and are each configured to frictionally receive a portion of a suture "S" of the specimen retrieval device 110 (similar to FIG. 11). The pair of second apertures 1172a and 1172b are configured to help guide the suture "S" as the suture "S" is pulled proximally to close the pouch 122 (see FIG. 7 for example) of the specimen retrieval apparatus 110. In one embodiment, the suture "S" extends through the opening 1172a, around the opening in pouch 122 and back through the opening 1172b where the suture "S" is secured to a trailing end 1173 of the stripper plate 1170.

Much like the stripper plate 170 described above, in the refracted configuration, the stripper plate 1170 is oriented at an angle 0° within the inner periphery of the outer shaft 114 (FIG. 8). When the stripper plate 1170 is moved from the retracted configuration to the deployed configuration (FIGS. 10-11), the stripper plate 1170 tilts about the resilient members 158, 160 and orients itself at a second angle 0° relative to the longitudinal axis "A-A". When the stripper plate 1170 is in the deployed configuration, proximal movement of the inner shaft 116 relative to the outer shaft 114 causes a trailing end 1173 of the stripper plate 1170 to contact the distal end of the outer shaft 114 and the pouch 122 to contact the leading end 1175 of the stripper plate 1170 as the support mechanism 128 (FIG. 8) passes through opening 1171 to uncouple the pouch 22 from the resilient members 158, 160 of the support member 128 of the inner shaft 116 as discussed above.

Referring to FIG. 9D, the stripper plate 1270 includes a generally elliptical configuration defining a major axis "B-B" and minor axis "C-C." Much like stripper plate 170, the width of the minor axis "C-C" is smaller than an inner diameter of the outer shaft 114 and a width of the major axis "B-B" is greater than the inner diameter of the outer shaft 114. Once again, it is noted that having the major axis "B-B" greater than the inner diameter of the outer shaft 114 ensures that the stripper plate 1270 cannot be moved back into the outer shaft 114 after the stripper plate 1270 has been deployed from the outer shaft 114. A leading end 1275 of the stripper plate 1270 includes a generally planar configuration with a generally oval shaped peripheral wall 1279 which extends between the leading end 1275 and a trailing end 1273 of the stripper plate 1270. The peripheral wall 1279 is beveled to define an angle that ranges from about 25 degrees to about 45 degrees in relation to the longitudinal axis A-A (FIG. 8) of the outer shaft 114 to facilitate proper orientation of the stripper plate 1270 within the outer shaft 114 as discussed above and to facilitate deployment of the stripper plate 1270 from the retracted configuration to the deployed configuration. Stripper plate 1270 also includes a chamfered front edge 1277 defined on leading end 1275 of the stripper plate 1270. Leading end 1275 of stripper plate 1280 is designed to face distally when stripper plate 1270 is disposed at the first angle 0° within outer shaft 114. The chamfered front edge 1277 and peripheral wall 1279 include a substantially corresponding angle 0° to facilitate deployment of the stripper plate from outer shaft 114. The corresponding angle 0° may be in the range of about 25 degrees to about 45 degrees.

Stripper plate 1270 includes a first aperture 1271 and a pair of second apertures 1272a, 1272b defined therethrough. The first aperture 1271 of the stripper plate 1270 has a generally circumferential shape and is configured to receive the resilient members 158, 160 of the support mechanism 128 (FIG. 11).

The pair of second apertures 1272a and 1272b are defined within a leading end 1275 of the stripper plate 1270 and are each configured to receive a portion of a suture "S" of the specimen retrieval device 110 for reasons discussed above. The pair of second apertures 1272a and 1272b are positioned adjacent each other and are configured to help guide the suture "S" as the suture "S" is being pulled proximally to close the pouch 22 of the specimen retrieval apparatus 110 (FIG. 7).

Much like the stripper plate 170 described above, in the retracted configuration, the stripper plate 1270 is oriented at an angle 0° within the inner periphery of the outer shaft 114 with the leading end 1275 of stripper plate 1270 facing distally. When the stripper plate 1270 is moved from the retracted configuration (FIG. 8) to the deployed configuration (FIG. 11), the stripper plate 1270 tilts about the resilient members 158, 160 and orients itself at a second angle 0° relative to the longitudinal axis "A-A". When the stripper plate 1270 is in the deployed configuration, proximal movement of the inner shaft 116 relative to the outer shaft 114 causes a trailing end 1273 of the stripper plate 1270 to contact the distal end of the outer shaft 114 and the pouch 122 to contact the leading end 1275 of the stripper plate 1270 to uncouple the pouch 122 from the resilient members 158, 160 of the support member 128 at the distal end of the inner shaft 116.

Referring to FIG. 9E, the stripper plate 1370 is similar to stripper plate 1270 with the exception that the first aperture 1371 includes a generally rectangular configuration. All other features of stripper plate 1370 are identical to stripper plate 1270 and operate in the same fashion, namely, second apertures 1372a and 1372b, major and minor axes "B-B" and "C-C", respectively, leading end 1375, trailing end 1373 and peripheral wall 1379.

Referring to FIG. 9F, the stripper plate 1470 is similar to stripper plate 1270 with the exception that the trailing end 1475 of the stripper plate 1470 also includes a bump-out or protuberance 1478 adjacent the first aperture 1471. The protuberance 1478 extends outwardly from the leading end 1475 proximate second apertures 1472a and 1472b. In embodiments, the bump-out 1478 may include a semi-circular configuration or a circular configuration. As a result, first aperture 1471 includes a trailing inner peripheral edge 1490 that is generally flush with trailing end 1475 and a leading inner peripheral edge 1491 that extends outwardly from trailing end 1475. All other features of stripper plate 1470 are identical to stripper plate 1270 and operate in the same fashion, namely, second apertures 1472a and 1472b, major and minor axes "B-B" and "C-C", respectively, leading end 1475, trailing end 1473 and beveled edge 1479. Trailing end 1475 includes a top portion 1494a and a bottom portion 1494b. Beveled peripheral edge 1479 extends from both the top and bottom portions 1494a, 1494b, respectively, at the same angle towards the leading end 1473 to facilitate seating of the stripper plate 1470 at a particular orientation within the inner periphery of the outer shaft 114 prior to deployment.

In the retracted configuration, the stripper plate 1470 is oriented at an angle 0° within the inner periphery of the outer shaft 114 with the trailing end 1475 and bump-out 1478 of stripper plate 1470 facing proximally. When the stripper plate 1470 is moved from the retracted configuration (FIG. 8) to the deployed configuration (FIG. 11), the stripper plate 1470 tilts about the resilient members 158, 160 and orients itself at a second angle 0° relative to the longitudinal axis "A-A". When the stripper plate 1470 is in the deployed configuration, proximal movement of the inner shaft 116 relative to the outer shaft 114 causes the trailing end 1475 of the stripper plate 1470 to contact the distal end of the outer shaft 114, and the pouch 122 to contact the leading end 1473 of the stripper plate 1470 to uncouple the pouch 122 from the resilient members 158, 160 of the support member 128 of the inner shaft 116. The bump-out 1478 is designed to be received in the inner periphery of the outer shaft 114 and center the stripper plate 1470 thereagainst along axis "A-A" (see FIG. 8).

In embodiments, bump-outs 1478 may be included on both the trailing end 1475 and leading end 1473 to facilitate alignment of the stripper plate within the outer shaft 114 and uncoupling of the pouch 22 from the resilient members 158, 160.

Referring to FIG. 9G, the stripper plate 1570 is similar to stripper plate 170 with the exception that the second apertures 1572a and 1572b for guiding the sutures "S" are different from the second triangular shaped aperture 172 of stripper plate 170. All other features of stripper plate 1570 are identical to stripper plate 170 and operate in the same fashion, namely, major and minor axes "B-B" and "C-C", respectively, leading end 1575, trailing end 1573 and peripheral wall 1579.

The pair of second apertures 1572a and 1572b extend through the stripper plate 1570. Each aperture 1572a, 1572b is configured to receive a corresponding portion of a suture "S" of the specimen retrieval device 110 as discussed above. The pair of second apertures 1572a and 1572b is configured to help guide the suture "S" as the suture "S" is being pulled proximally to close the pouch 122 (FIG. 7) of the specimen retrieval apparatus 110.

Much like the stripper plate 170 described above, in the retracted configuration, the stripper plate 1570 is oriented at an angle 0° within the inner periphery of the outer shaft 114. When the stripper plate 1570 is moved from the retracted configuration (FIG. 8) to the deployed configuration (FIG. 11), the stripper plate 1570 tilts about the resilient members 158, 160 and orients itself at a second angle 0° relative to the longitudinal axis "A-A". When the stripper plate 1570 is in the deployed configuration, proximal movement of the inner shaft 116 relative to the outer shaft 114 causes a trailing end 1573 of the stripper plate 1570 to contact the distal end of the outer shaft 114, and the pouch 122 to contact the leading end 1575 of the stripper plate 1570 to uncouple the pouch 122 from the resilient members 158, 160 of the support member 128 of the inner shaft 116.

FIGS. 9H-9J show alternate embodiments of stripper plates that may be utilized to both guide the suture "S" and assist in uncoupling the pouch 122 from the resilient members 158, 160. Unlike the aforedescribed stripper plates, e.g., stripper plate 170, the stripper plates shown in FIGS. 9H-9J are not configured with a first aperture dimensioned to receive the resilient members 158, 160 therethrough. Rather, these stripper plate designs are configured to allow the resilient members 158, 160 to extend distally on either side of the stripper plates.

Referring initially to FIG. 9H, a stripper plate 1670 is shown and includes a generally cylindrical configuration with a centralized aperture 1672 defined therethrough. The central aperture 1672 is configured to frictionally engage and guide the suture "S" therethrough in much the same manner as the second apertures, e.g., aperture 172, described above. The cylindrically-shaped stripper plate 1670 also includes a relief 1695 defined therein which is positioned proximate to and in communication with the aperture 1672 when the stripper plate 1670 is supported in the outer shaft 114. More specifically, when the stripper plate 1670 is positioned in the distal end of the outer shaft 114, the relief 1695 extends along an axis substantially parallel to the longitudinal axis of the outer shaft 114 to facilitate passage of the suture "S" from a proximal end of shaft 114 to the aperture 1672. The stripper plate 1670 includes a length "L" defined by outer end portions 1691a, 1691b. The length "L" is greater than the length of the inner diameter of the outer shaft 114 to ensure that the stripper plate 1670 cannot be moved back into the outer shaft 114 after the stripper plate 1670 has been deployed from the outer shaft 114.

In the retracted configuration, the stripper plate 1670 is supported within the outer shaft 114 with the resilient members 158, 160 extending on either side of the stripper plate 1670. It is envisioned that both of the resilient members 158, 160 may extend along one side of the stripper plate 1670. When the stripper plate 1670 is moved from the retracted configuration (FIG. 8) to the deployed configuration (FIG. 11), the stripper plate 1670 self aligns on either side of the resilient members 158, 160 and orients itself in a position extending across the distal end of the outer shaft 114. When the stripper plate 1670 is in the deployed configuration, proximal movement of the inner shaft 116 relative to the outer shaft 114 causes the stripper plate 1670 to contact the distal end of the outer shaft 114 and the pouch 122 to contact the stripper plate 1670 to uncouple the pouch 122 from the resilient members 158, 160 of the support member 128 of the inner shaft 116.

FIG. 9I includes a stripper plate 1770 that is similar to stripper plate 1670 with the exception that stripper plate 1770 includes a middle portion 1794 having a diameter D2 that is larger than the diameter D1 of the end portions of the stripper plate 1770. All other features of stripper plate 1770 are identical to stripper plate 1670 and operate in the same fashion.

For example, relief 1795 is configured to facilitate passage of the suture "S" through the aperture 1772. The stripper plate 1770 includes a length "L" defined by outer end portions 1791a, 1791b that is greater than the inner diameter of the outer shaft 114 to ensure that the stripper plate 1770 cannot be moved back into the outer shaft 114 after the stripper plate 1770 has been deployed from the outer shaft 114. Operation of the stripper plate 1770 is identical to that of stripper plate 1670 and will not be described in further detail herein.

FIG. 9J includes a stripper plate 1870 that is similar to stripper plate 1670 with the exception that stripper plate 1870 includes a bulging middle portion 1894 that surrounds an aperture 1872 and is tapered towards both ends 1891a and 1891b from bulging middle portion 1894. In addition, stripper plate 1870 includes a relief 1895 defined therein in communication with the aperture 1872 to facilitate passage of the suture "S" therethrough. The stripper plate 1870 includes a length "L" defined by outer end portions 1891a, 1891b that is greater than the inner diameter of the outer shaft 114 to ensure that the stripper plate 1870 cannot be moved back into the outer shaft 114 after the stripper plate 1870 has been deployed from the outer shaft 114.

Similar to the above stripper plates, stripper plates 1670 and 1770, proximal movement of the inner shaft 116 relative to the outer shaft 114 causes the stripper plate 1870 to contact the distal end of the outer shaft 114, and the pouch 122 to contact the stripper plate 1870 and to uncouple the pouch 122 from the resilient members 158, 160 of the support member 128 of the inner shaft 116. Recesses 1892a and 1892b are defined at each respective end portion 1891a and 1891b of the stripper plate 1870. Each recess 1892, 1892b is configured to engage opposing portions of the inner peripheral edge (not shown) of the distal end the outer shaft 114. As can be appreciated, the recesses 1892a, 1892 seat the stripper plate 1870 against the outer shaft 114 which, in turn, facilitates, uncoupling of the resilient members 158, 160 from the pouch 122.

Referring to FIG. 9K, a stripper plate 1970 is shown and includes a generally hollow cylindrical configuration with a centralized aperture 1971 defined therethrough. The central aperture 1971 is configured to both accommodate the resilient members 158, 160 and guide the suture "S". The cylindrically-shaped stripper plate 1970 also includes a rounded trailing end 1975 and a leading end 1973. A series of outwardly biased tab-like living hinges 1997 surround the outer peripheral surface 1980 of the stripper plate 1970 and are biased to self-deploy and extend outwardly from the outer peripheral surface 1980 of stripper plate 1970 when the stripper plate 1970 is deployed from the outer shaft 114 as explained in detail below. A series of slits (or flex reliefs) 1999 are defined within the outer peripheral surface 1980 of the stripper plate 1970 and are interposed between each living hinge 1997. The slits 1999 are configured to allow the stripper plate 1970 to flex inwardly for insertion into the distal end of the outer shaft 144 during assembly.

In the retracted configuration, the stripper plate 1970 is positioned with the hinges 1997 in a compressed condition within the inner periphery of the outer shaft 114 with the trailing end 1975 of stripper plate 1970 facing proximally. Both the resilient members 158, 160 and the suture(s) "S" are positioned to extend through aperture 1971. The living hinges 1997 are biased against the inner periphery of the outer shaft 114 in friction-fit engagement to hold the stripper plate 1970 within the outer shaft 114. Once stripper plate 1970 is moved to the deployed configuration, the living hinges 1997 self-deploy and extend outwardly from the outer peripheral surface 1980 of stripper plate 1970 to prevent the stripper plate 1970 from re-entering the outer shaft 114. Proximal movement of the inner shaft 116 relative to the outer shaft 114 forces a portion the trailing end 1975 of the stripper plate 1970 into the inner periphery of the outer shaft 114 such that the living hinges 1997 engage the distal end or rim of the outer shaft 114 preventing the entire stripper plate 1970 from re-entering the inner periphery of the outer shaft 114.

Once the living hinges 1997 are positioned against the outer shaft 114, further proximal movement of the inner shaft 116 causes the pouch 122 to contact the leading end 1973 of the stripper plate 1970 and uncouple the pouch 122 from the resilient members 158, 160 of the support member 128 of the inner shaft 116.

All of the aforementioned embodiments of the stripper plate described above, namely, 170, 1170, 1270, 1370, 1470, 1570, 1670, 1770, 1870 and 1970, have common attributes. For example, the main purpose of the stripper plate is to preclude the specimen bag (once deployed) from being drawn back into the outer shaft 114 by acting as a backstop to the distal end of the outer shaft 114. In some embodiments, the stripper plates serve as a fixation point for the suture "S" as the suture "S" passes though the plate and is secured to itself behind the stripper plate and/or to the stripper plate. The plate also acts to prevent the suture from being reversed though the suture aperture, e.g., aperture 1172a. In some embodiments, the stripper plate is slideable in a distal direction through the inner periphery of the outer shaft 114, but once deployed, the plate is designed to flip (in most instances) or re-orient itself to preclude reentry of the plate into the outer shaft 114.

In some embodiments, the apertures in the plate, e.g., apertures 1171 and 1172 are configured to predispose the stripper plate to re-orient itself relative to the distal end of the outer shaft 114 and the longitudinal axis "A-A" extending therethrough to facilitate uncoupling of the specimen bag 122 from the resilient members 158, 160 and retrieval of the specimen bag 122. In some embodiments, the main aperture, e.g., aperture 1171, is designed to allow the resilient members 158, 160 and the specimen bag 122 to pass therethrough. In some embodiments, one or more reliefs are disposed along the stripper plate to facilitate translation of the suture "S" therethrough and facilitate the plate re-orienting itself with respect to the longitudinal axis "A-A".

Referring again to FIG. 7, specimen retrieval device 110 includes a wedge member 185 having a grasping portion 186 and a coupling portion 187. The wedge member 185 is provided to prevent movement of the inner shaft 116 in relation to the outer shaft 114 from the partially retracted position (FIG. 8), or shipping position, to the extended position (FIG. 11) to prevent inadvertent deployment of the stripper plate 170 as will be discussed in detail below. Only stripper plate 170 will be described with respect to the embodiments of the specimen retrieval device to be described herein. However, it is contemplated that any of the above-described stripper plates 1170, 1270, 1370, 1470, 1570, 1670, 1770, 1870, and 1970 may be utilized with any of the features and embodiments described in this specification.

Referring to FIGS. 7 and 8, the grasping portion 186 of the wedge member 185 is configured for grasping by a clinician and the coupling portion 187 is configured to releasably couple the wedge member 185 to the inner shaft 116 adjacent a handle 123 of the specimen retrieval device 110. The coupling portion 187 of the wedge member 185 may couple to the inner shaft 116 via a friction or press fit, or via other suitable coupling methods and/or devices. For example, coupling portion 187 can include flexible arms which define a channel dimensioned in receive the inner shaft 116. The flexible arms flex apart to receive the inner shaft 116 within the channel and flex together to releasably secure the wedge member 185 about the inner shaft 116.

As discussed above, the wedge member 185 is configured to prevent inadvertent deployment of the stripper plate 170 from the outer shaft 114 during shipping and during preparation prior to use. Specifically, when the coupling portion 187 of the wedge member 185 is coupled to the inner shaft 116, the coupling portion 187 is configured to contact a proximal portion of the housing 112 (FIG. 7) of the specimen retrieval device 110 and the handle 122 to prevent a clinician from moving the handle 123 of the inner shaft 116 to its distal-most positon. Thus, the wedge member 185 functions as a spacer to maintain separation between the inner shaft 116 and the handle 123 to prevent movement of the inner shaft 116 in relation to the housing 112 and the outer shaft 114 to the fully extended position.

Operation of the specimen retrieval device 110 is substantially similar to that of the specimen retrieval device 10. As discussed above, the specimen retrieval device 110 is shipped with the pouch 22 in a deployed position and the inner shaft 116 in a partially retracted position as shown in FIGS. 7 and 8. Prior to use, the inner shaft 116 can be moved proximally in relation to the outer shaft 114 to move the pouch 122 into the outer shaft 114 to facilitate insertion of the outer shaft 116 through a small incision or small diameter cannula. When this occurs, the resilient members 158, 160 of the support mechanism will be drawn through the first aperture 171 of stripper plate 170 into the outer shaft 114. Thereafter, the outer shaft 114 may be positioned within a patient in a manner as described above.

In order to deploy the pouch 122 and the stripper plate 170 from the outer shaft 114, the wedge member 185 is removed from the inner shaft 116 by pulling the grasping portion 186 of the wedge member 185 to separate the coupling portion 187 from the inner shaft 116. Thereafter, the inner shaft 116 is moved to the extended position (see FIG. 10) in contact with the housing 112. The inner shaft 116 can be moved to the fully extended position because the wedge member 185 is removed and does not obstruct movement of the handle 133. When this occurs, a distal end of the inner shaft 116 engages and pushes the stripper plate 170 from the distal end of the outer shaft 114. As discussed above with regard to device 10 shown in FIGS. 1-6, this movement of the inner shaft 114 causes the pouch 122 to be released by the retention member 26 (FIG. 2A). Once the stripper plate 170 is deployed from the outer shaft 114, a clinician can move the inner shaft 116 proximally in relation to the outer shaft 114. Unlike the pouch 22 of the specimen retrieval device 10, however, the pouch 122 of the specimen retrieval device 110 which is configured to contact the distal end of the outer shaft 116, the pouch 122 of retrieval device 110 is configured to contact the leading end 175 of the stripper plate 170 to separate the pouch 122 from the resilient members 158, 160 of the specimen retrieval device 110. Once the pouch 122 has been separated from the inner shaft 116, a clinician may proceed in a manner as described above with respect to the specimen retrieval device 10 to cinch or close the pouch 122.

Figure 12A:
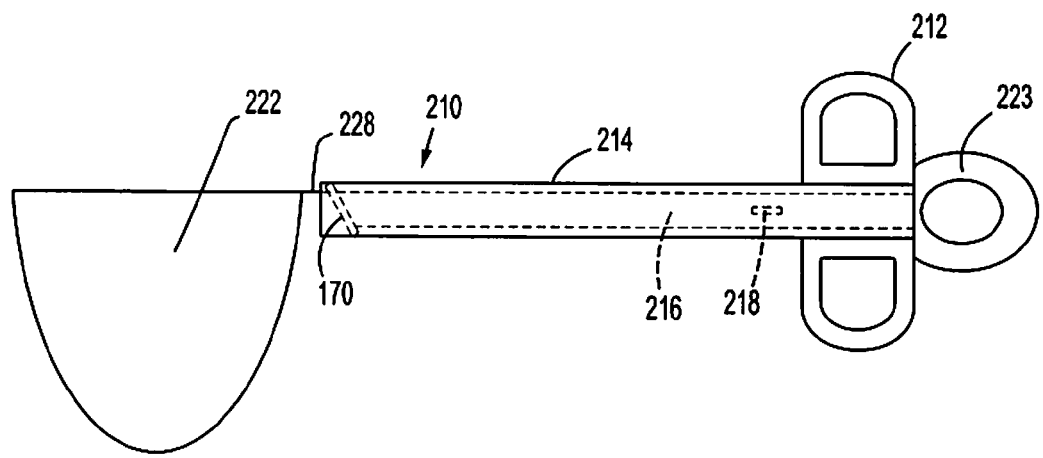
FIG. 12A is a schematic view of a specimen retrieval device according to another embodiment of the present disclosure with the pouch in a partially retracted position.
Figure 12B:
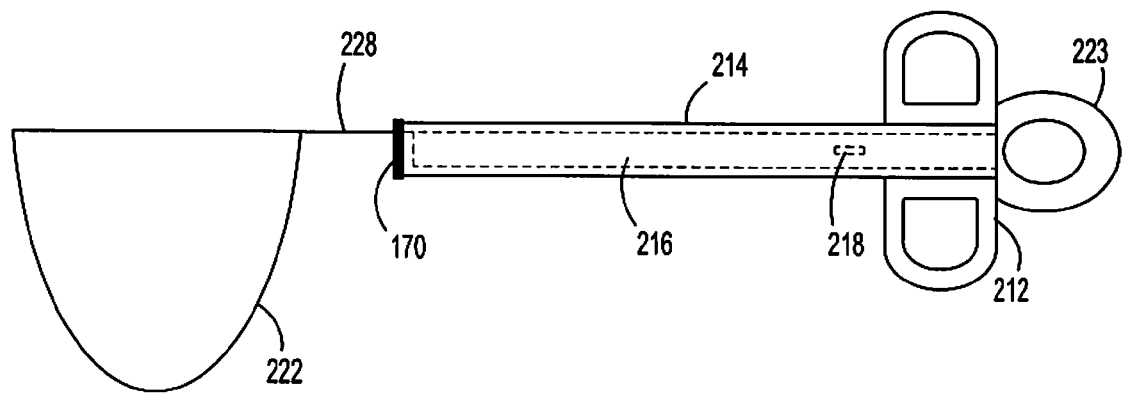
FIG. 12B is a schematic view of the specimen retrieval device shown in FIG. 12A with an inner shaft in a fully extended configuration and the pouch and stripper plate of the specimen retrieval device deployed.

Referring to FIGS. 12A-12B, a specimen retrieval device 210 according to another embodiment of the present disclosure is illustrated. The specimen retrieval device 210 functions similar to the specimen retrieval devices 10, 110 and includes, inter alia, the retention member 26 and sled 24 assembly described with respect to FIGS. 1-6. Accordingly, only the functional features that are unique to the specimen retrieval device 210 are described herein.

The specimen retrieval device 210 includes a housing 212 and an outer shaft 214 that extends distally from the housing 212. As with each of the embodiments disclosed herein, the housing 212 and the outer shaft 214 can be formed integrally as a single unit. The housing 212 and the outer shaft 214 together define a longitudinal bore 214a which extends along a longitudinal axis. The housing 212 and/or the outer shaft 214 include one or more blocking members in the form of detents 218 that are positioned on an interior wall defining the longitudinal bore 214a. As can be appreciated, more or less detents 218 may be positioned on the interior wall of the housing 212 as will be discussed in further detail below.

An inner shaft 216 is movably positioned within the longitudinal bore 214 of the housing 212 and the outer shaft 214. The inner shaft 216 is configured to function in a manner similar to that of inner shaft 16. The inner shaft 216 supports a support mechanism 228 at its distal end which includes a pair of resilient members (not explicitly shown) similar to support mechanism 28 (FIG. 1) described above. The resilient members are configured to support a pouch 222 which is substantially similar to pouch 22 and pouch 122 described above.

The inner shaft 216 is movable from a partially retracted position (FIG. 12A), the shipping position of the retrieval device 210, in which the pouch 222 is deployed and the stripper plate 170 is positioned within the distal end of the outer shaft 214, to a fully retracted position, and thereafter, to an extended position (FIG. 12B) in which the pouch 222 and the stripper plate 170 are both deployed. The specimen retrieval device 210 further includes an actuation mechanism which functions to enlarge the effective stroke of the inner shaft 216 upon retraction of the inner shaft 216 from the partially retracted position (FIG. 12A) to a fully retracted position (FIG. 17) to facilitate movement of the inner shaft 216 from the fully retracted position to the extended position (FIG. 12B) as discussed in further detail below.

Figure 13:
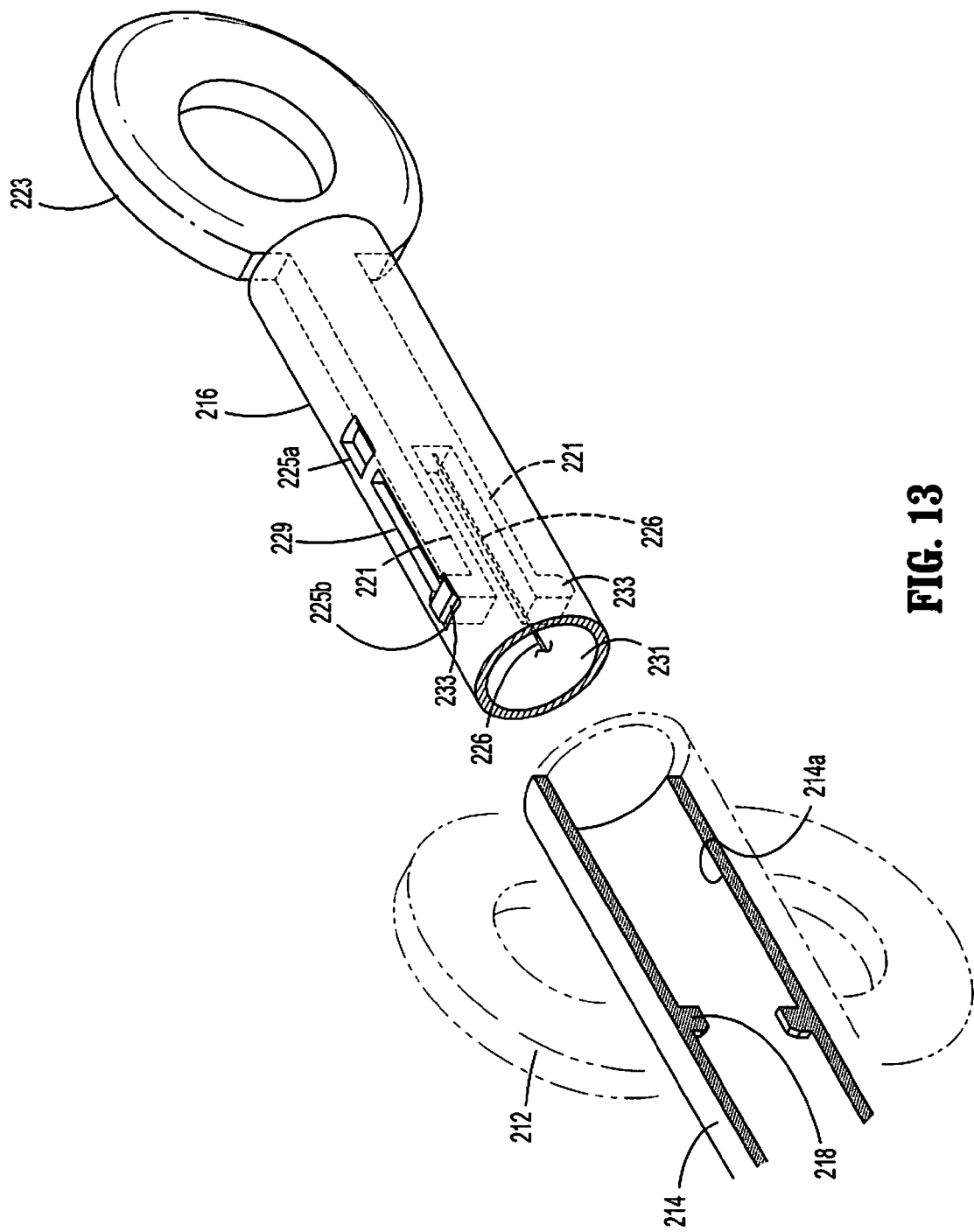
FIG. 13 is a perspective view of a proximal end of the specimen retrieval device shown in FIGS. 12A and 12B illustrating the proximal end of the outer shaft separated from the inner shaft with the actuation device engaged with the distal apertures of the inner shaft.

Referring also to FIGS. 13-15, the inner shaft 216 includes one or more proximal apertures 225a and one or more distal apertures 225b of suitable configuration. For illustrative purposes, two proximal apertures 225a and two distal apertures 225b are illustrated. Each of the proximal and distal apertures 225a, 225b are longitudinally spaced along the inner shaft 216 and positioned to receive a respective protrusion 233 as discussed in further detail below. A groove 229 of suitable configuration is defined along the inner shaft 216 between each of the proximal and distal apertures 225a and 225b and communicates with each respective distal aperture 225b. The grooves 229 have a width which is dimensioned to receive a respective detent 218 but is smaller than the width of protrusions 233 and apertures 225a and 225b. For illustrative purposes, two grooves 229 are shown in the figures (See, e.g., FIG. 16). The groove 229 is configured to slidably receive the detent 218 of the housing 212 when the inner shaft 216 is moved in relation to the outer shaft 214 and the housing 212 from the partially retracted position (FIG. 12A) to the fully retracted position (FIG. 17). As can be appreciated, a second groove 229 is only required where two apertures 225a and two detents 218 are provided.

Continuing with reference to FIGS. 13-15, the inner shaft 216 includes a handle or actuation device 223 that is capable of being repositioned on the inner shaft 216 to change the effective stroke of the inner shaft 216. The handle 223 includes one or more arms 221 that extend distally from the handle 223 and into a cavity 231 (FIG. 13) provided at a proximal end of the inner shaft 216 when the handle 223 is coupled to the inner shaft 216 (see FIG. 13 for example). The arms 221 arc flexible and include a protrusion 233 (detent, barb or the like) at a distal end thereof that is configured to be received in one of the proximal and distal apertures 225a, 225b of the inner shaft 216 to connect the handle 223 to the inner shaft 223. When the handle 223 is connected to the inner shaft 216 via the distal apertures 225a, the handle 223 is positioned to engage the proximal end of the housing 212 to limit advancement of the inner shaft 216 to the partially retracted position (FIG. 12A). In contrast, when the handle 223 is connected to the inner shaft 216 via the proximal apertures 225b, the stroke of the inner shaft 216 is lengthened to facilitate movement of the inner shaft 216 to the extended position as shown in FIG. 12B as will be discussed in further detail below.

As discussed above with respect to the specimen retrieval devices 10 and 110, the surgical retrieval device 210 includes a retention member 26 and sled 24 assembly such as discussed above. The assembly functions as described above and will not be shown or discussed in further detail herein. Alternatively, the retention member 24 described above can be connected directly to handle 223 by a retention member connector 226 (FIGS. 13 and 14). The retention member 26 functions as described above to releasably couple the pouch 222 to the support mechanism 228 of the inner shaft 216 but is actuated by the connector 226 rather than the sled 24. More specifically, a proximal portion of the retention member connector 226 is operably coupled directly to the handle 223 of the inner shaft 216 via one or more suitable coupling methods, and the distal end of the connector 226 is connected to the retention member 26. One or more additional grooves (not shown) are provided along the inner shaft 216 which are configured to slidably receive the retention member connector 226 so that the retention member connector 226 can be moved in relation to the inner shaft 216 along a longitudinal axis defined through the outer shaft 214 when the handle 223 moves in relation to the inner shaft 216 as described in further detail below.

A stripper plate (FIGS. 12A and 12B) may also be provided on the specimen retrieval device 210 which is configured and functions as described above with respect to any of the stripper plates disclosed herein, e.g., stripper plate 170. Further, a cinch puller, e.g., cinch puller 62, and suture "S" may be provided to facilitate closure of the pouch 222 as described above.

Referring to FIGS. 12A and 16, the specimen retrieval device 210 may be shipped with the pouch 222 in a deployed configuration (FIG. 12A) and the inner shaft 216 in the partially retracted position. In this position, the protrusion 233 of the arms 221 are received within the distal apertures 225b (FIG. 16) and the handle 223 is positioned in abutment with the housing 212 to prevent further distal translation of the inner shaft 216 in relation to the housing 212 and the outer shaft 214. As shown in FIG. 12A, with the handle 223 in this position, the pouch 222 will be deployed from the outer shaft 214 and the stripper plate 170 will remain within the distal end of the outer shaft 214.

Prior to use of the specimen retrieval device 210, the inner shaft 216 is moved proximally in relation to the outer shaft 214 (FIG. 13) to position the pouch 222 within the outer shaft 214 so that the outer shaft 214 may be inserted through a natural or manmade orifice and positioned adjacent target tissue within a body cavity. Referring to FIGS. 16A-17, as the handle 223 is pulled proximally to move the inner shaft 216 toward the fully retracted position, the detents 218 formed along an inner wall of the housing 212 (or outer shaft 214) move along the grooves 229 and into engagement with the protrusions 233 formed on arms 221 of the handle 223 (FIG. 16A). When the detents engage the protrusions 233, a tapered cam 218*a* surface formed on the detents 218 deforms the arms 221 outwardly to remove the protrusions from the distal apertures 225*a* (FIG. 16B). When the protrusions 233 become disengaged from the apertures 225*a*, the handle 223 moves proximally independently of the inner shaft 216 until the protrusions 233 snap into the proximal protrusions 225*b* (FIG. 17). As discussed above, the handle 223 may be directly connected to the retention member 26 (FIG. 2A) by the connector 226. As such, when the handle 223 moves proximally independently of the inner shaft 216, the retention member 26 will be withdrawn from engagement with the protrusions 34 on the inner shaft 216 to disengage the retention member 26 from the protrusions 34.

Figure 18:
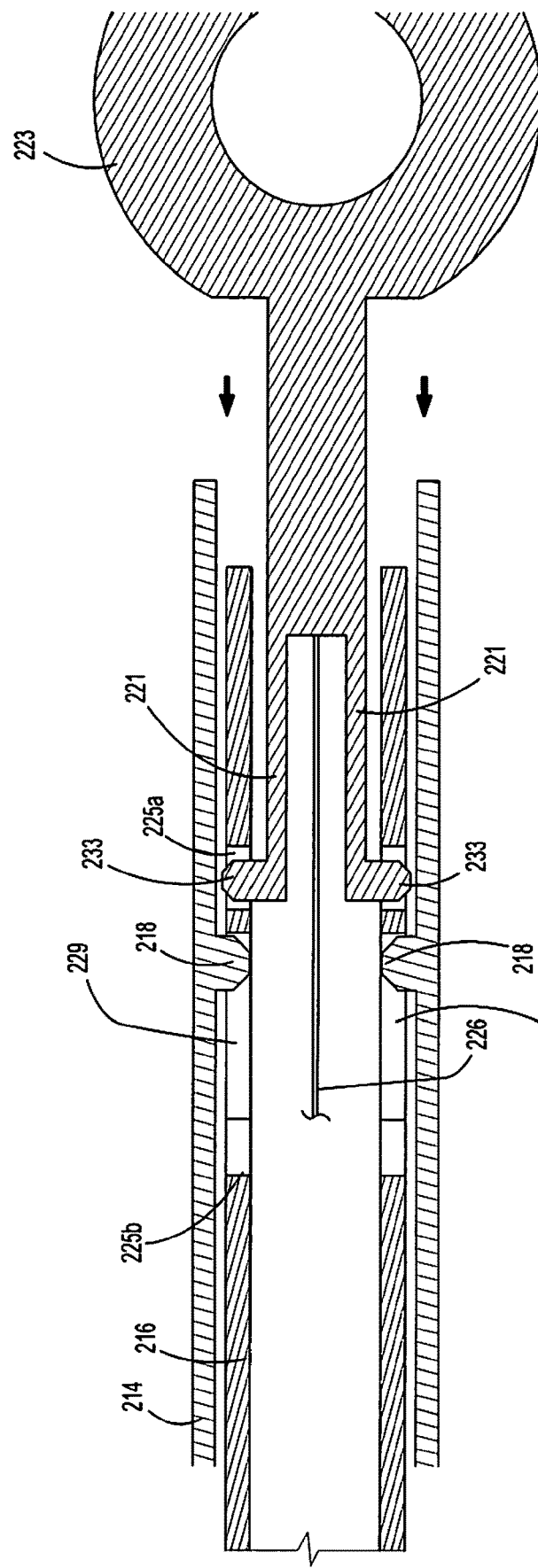
FIG. 18 is a cross-sectional view of the proximal end of the specimen retrieval device with the protrusions of the actuation shaft received in the proximal apertures of the inner shaft as the inner shaft and actuation device are moved from the fully retracted position towards the extended position.

Referring to FIGS. 12B and 18, once the protrusions 233 are received in the proximal openings 225*a* of the inner shaft 216 and the handle 223 is recoupled to the inner shaft 216, the handle 223 can be moved proximally to advance the inner shaft 216 to the fully extended position to deploy the pouch 222 and the stripper plate, e.g., stripper plate 170 from the outer shaft 214 (FIG. 12B). As illustrated in FIGS. 16 and 17, the reconfiguration of the handle 223 in relation to the inner shaft 216 increases the effective stroke of the inner shaft 216 by a distance equal to $D_2 - D_1$ to facilitate deployment of both the pouch 222 and the stripper plate 170.

After the specimen retrieval pouch 210 is deployed and the surgical procedure has been completed, the pouch can be disengaged from the inner shaft 216 as discussed above. More specifically, the handle 223 can be retracted to retract the inner shaft 216 to the fully retracted position. As the inner shaft is withdrawn into the outer shaft 214, the pouch 222 moves into contact with the stripper plate, e.g., stripper plate 170, and the stripper plate abuts the distal end of the outer shaft 214. As discussed above, this engagement causes the pouch 222 to slide off the resilient members of the support mechanism 228 as the inner shaft 216 is moved further proximally. Once the pouch 222 is uncoupled from the support mechanism 228, a cinch puller (e.g., similar to the cinch puller 62) may be actuated to close the pouch 222 in a manner as described above.

With reference to FIGS. 19-21, a specimen retrieval device 310 according to an alternate embodiment of the present disclosure is illustrated. In the embodiment illustrated in FIGS. 19-21, an actuation device in the form of a removable handle 323 is removably coupled to the inner shaft 316 of the specimen retrieval device 310. The handle 323 serves a dual purpose. More specifically, handle 323 is operable for moving an inner shaft 316 in relation to an outer shaft 314 and also for cinching an open end of a pouch 322 supported on a support mechanism 328 of the specimen retrieval device 310. The distal portion of handle 323 may fit within the outer shaft 314 or, alternatively, may abut the outer shaft 314.

Specimen retrieval device 310 includes a release mechanism 390 pivotably disposed on a top surface 393 of the handle 323. Specifically, the release mechanism 390 can be overmolded to the handle 323 such that a living hinge 390 is formed between the top surface 393 of the handle 323 and the release mechanism 390. Alternately, other hinge mechanisms may be used to secure the release mechanism 390 to the handle 323. The release mechanism 390 is movable from a locked configuration (FIG. 20) in which the handle 323 is coupled to the inner shaft 316 to an unlocked configuration (FIG. 21) in which the handle 323 is uncoupled from the inner shaft 316. A proximal end 390*a* of the release mechanism 390 is depressible for disengaging a mechanical interface, e.g., a detent 394, of the release mechanism 390 from a corresponding mechanical interface, e.g., an indent 391, on the inner shaft 316 (FIGS. 20 and 21) to uncouple the handle 323 from the inner shaft 316. The release mechanism 390 can be biased or naturally resilient to urge the release mechanism 390 to the locked configuration. A cinch, e.g., a suture "S," has a proximal end coupled to a distal end of the handle 323 and a distal end positioned about an opening in the pouch 322 to facilitate closure of the pouch opening as described above.

In use, with the release mechanism 390 in the locked configuration, the inner shaft 316 may be moved in a relation to the outer shaft 314 to move the pouch 322 within the outer shaft 314 so that the outer shaft 314 may be inserted through a natural or manmade orifice on a patient and positioned adjacent target tissue.

Thereafter, the specimen retrieval device 310 may be configured to uncouple the pouch 322 from the resilient members of the support mechanism of the specimen retrieval device 310 as described above with respect to the specimen retrieval devices 10, 110, 210.

Once the pouch is uncoupled from the inner shaft 316, the inner shaft 316 can be retracted to facilitate separation of the pouch 322 from the support mechanism 328 using, for example, a stripper plate or the distal end of the outer shaft 314. Next, the release mechanism 390 may be depressed to release the handle 323 from the inner shaft 316. Thereafter, the handle 323 can be moved proximally in relation to the device 310 to cinch the pouch 322. As can be appreciated, a specimen retrieval device 310 that utilizes the release mechanism 390 makes the specimen retrieval device 310 more intuitive to use.

Figure 22:
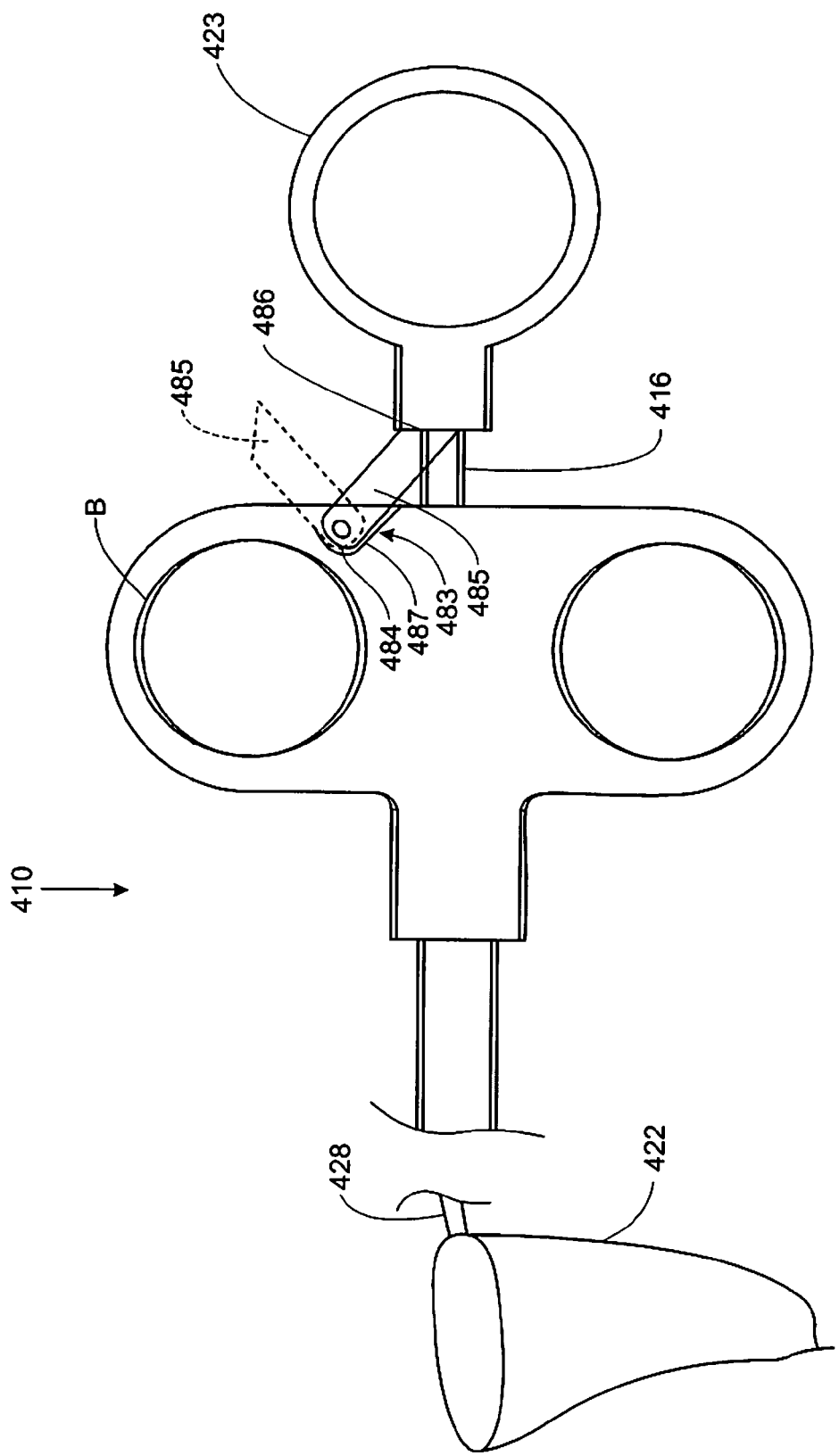
FIG. 22 is a schematic view of a proximal end of a specimen retrieval device including a locking a member in accordance with another embodiment of the present disclosure.

Referring to FIG. 22, a specimen retrieval device 410 according to another embodiment of the present disclosure is illustrated. This embodiment utilizes a lock-out device in the form of a lever 485 that is configured to replace the wedge members 185, 285 of specimen retrieval devices 110 and 210 described above. Specifically, the lever 485 is movable from a locked configuration in which the lever 485 is positioned to engage the handle 423 to prevent engagement between a proximal end of a housing 412 and a distal end of handle 423 of an inner shaft 416, to an unlocked configuration (shown in phantom) in which the lever 485 is spaced from the handle 423 to allow engagement between the proximal end of the housing 412 and the handle 423. The lever 485 prevents the inner shaft 416 from moving to the extended position in the locked configuration to prevent inadvertent deployment of the stripper plate, e.g., stripper plate 170 (FIG. 8).

In the embodiment illustrated in FIG. 22, the lever 485 has a generally elongated configuration and is disposed adjacent a proximal end of the housing 412. The lever 485 includes a leading end 484 that is pivotably coupled to the housing 412 via a pivot pin and a trailing end 486 that is configured to engage a distal end of the handle 423. The lever 485 is seated within a notch 483 that is defined within an exterior of the housing 412. The notch 483 is defined by at least one wall 487 that is configured to contact at least a portion of the lever 485 and maintain the lever 485 in the locked configuration. The specimen retrieval device 410 may be utilized in a manner as described above with respect to the specimen retrieval devices that utilize one of the aforementioned wedge members 185, 285, e.g. the specimen retrieval devices 110, 210.

FIGS. 23A-23C illustrate portions of a specimen retrieval device 1000 according to another embodiment of the present disclosure. As described above, it is advantageous to ship a specimen pouch in a deployed condition to reduce the likelihood of memory wrinkles being formed on the pouch. The specimen retrieval device 1000 may be shipped for use with pouch in an unfolded and deployed configuration, outside of the outer shaft 1014, with a stripper plate 170 (FIG. 7) positioned within an outer shaft 1014. In order to prevent initial deployment of the stripper plate 170 during shipping, the inner shaft 1016 must be prevented from moving distally until the specimen pouch is pulled (via proximal movement of the inner shaft 1016) within the outer shaft 1014 to facilitate positioning of the outer shaft 1014 of the specimen retrieval device 1000 through a small body incision or cannula into a body cavity.

In order to accomplish this, the specimen retrieval device 1000 includes structure that serves a similar function to the above described wedge members 185 and 285 and lockout device 485, i.e., to prevent inadvertent distal advancement of the inner shaft 1016 relative to the housing 1012 and, thus, prevent premature deployment of the stripper plate 170 from the outer shaft 1014.

In one particular embodiment, the specimen retrieval device 1000 includes a housing 1012 and an outer shaft 1014 that extends distally from the housing 1012. See FIG. 23A. The outer shaft 1014 defines a longitudinal bore 1011 therethrough. An inner shaft 1016 (FIG. 23A) is selectively translatable through the bore 1011. Inner shaft 1016 may be tubular or be shaped to limit relative rotation within the outer shaft 1014. For example, the inner and outer shafts can include one or more flats to prevent relative rotation. A cam lock 1080 (FIG. 23B) is supported on the housing 1012 and acts to prevent initial distal translation of the inner shaft 1016 relative to the housing 1012 (and prevent unintended deployment of the stripper plate 170) until the clinician retracts the inner shaft 1016 to position the specimen pouch, e.g., 22, 122, within the outer shaft 1014 to facilitate insertion of the specimen device 1000 through a trocar as described above.

Referring to FIGS. 23A-23C, cam lock 1080 is mounted to housing 1012 about a pivot 1024 and is rotatable from a first position wherein the cam lock 1080 acts to prevent initial distal translation of the inner shaft 1016 to a second position wherein the inner shaft 1016 is distally translatable within the outer shaft 1014 to deploy the specimen pouch 22, 122 and stripper plate 170 as described above with to respect to the embodiments of FIGS. 7-22. Cam lock 1080 is generally C-shaped and includes first and second portions 1081a and 1081b, respectively. First portion 1081a is configured to engage corresponding interfaces 1022a and 1022b disposed on an upper surface 1016a of the outer periphery of inner shaft 1016 to prevent accidental deployment of the stripper plate 170 as described in more detail below. Once rotated, second portion 1081b of cam lock 1080 is configured to lock the cam lock 1080 in the second position as described in more detail below.

Portions 1081a and 1081b of cam lock 1080 include outer surfaces 1084 and 1082 and inner surfaces 1086 and 1087, respectively. The inner surfaces 1086 and 1087 mutually define an aperture 1085 therebetween. First portion 1081a is configured to extend in a first plane positioned above the upper surface 1016a of the inner shaft 1016, while second portion 1081b is offset from the first plane and configured to extend in a second plane below the first plane as viewed in FIG. 23A to engage a side 1016b of shaft 1016. Engagement between second portion 1081b and side 1016b of shaft 1016 prevents rotation of cam lock 1080 in a clockwise direction as viewed in FIG. 23A to prevent translation of the inner shaft 1016 towards an extended position.

In an embodiment, cam lock 1080 defines an elongated pivot hole 1083 that is configured to receive a pivot 1024 disposed atop housing 1012. In one embodiment, pivot 1024 is also elongated and is dimensioned such that as cam lock 1080 rotates from the first position to the second position, a portion of the cam lock 1080 defining the elongated pivot hole 1083 engages the pivot 1024 such that the pivot 1024 locks against an inner periphery 1083a of pivot hole 1083 in the second position (See FIG. 23C). It is envisioned that either the pivot hole 1083 or the pivot 1024 may be shaped to effect frictional engagement between the cam lock 1080 and the pivot member 1024 to retain the cam lock 1080 in the second position.

As mentioned above, the specimen retrieval device 1000 may be shipped with the inner shaft 1016 in a partially retracted position such that the pouch 22, 122 is in an unfolded and deployed configuration, and the stripper plate 170 is in an undeployed condition positioned within the outer shaft 1014. In order to prevent inadvertent initial deployment of the stripper plate 170, the inner shaft 1016 is prevented from being advanced to the extended position from the partially retracted position by the cam lock 1080. More particularly, the inner surface 1086 of first portion 1081a of the cam lock 1080 is initially positioned to abut interface 1022a on inner shaft 1016 when the inner shaft 1016 is in the partially retracted position (FIG. 23A). Since the cam lock 1080 can only rotate in a counter-clockwise direction because of engagement between second portion 1081b of cam lock 1080 with side 1016b of inner shaft 1016, distal advancement of the inner shaft 1016 is prevented. In use, a clinician unpacks the specimen retrieval device 1000 from its shipping container and readies the device 1000 for insertion into a surgical cavity by pulling the inner shaft 1016 proximally to translate the inner shaft 1016 within the outer shaft 1014. As discussed above, interface 1022a prevents movement of the inner shaft 1016 from the partially retracted position (FIG. 23A) directly to the extended position. Proximal translation of the inner shaft 1016 within the outer shaft 1014 withdraws the specimen pouch 22, 122 into a distal end of the outer shaft 1016. The clinician draws the inner shaft 1016 proximally until interface 1022b of inner shaft 1016 engages the outer surface 1084 of first portion 1081a. When the interface 1022b engages first portion 1081a of cam lock 1080, the interface 1022b forces the cam lock 1080 to rotate in a counter-clockwise direction. Continued withdrawal of shaft 1016 forces cam lock 1080 to rotate and lock in the second position (approximately 90 degrees of rotation) (FIG. 23C) wherein the first portion 1081a is generally parallel to inner shaft 1016. As mentioned above, the second portion 1081b (and/or the configuration of the pivot 1024 within the pivot hole 1083) may be used to lock the cam lock 1080 in the second position. Other mechanisms (explained below with respect to FIGS. 24A-24D) may also be utilized to accomplish this purpose.

Once the specimen pouch 22, 122 is withdrawn into the outer shaft 1014 and the cam lock 1080 is locked in the second position, the clinician may selectively advance the inner shaft 1016 to deploy the specimen pouch 22, 122 within an operating cavity of a patient without interference from the cam lock 1080. More particularly, in the second position, the cam lock 1080 does not interfere with or engage interferences 1022a or 1022b on the inner shaft 1016 during distal translation of the inner shaft 1016. Distal advancement of the inner shaft 1016 to the extended position will also deploy the stripper plate, e.g., stripper plate 170. See FIGS. 7-11. Indicia or tactile elements (not shown) may be included on the specimen retrieval device 1000 to provide feedback to the clinician that the inner shaft 1016 is positioned to effect deployment of the specimen pouch 22, 122.

As best shown in FIGS. 24A-24D, one or more mechanisms may be utilized to lock the cam lock 1080 in the second position. For example, the cam lock 1080 may be configured such that in the second position of the cam lock 1080, the second portion 1081b engages a spring 1032 disposed proximate the side 1016b of inner shaft 1016 and locks the cam lock 1080 in the second position. FIGS. 24A-24D detail this sequence of operation.

Figure 24A:
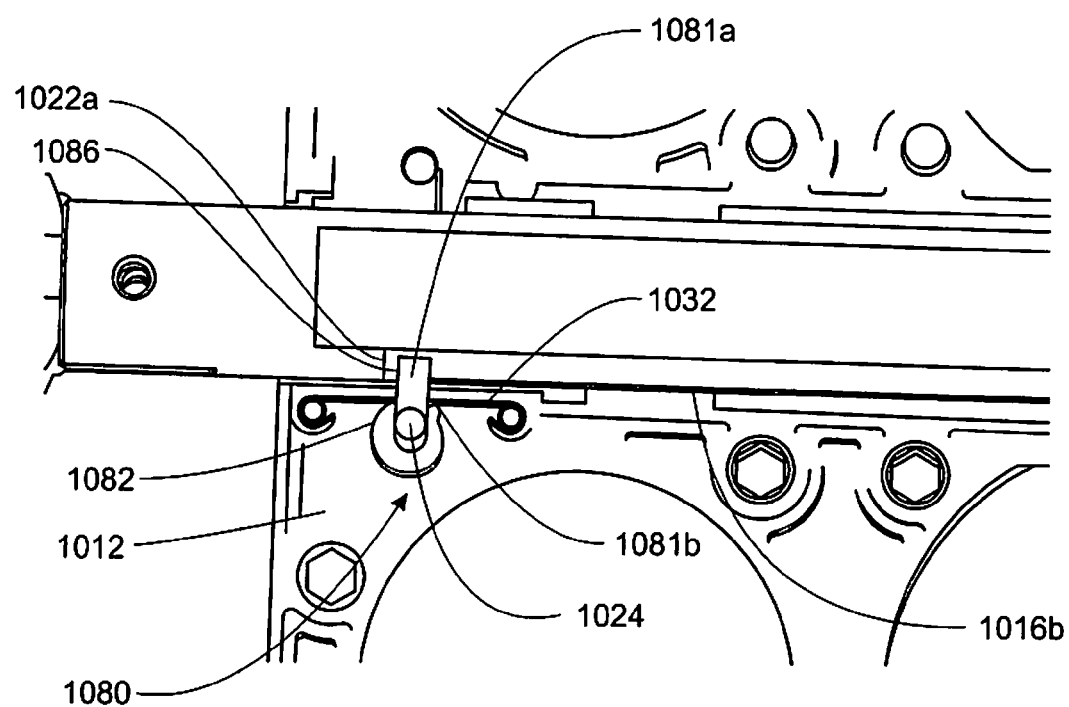
FIGS. 24A-24D are schematic views showing the sequence of operation as the inner shaft is translated proximally and the cam lock moves from the first position for preventing distal advancement of the inner shaft relative the housing to the second position allowing distal advancement of the inner shaft relative to the housing.

FIG. 24A shows an alternate embodiment of the cam lock 1080 with the inner shaft partially retracted in a shipping position. In this position, the cam lock 1080 is prevented from rotating in a clockwise direction by virtue of the geometry of the housing 1012, one or more pins, ribs or other known locking mechanisms, not shown. In this position, the first portion 1081a of cam lock 1080 extends into a track 1023 defined in a side wall of inner shaft 1016 such that an interface 1022a defined at one end of track 1023 is positioned to abut the first portion 1081a of the cam lock 1080 to prevent distal translation of the inner shaft 1016. An outer surface 1082 of the second portion 1081b of the cam lock 1080 is positioned to contact the spring 1032. The cam lock 1080 is free to rotate in a counter-clockwise direction. As discussed in further detail below, spring 1032 may be configured to provide the clinician with tactile feedback as the second portion 1081b of the cam lock 1080 is rotated over the spring 1032 upon proximal translation of the inner shaft 1016.

Figure 24B:
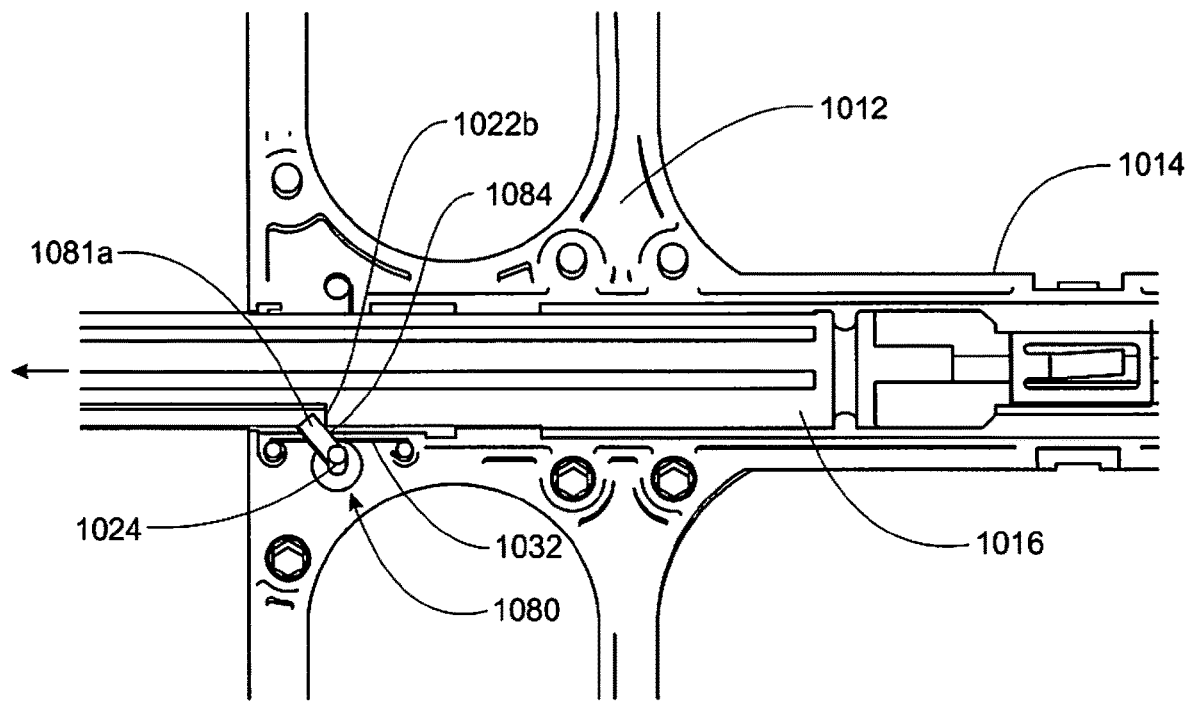

FIG. 24B shows the specimen retrieval device 1000 near full retraction of the inner shaft 1016 with respect to the housing 1012. More particularly, as inner shaft 1016 nears full retraction and the specimen retrieval pouch 22, 122 is withdrawn into the outer shaft 1014, interface 1022b defined at the other end of the track 1023 engages the outer surface 1084 of first portion 1081a of the cam lock 1080 and forces the cam lock 1080 to rotate in a counter clock-wise direction as viewed in FIG. 24B toward a second unlocked position. As cam lock 1080 is rotated toward the second position, the second portion 1081b of the cam lock 1080 is rotated against the bias of the spring 1032 to provide a tactile feedback to the clinician that the inner shaft 1016 is nearing full retraction and the specimen pouch 22, 122 is almost fully positioned within the outer shaft 1014.

Figure 24C:
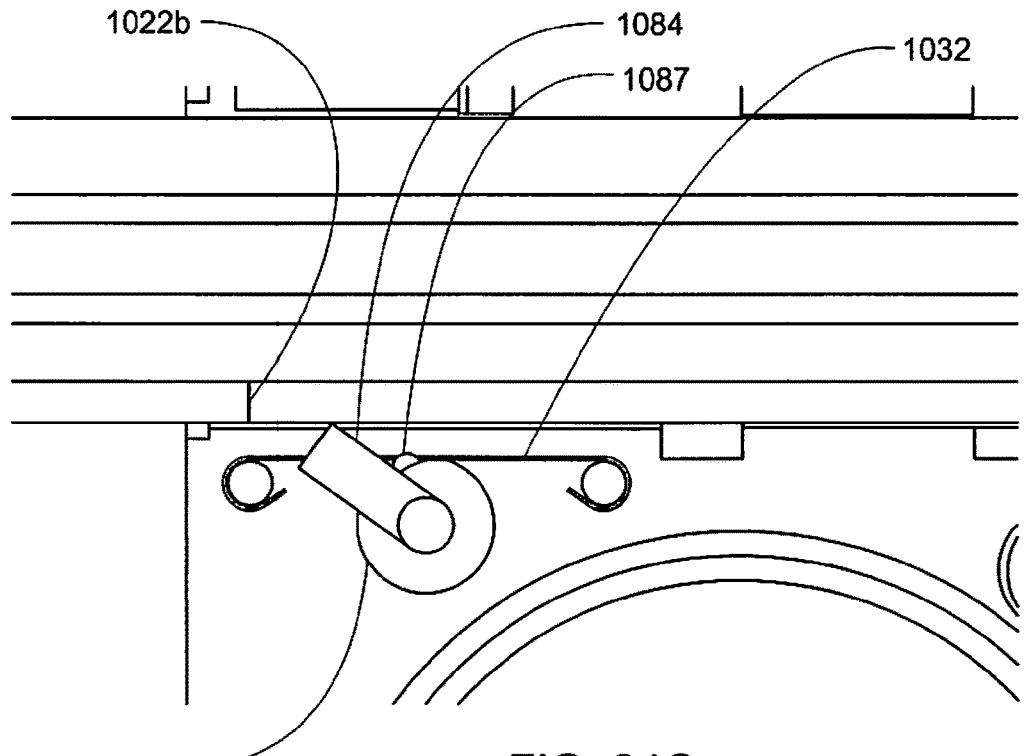
Figure 24D:
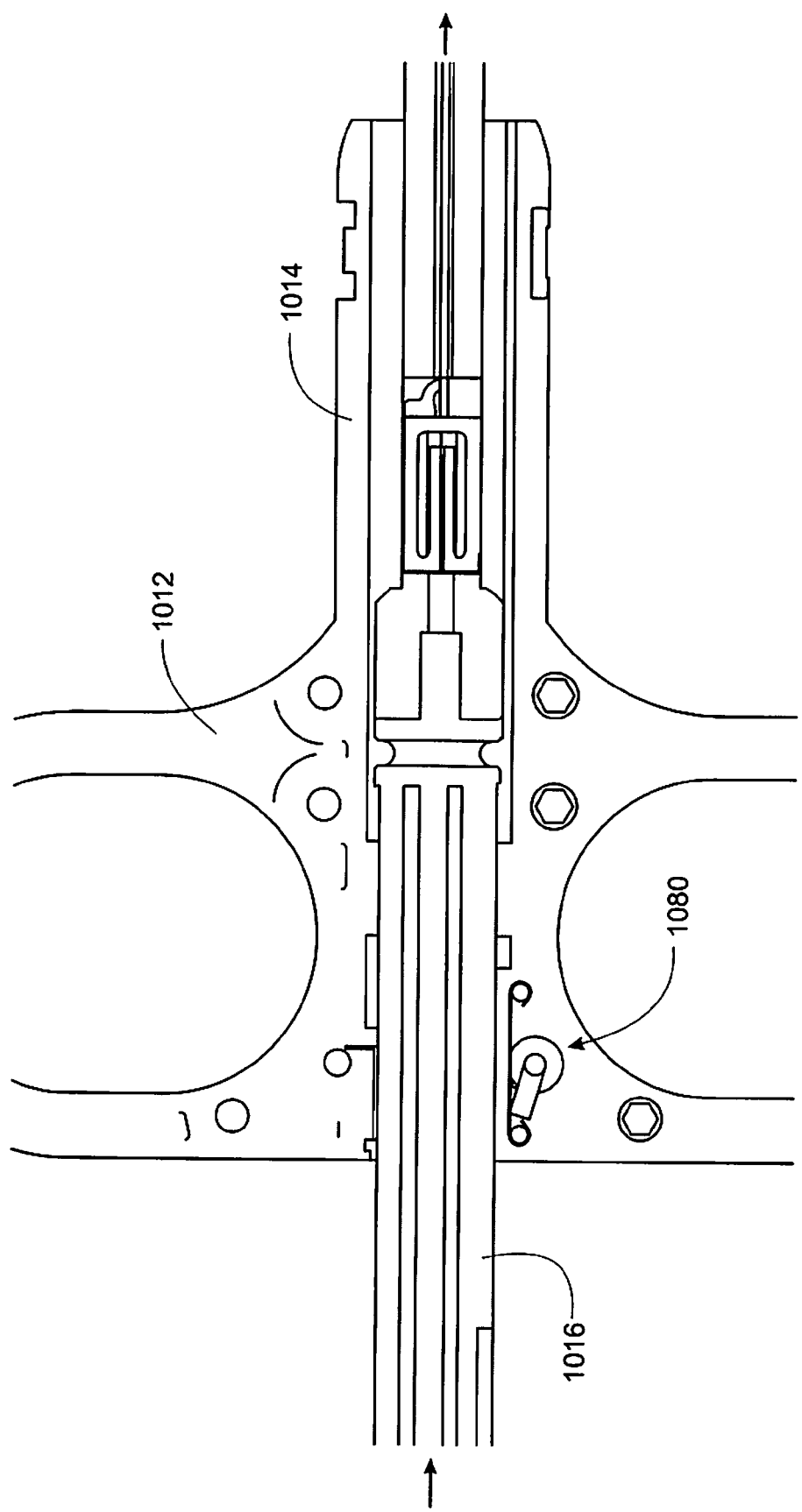

As best shown in FIGS. 24C-24D, once the inner shaft 1016 is fully retracted within the outer shaft 1014 (FIG. 24C), an extension 1087 of the second portion 1081b rotates over and locks against the spring 1032 to lock the cam lock 1080 in the second position. In the second position, the cam lock 1080 is positioned outside of the track 1023 to allow unimpeded distal translation of the inner shaft 1016 to the extended position with respect to the housing 1012 to effect deployment of the specimen pouch 22, 122 and stripper plate 170 as discussed above.

FIGS. 25A-27 show another embodiment of a specimen retrieval device 2000 having a shipping lockout in the form of a removable shipping wedge 2100 which prevents movement of an inner shaft 2016 from a partially retracted or shipping position to an extended position. Specimen retrieval device 2000 is similar to the specimen retrieval devices detailed above and, accordingly, only those features unique to specimen retrieval device 2000 are described herein. Specifically, a clinician must initially retract the inner shaft 2016 from a partially retracted or shipping position to a fully retracted position to release a locking device and move the pouch 22, 122 into the outer shaft 2014 before the inner shaft 2016 can be advanced to the extended position. Thereafter, the outer shaft 2014 may be positioned within a patient in a manner as described above and the specimen pouch 22, 122 and stripper plate, e.g., 170 (FIGS. 7-11) can be fully deployed.

FIG. 25A shows an exploded, perspective view of the specimen retrieval device 2000 having a housing 2012 and inner and outer shafts 2016, 2014, respectively, that are selectively translatable relative to one another to withdraw and deploy the specimen retrieval pouch 22, 122. A groove or slot 2018 is defined within the housing 2012 and is configured to receive the removable shipping wedge 2100 therein. An alignment channel 2017 is defined in the inner shaft 2016 and is dimensioned to align with slot 2018 when the inner shaft 2016 is fully retracted and specimen pouch 22, 122 is withdrawn into outer shaft 2014 as explained in more detail below. A flexible finger 2019 is disposed on the inner shaft 2016 proximal to channel 2017 and is configured to prevent advancement of the inner shaft 2016 from the fully retracted position towards the extended position until the shipping wedge 2100 is removed from the specimen retrieval device 2000, as explained in more detail below. In addition, the inner shaft 2016 includes a stop surface 2022 that is positioned to engage the shipping wedge 2100 when the inner shaft 2016 is in the partially retracted or shipping position to prevent movement of the inner shaft 2016 from the partially retracted position to the extended position prior to removal of the shipping wedge 2100.

Referring to FIG. 25B, shipping wedge 2100 includes a handle 2120 having an elongated shaft 2116 that extends therefrom. The shaft 2116 includes an interface 2110 at a distal end thereof that is configured to be received within slot 2018 in housing 2012. Interface 2110 includes opposing surfaces 2112 and 2114 that define a notch 2011 which slidably receives the inner shaft 2016 while allowing translation of the inner shaft 2016 therethrough.

Figure 26:
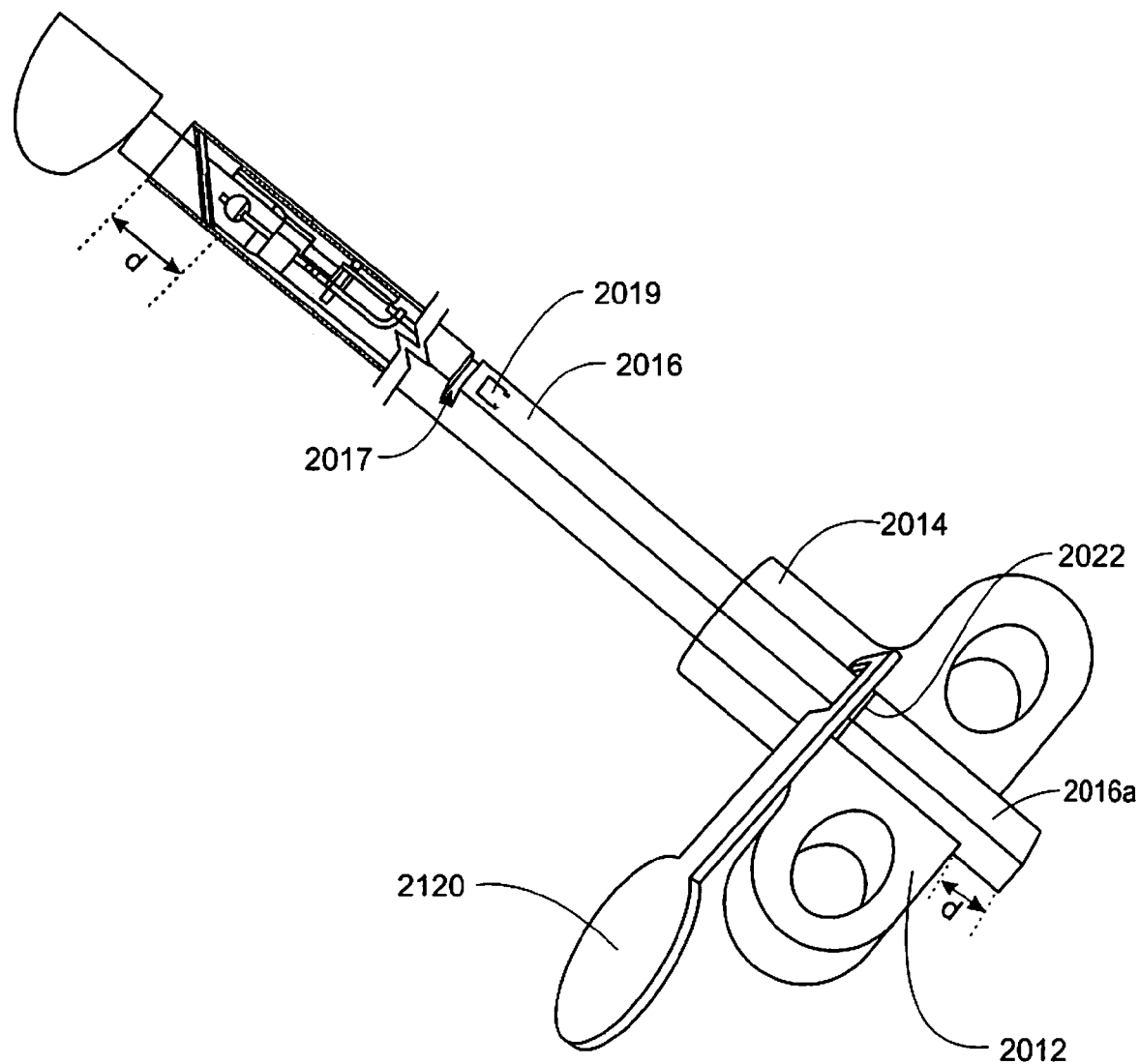
FIGS. 26-27 are schematic views of the specimen retrieval device shown in FIG. 25A with the removable shipping wedge positioned to prevent initial distal translation of an inner shaft relative to a housing.

As best shown in FIG. 26, in the partially retracted position of the inner shaft 2016 or the shipping position of the specimen retrieval device 2000, the shipping wedge 2100 is positioned through the slot 2018 within the housing 2012 such that the inner shaft 2016 (or a portion thereof) is received through the notch 2111 (FIG. 25B). The shipping wedge 2100 is prevented from being removed laterally from slot 2018 by virtue of the inter-engagement of surfaces 2112, 2114 of interface 2110 with the sides inner shaft 2016. The stop surface 2022 is disposed on a proximal end of inner shaft 2016 and configured to engage the inner shaft 2016 to prevent initial distal translation of the inner shaft 2016 past the shipping wedge 2100 (FIG. 25A). This prevents the distal end of the inner shaft from deploying the stripper plate, e.g., the stripper plate 170, from the outer shaft 2014. When the inner shaft 2016 is positioned in the partially retracted position such that the stop surface 2022 engages the shipping wedge 2100, further distal advancement of the inner shaft 2016 is prevented. In this position, the inner shaft 2016 is positioned a distance "d" from the extended position. Distance "d" represents the dwell distance required for deploying the stripper plate 170 from the outer shaft 2014. It is envisioned that the dwell distance "d" can be greater than the distance the stripper plate 170 is positioned within the distal end of the outer shaft 2014. Once the shipping wedge 2100 is removed (as explained below), the inner shaft 2016 may be translated distally to its extended position to deploy the stripper plate 170 from the outer shaft 2014 (See FIGS. 7-10).

Figure 27:
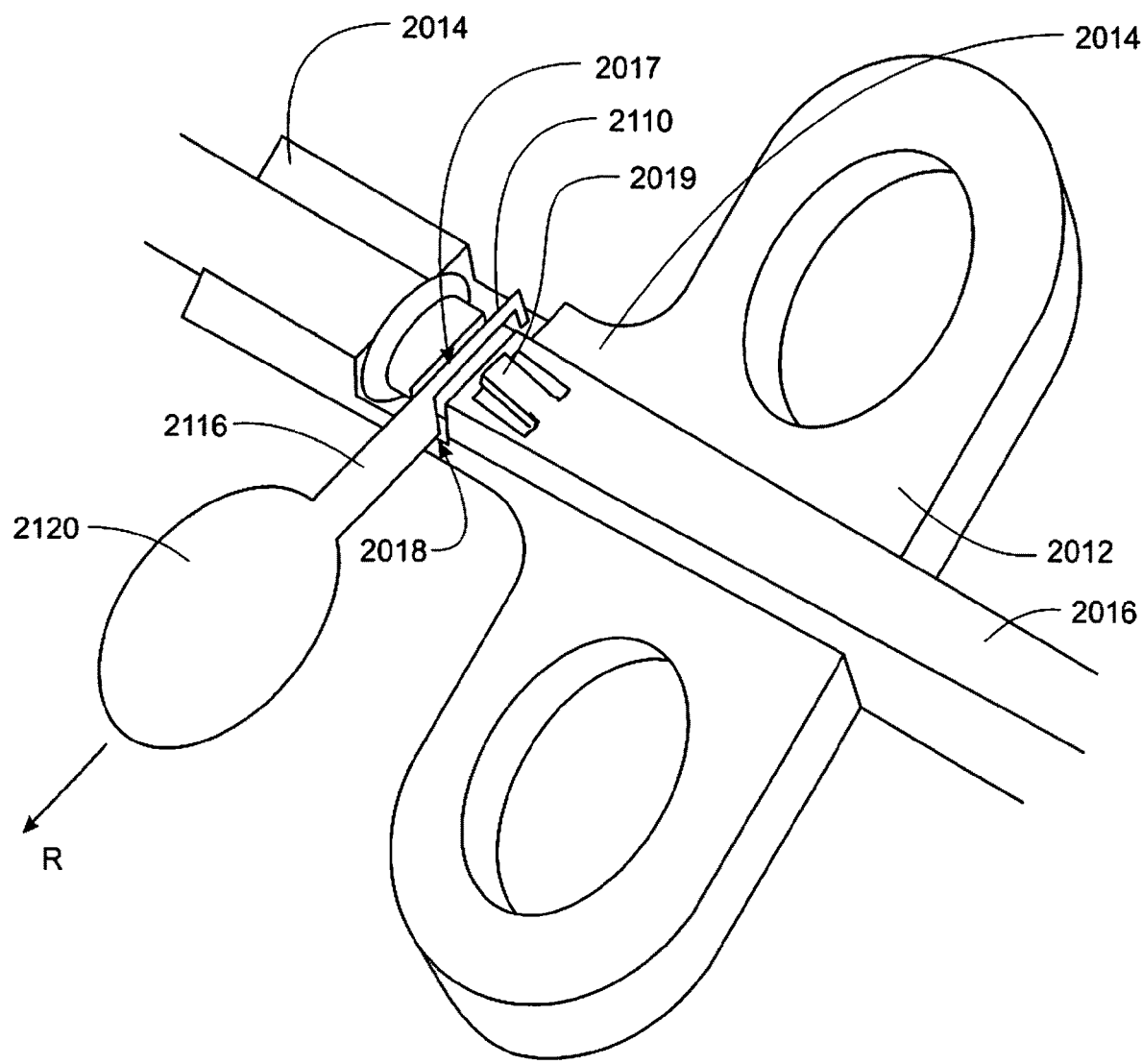

Prior to use of the specimen retrieval device 2000, the clinician retracts the inner shaft 2016 by withdrawing the handle 2023 to withdraw the specimen pouch 22, 122 into the distal end of the outer shaft 2016. The clinician continues to draw the inner shaft 2016 proximally until the flexible finger 2019 (FIG. 25A) disposed on inner shaft 2016 is deflected by, and withdrawn beneath the interface 2110 of the shipping wedge 2100 and moves to a proximal side thereof as shown in FIG. 27. Various known audible or tactile elements may be utilized to provide feedback to the clinician to indicate that the inner shaft 2016 is fully retracted and the specimen pouch 22, 122 has been adequately withdrawn into the outer shaft 2014. For example, the clinician may feel or hear a snap as the flexible finger 2019 is released after it passes beneath the shipping wedge 2100.

As best shown in FIG. 27, when the flexible finger 2019 passes under interface 2110 of the shipping wedge 2100, the inner shaft 2016 is in the fully retracted position and the specimen pouch 22, 122 is positioned within the outer shaft 2014. At this point, distal movement of the inner shaft 2016 is prevented by the flexible finger 2019 which is positioned to engage the shipping wedge 2100 until the shipping wedge 2100 is removed.

When the inner shaft 2016 is in the fully retracted position, the channel 2017 defined by the inner shaft 2016 aligns with corresponding slot 2018 defined within housing 2012 to facilitate removal of the shipping wedge 2100 from the specimen retrieval device 2000.

In order to remove the shipping wedge 2100 from the device 2000, a clinician pulls the handle 2120 of the shipping wedge 2100 transversally with respect to the inner shaft 2016 in the direction "R" (FIG. 27) to withdraw the shipping wedge 2100 through the channel 2017 in the inner shaft 2016 and the slot 2018 in housing 2012 and release the interface 2110 from inner shaft 2016. With the shipping wedge removed, the inner shaft 2016 is free to be translated distally to deploy the specimen pouch 22, 122 (See FIG. 27).

A method of preventing inadvertent deployment of a specimen pouch 22, 122 of a specimen retrieval device 2000 is also disclosed and includes providing a specimen retrieval device 2000 having a housing 2012 with a slot 2018, an inner shaft 2016 and an outer shaft 2014. The outer shaft 2014 defines a bore 2011 extending therethrough that is connected to the housing 2012. An inner shaft 2016 is disposed within the bore 2011 and is translatable therethrough, the inner shaft including a support mechanism 28 (See FIG. 6) configured to releasably support the specimen pouch 22, 122 at a distal end thereof and a flange 2022 disposed at a proximal end. A removable shipping wedge 2100 includes an interface 2110 at a distal end thereof that is configured to receive the inner shaft 2016 while allowing translation of the inner shaft 2016 therethrough. A stop surface 2022 is supported on a proximal end of the inner shaft 2016 and is positioned to engage the shipping wedge 2100 to prevent full distal translation of the inner shaft 2016 to the extended position from a partially retracted position or the shipping position.

The method also includes inserting the interface 2110 through the slot 2018 in the housing 2012 such that the interface 2110 engages the stop surface 2022 to prevent full distal translation of the inner shaft 2016 relative to the housing 2012.

A method of deploying a specimen pouch 22, 122 of a specimen retrieval device 2000 is also disclosed and includes providing a specimen retrieval device 2000 including a housing 2012 having a slot 2018 defined therein and an outer shaft 2014 connected to the housing 2012 and extending distally therefrom. The outer shaft 2014 includes a bore 2011 extending therethrough. An inner shaft 2016 is included and is disposed within the bore 2011 of the outer shaft 2014 and is translatable therethrough, the inner shaft 2016 including a channel 2017 defined at a distal end that extends across an outer periphery of the inner shaft 2016. The inner shaft 2016 also includes a support mechanism 28 (See FIG. 6) configured to releasably support a specimen pouch 22, 122 at a distal end thereof and a flexible finger 2019 disposed on the inner shaft 2016 proximal to the channel 2017. A stop surface 2022 is disposed at a proximal-most portion 2016a of the inner shaft 2016.

A removable shipping wedge is also provided and includes an interface 2110 at a distal end thereof configured to encompass the outer periphery of the inner shaft 2016 while allowing translation of the inner shaft 2016 therethrough.

The method also includes: inserting the interface 2110 through the slot 2018 in the housing 2012 such that the interface 2110 engages the stop surface 2022 at the proximal-most potion 2016a of the inner shaft 2016 to prevent initial distal translation of the inner shaft 2016 relative to the housing 2012; proximally translating the inner shaft 2016 relative to the housing 2012 from a first position wherein the stop surface 2022 engages the interface 2110 of the shipping wedge 2100 to prevent distal translation of the inner shaft 2016 to a second position wherein the interface 2110 of the shipping wedge 2100 aligns with the channel 2017 of the inner shaft 2016; removing the shipping wedge 2100 through the slot 2018 in the housing 2012; and distally translating the inner shaft 2016 relative to the housing 2012 to deploy the specimen pouch 22, 122.

The proximally translating step of the method may also include biasing the flexible finger 2019 of the inner shaft 2016 past the interface 2110 of the shipping wedge 2100 to position the flexible finger 2019 on a proximal side of the interface when the inner shaft 2016 is translated to the second or fully retracted position; and preventing distal movement of the inner shaft 2016 relative to the housing 2012 until the shipping wedge 2100 is removed.

Referring to FIGS. 28-33, a specimen retrieval device 3000 according to another embodiment of the present disclosure is illustrated. As mentioned above, it is advantageous to ship the specimen pouch 22, 122 in a deployed condition to reduce the likelihood of memory wrinkles being formed on pouch 22, 122. Similar to the specimen retrieval devices described above, the pouch 22, 122 is shipped in an unfolded and deployed configuration, positioned externally of the outer shaft 3014 with the stripper plate, e.g., stripper plate 170 (FIG. 7) positioned within the outer shaft 3014.

As with the other specimen retrieval devices described above, the inner shaft 3016 is prevented from moving distally until the specimen pouch 22, 122 is first withdrawn into the outer shaft 3014 to facilitate positioning the specimen retrieval device 3000 within a surgical cavity through a small incision or cannula. Thereafter, the outer shaft 3014 may be positioned within a patient in a manner as described above and the specimen pouch 22, 122 subsequently deployed.

Figure 28:
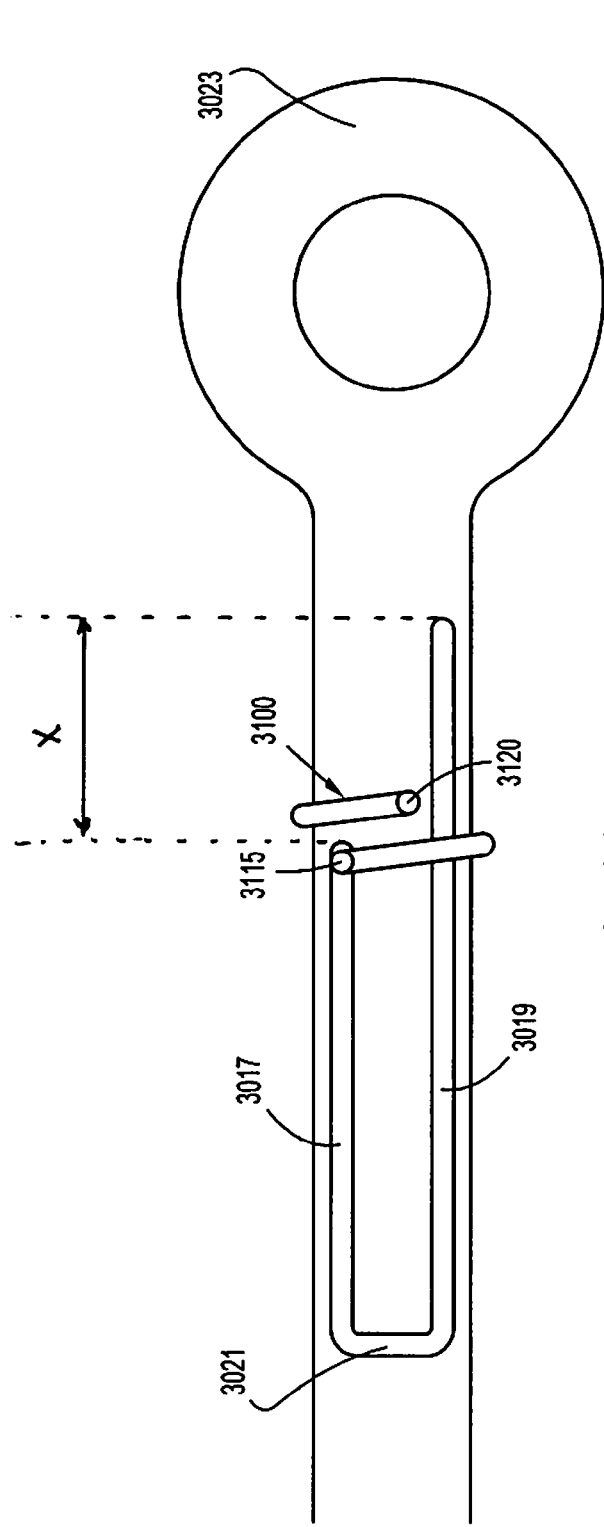
FIG. 28 is a side view of an inner shaft and torsion spring of a specimen retrieval device according to another embodiment of the present disclosure with the inner shaft in a partially retracted position.

FIG. 28 shows specimen retrieval device 3000 which includes a housing 3012 that supports inner and outer shafts 3016 and 3014, respectively. Inner shaft 3016 is selectively translatable through outer shaft 3014 and defines a longitudinally extending cam slot 3018 having first and second portions 3017 and 3019. A torsion spring 3100 has a first end 3120 fixedly engaged to a first end of the housing 3012 (or the outer shaft 3014) and a second end 3115 dimensioned to ride within cam slot 3018 as detailed below. The torsion spring 3100 is in tension to urge end 3115 of torsion spring 3100 towards end 3120 of the torsion spring 3100. However, inner shaft 3016 is rotatably fixed within the outer shaft 3014 by respective geometries of the outer and inner shafts 3014, 3016 to prevent rotation of the inner shaft 3016 in relation to the housing 3012. A channel 3021 is defined between the distal ends of the first and second portions 3017 and 3019 of the cam slot 3018 and is configured to facilitate translation of the second end 3115 of the torsion spring 3100 from the first portion 3017 to the second portion 3019 of cam slot 3018 as discussed in further detail below.

First portion 3017 of cam slot 3018 is shorter than the second portion 3019 of the cam slot 3018 by a distance "X". The distance "X" represents the dwell distance required for deploying the stripper plate, e.g., the stripper plate 170, from the outer shaft 3014 as will be discussed in further detail below. It is envisioned that the dwell distance "X" can be greater than the distance the stripper plate is positioned within the outer shaft 3014 such that the inner shaft 3016 may be translated distally to or beyond the dwell distance "X" to deploy the stripper plate 170 from the outer shaft 3014 (See FIGS. 7-10).

Figure 29:
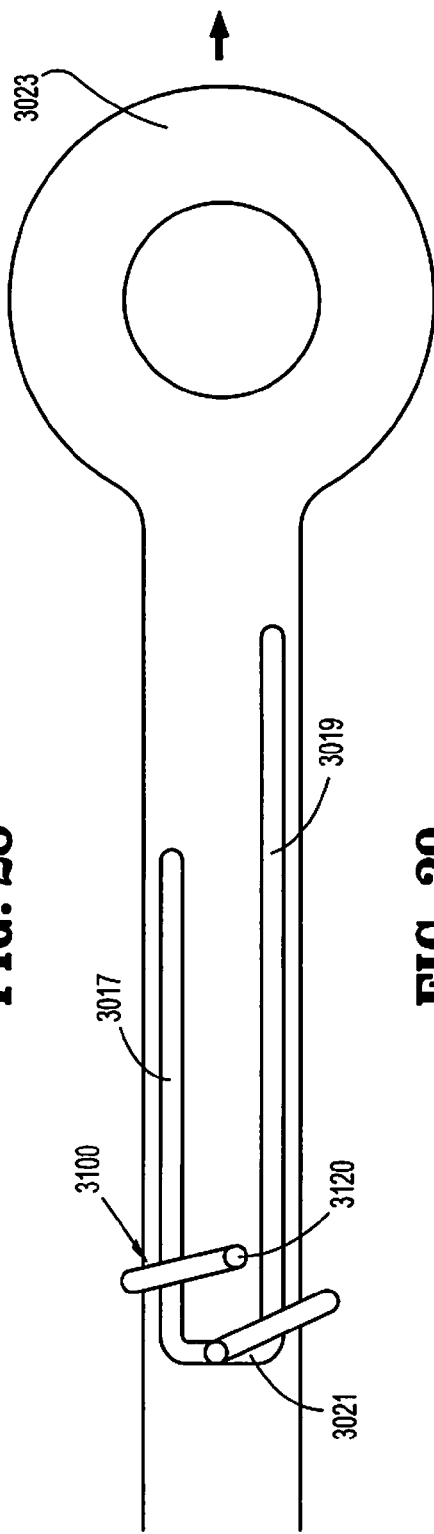
FIG. 29 is a side view of the inner shaft and torsion spring shown in FIG. 28 after the inner shaft has been moved to the fully retracted position as the torsion spring transitions from a first portion of a cam slot to a second portion of a cam slot.

As best shown in FIGS. 28 and 29 prior to use, a clinician unpacks the specimen retrieval device 3000 from its shipping container and readies the device 3000 for insertion within a surgical cavity. The end 3115 of the torsion spring 3100 is initially positioned adjacent the proximal end of the first portion 3017 of cam slot 3018 with the inner shaft 3016 in a partially retracted position. Engagement of the end 3115 of the torsion spring 3100 with a proximal end wall of the first portion 3017 of cam slot 3018 prevents further distal movement of the inner shaft 3016 with respect to the housing 3012 to the extended position to prevent inadvertent deployment of the specimen pouch 22, 122 and the stripper plate, e.g., stripper plate 170, from the outer shaft 3014.

Figure 30:
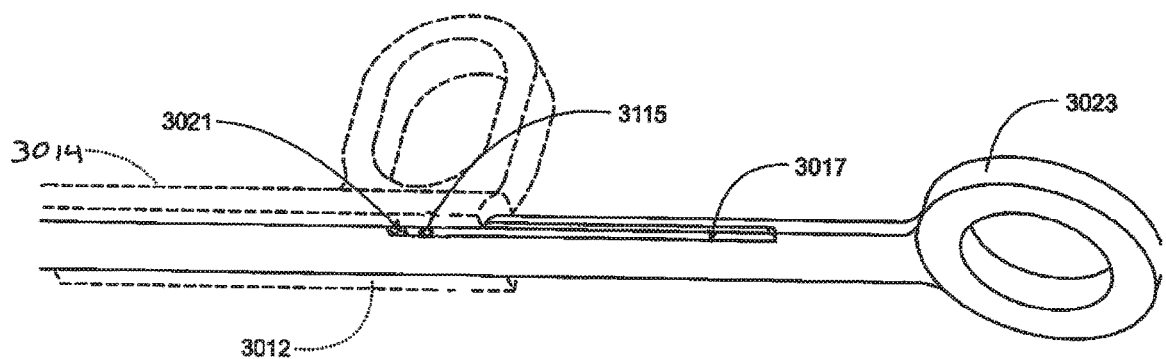
FIGS. 30-33 are schematic views of a specimen retrieval device according to another embodiment of the present disclosure having a housing, inner shaft and torsion spring that is configured to prevent initial distal translation of the inner shaft relative to the housing.
Figure 31:
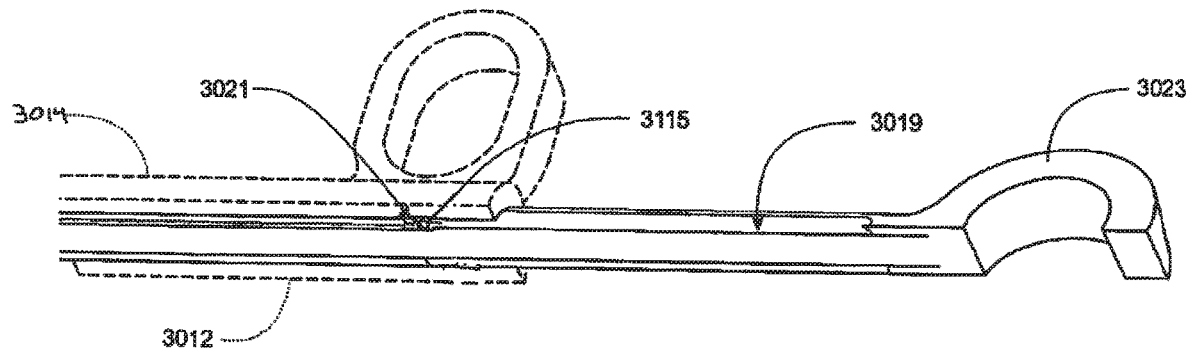
Figure 32:
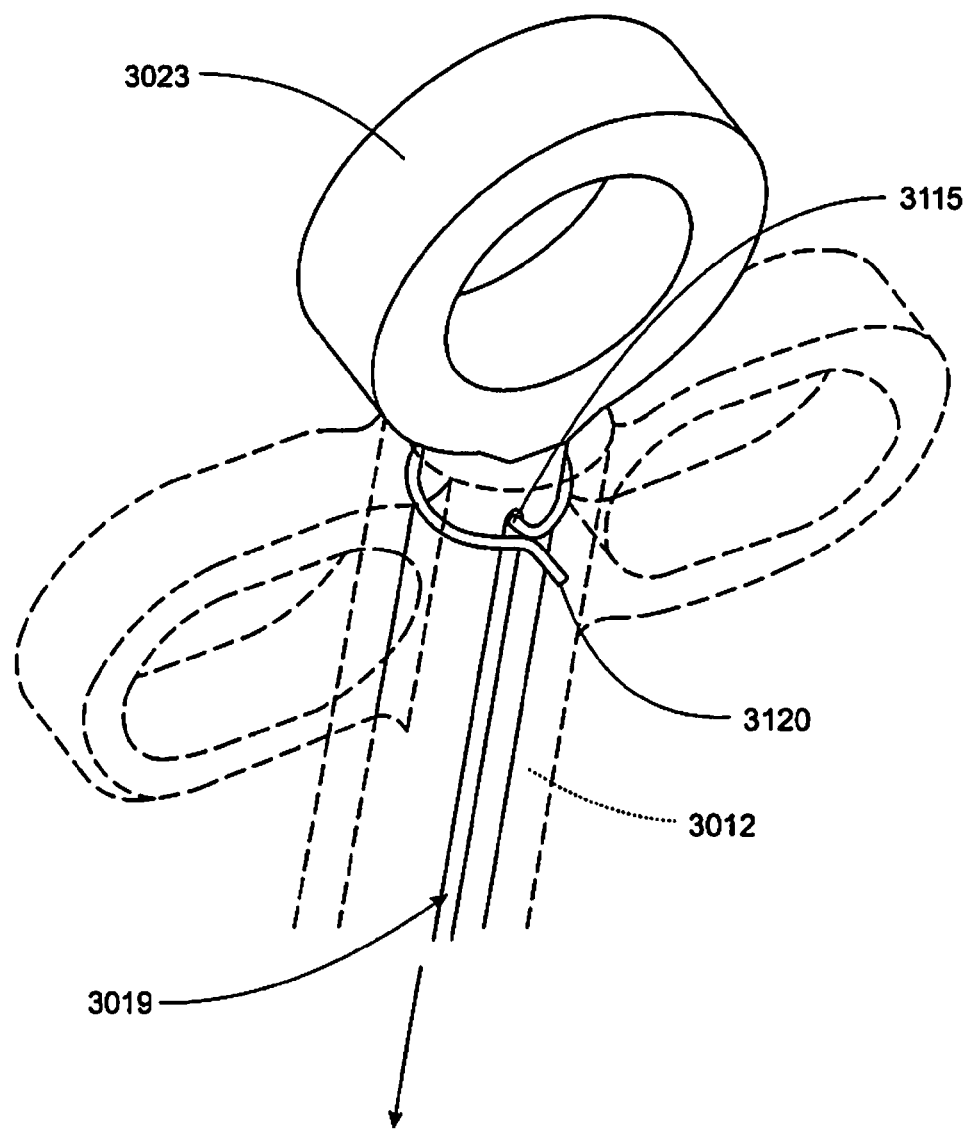
Figure 33:
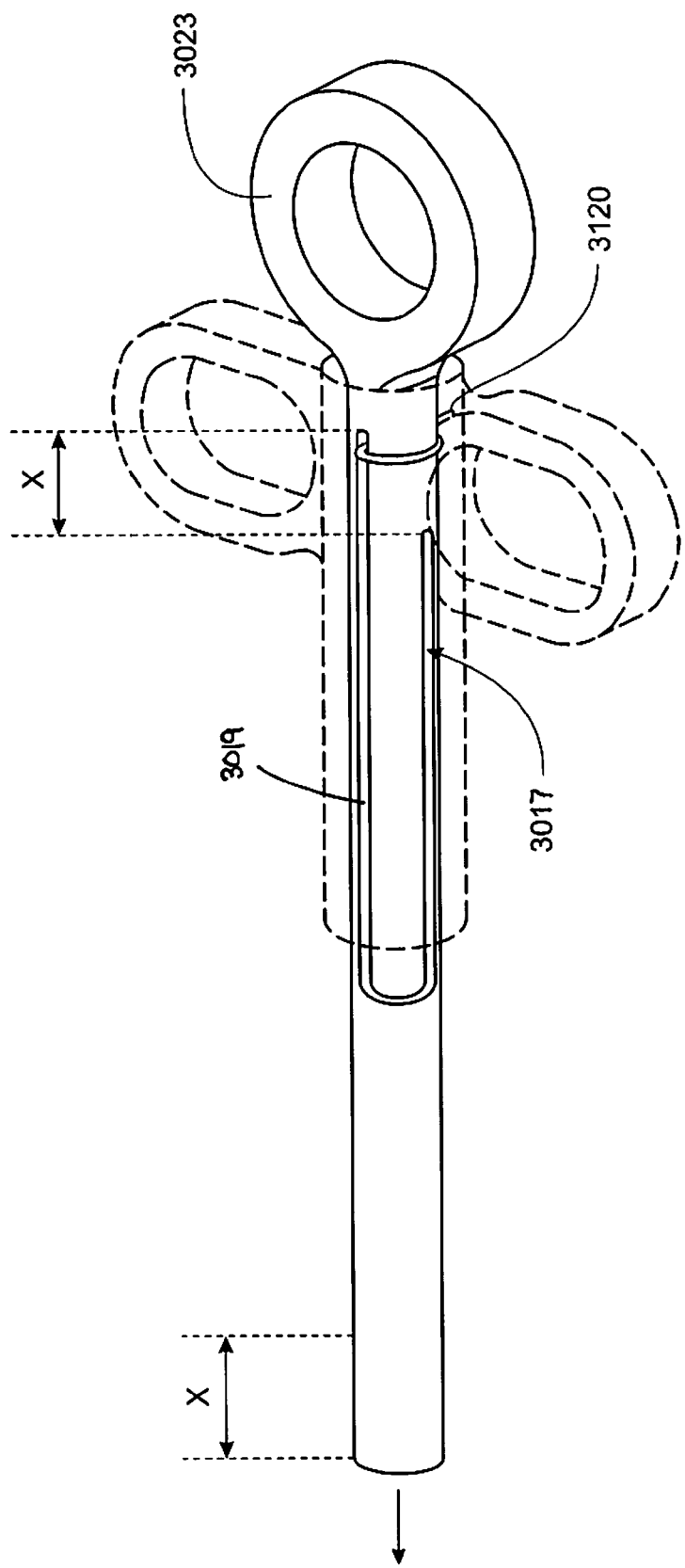
Figure 34A:
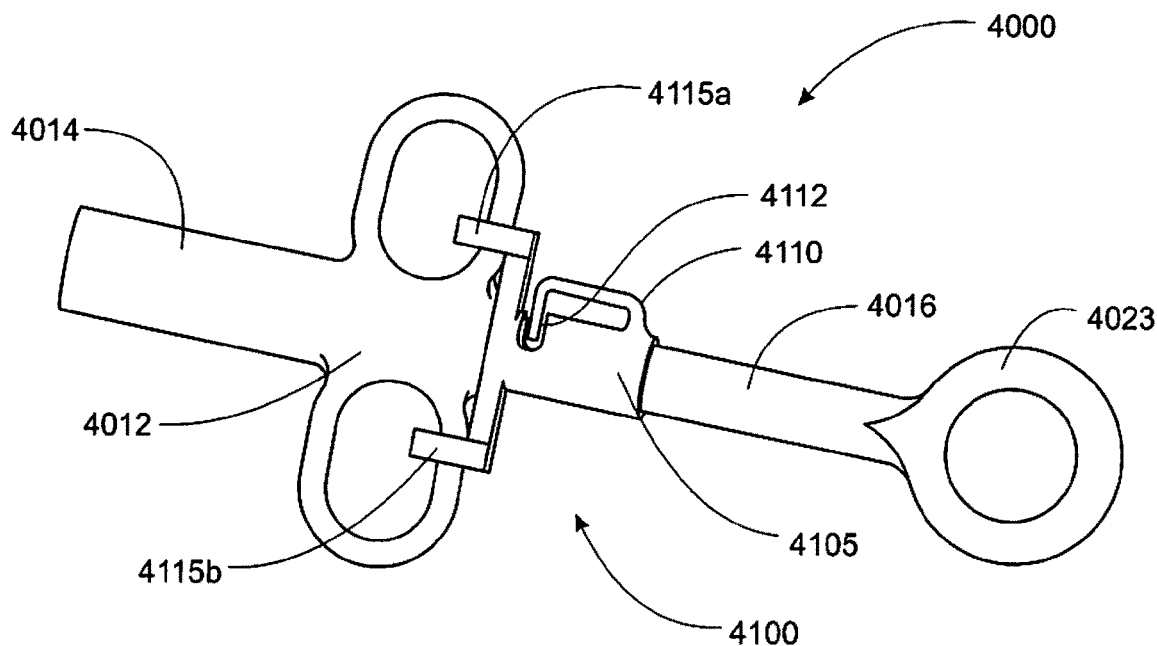
FIGS. 34A-38 are schematic views of a specimen retrieval device according to another embodiment of the present disclosure having a removable shipping wedge to prevent initial distal translation of an inner shaft relative to a housing.
Figure 34B:
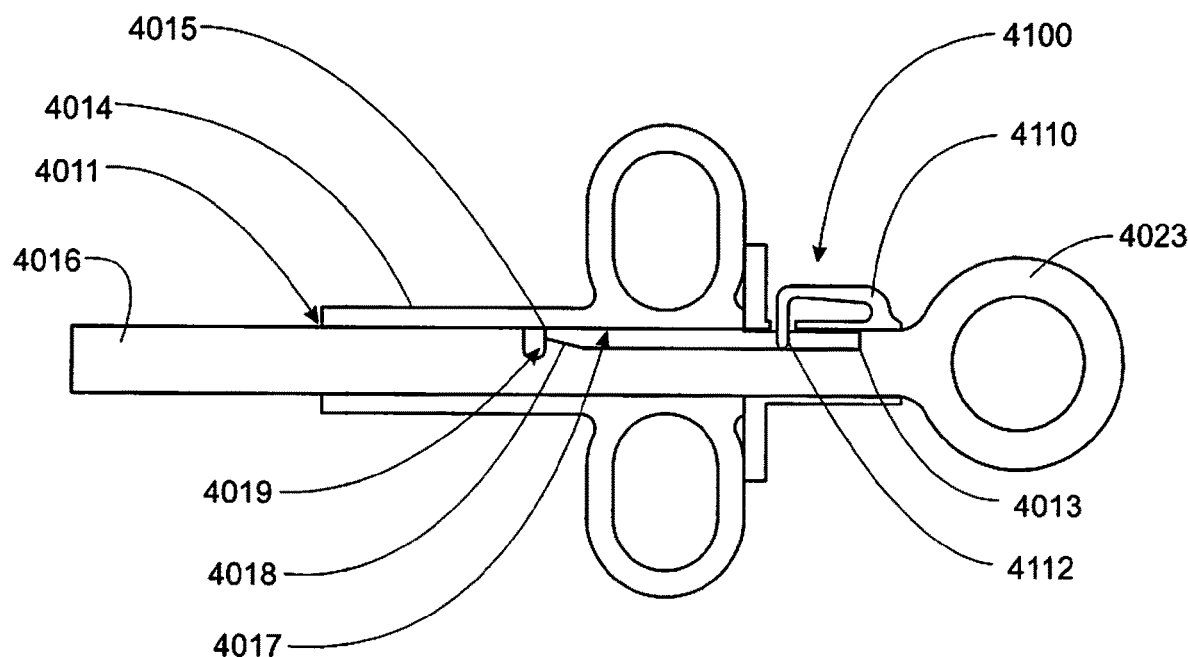
Figure 35A:
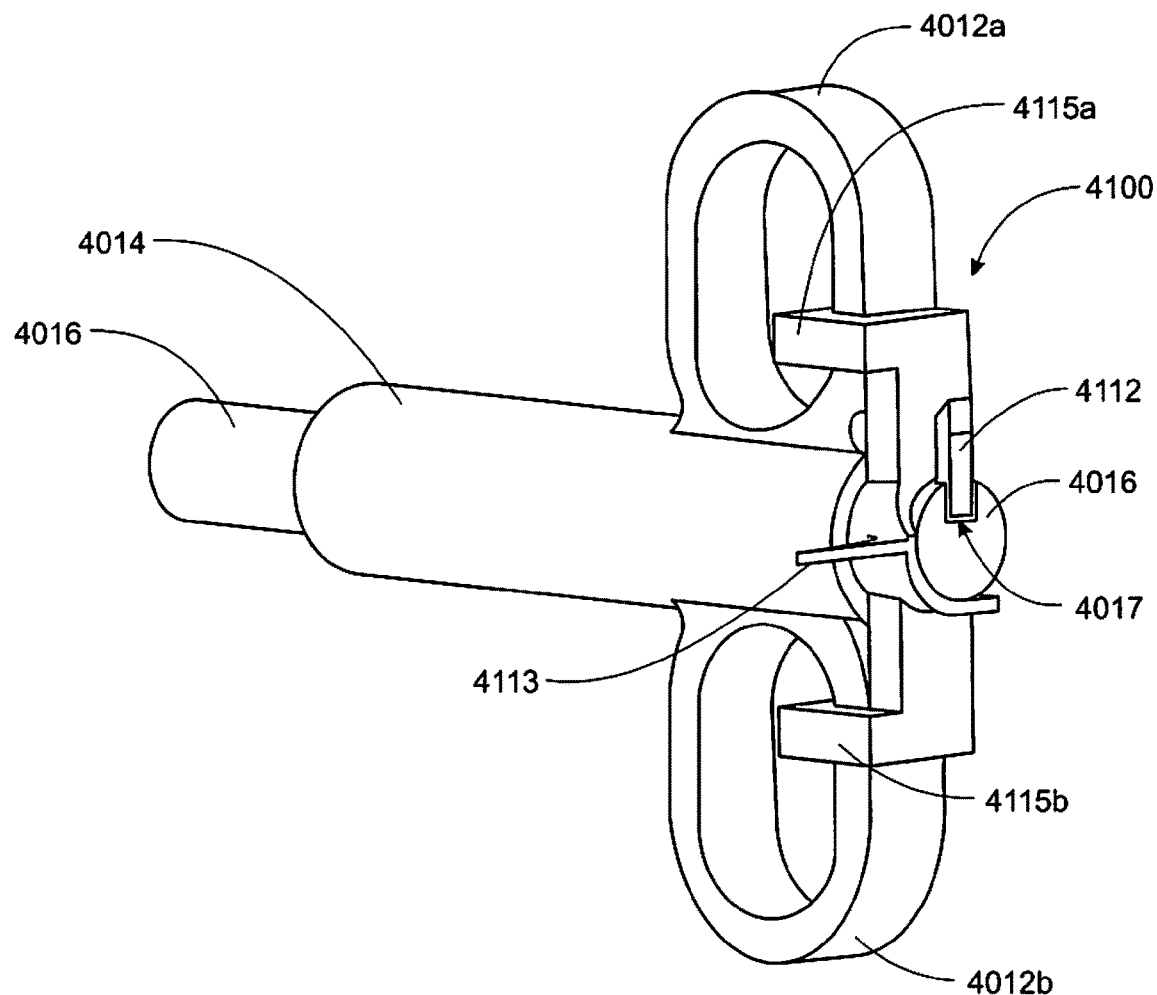
Figure 35B:
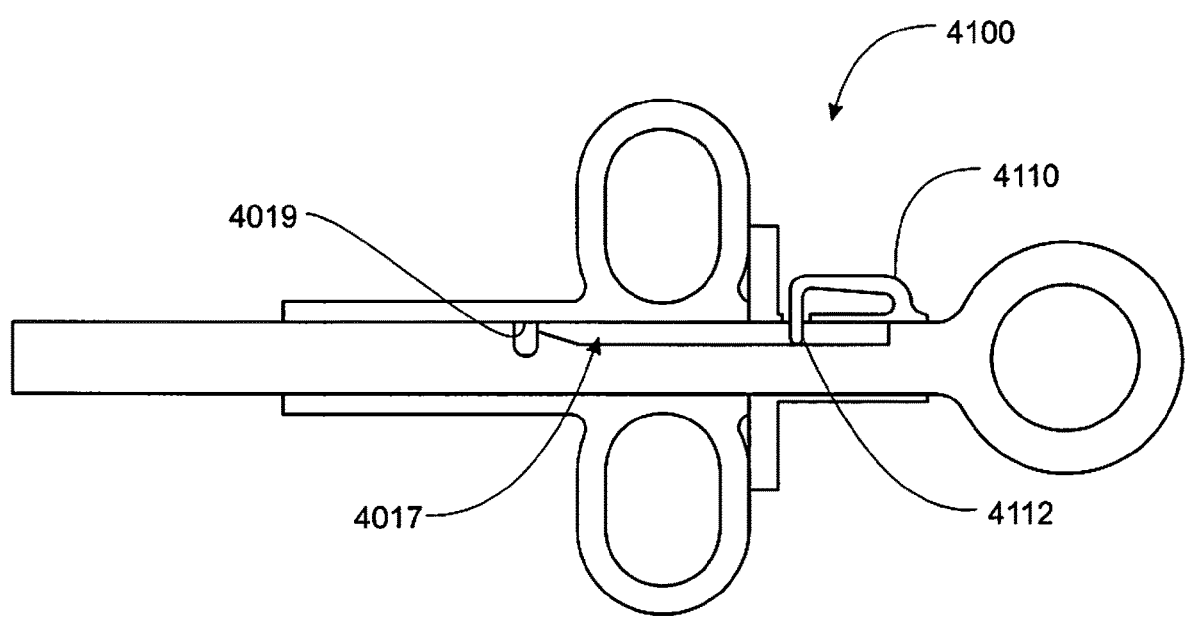
Figure 36B:
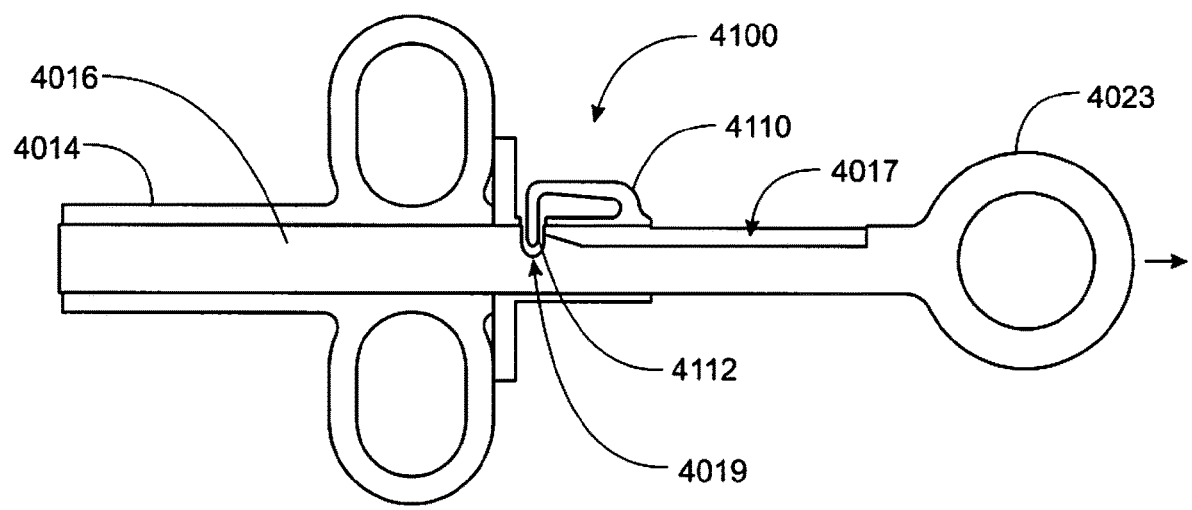
Figure 36A:
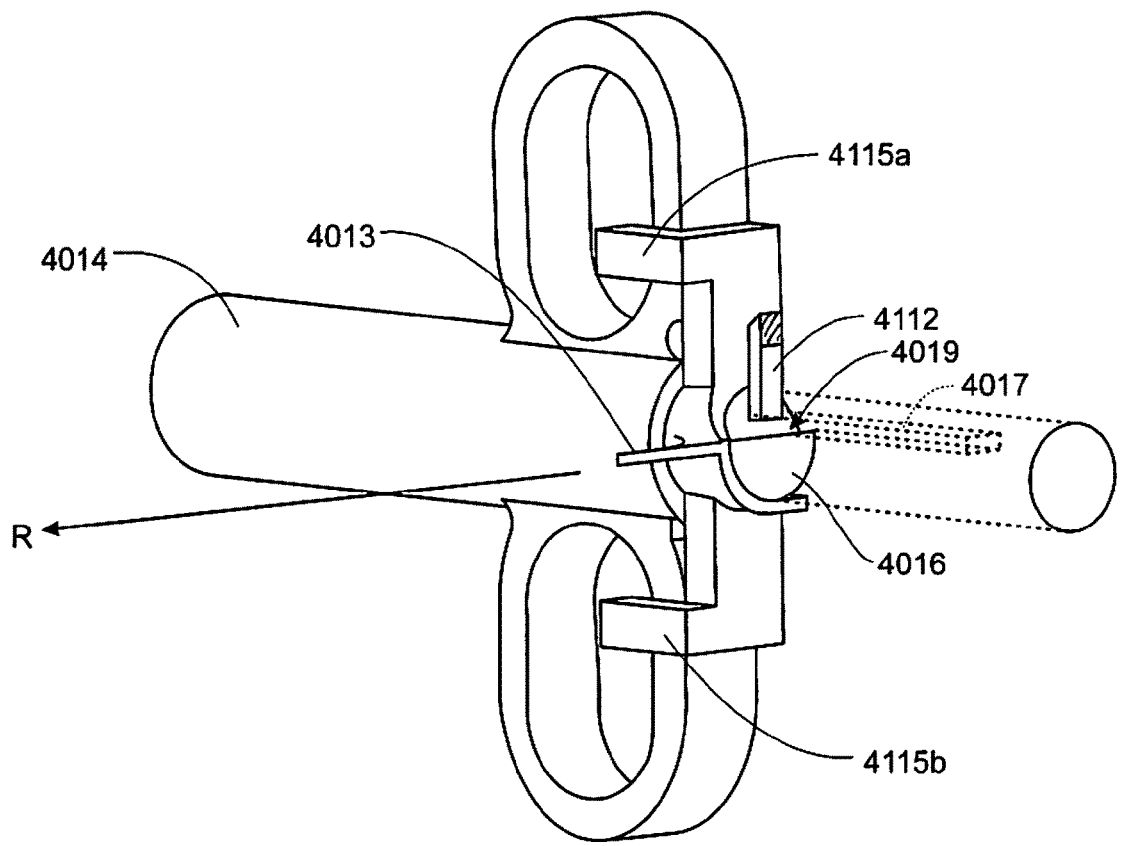
Figure 37:
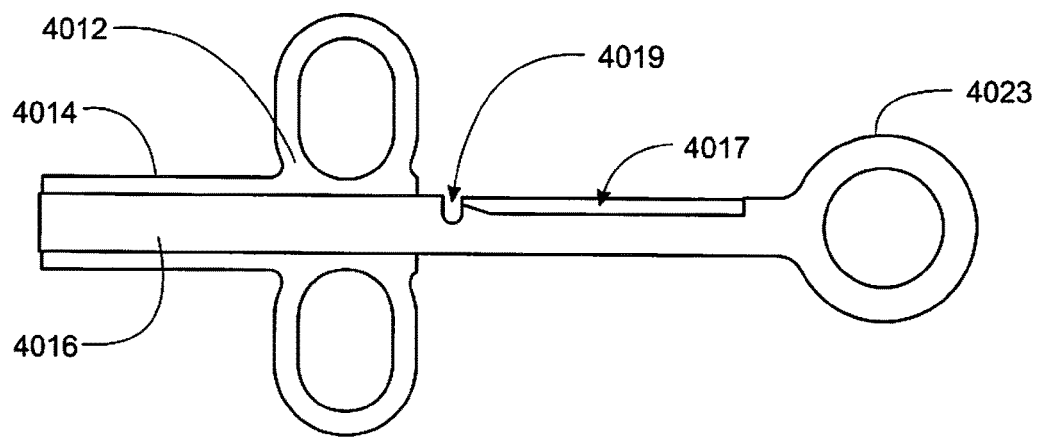
Figure 38:
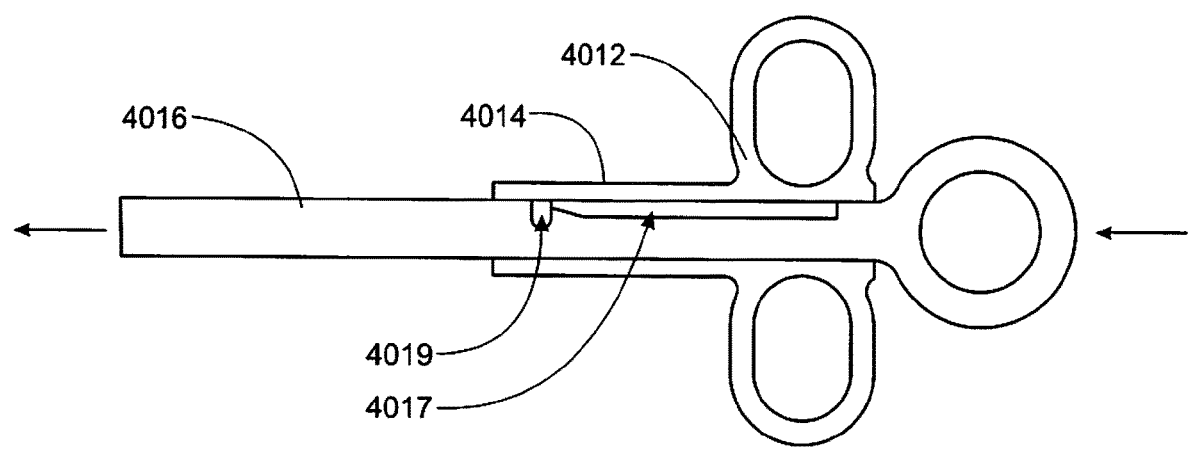

In use, housing 3012 is secured by a clinician with one hand and the proximal end 3023 of the inner shaft 3016 is retracted in relation to the housing 3012 to withdraw the specimen pouch 22, 122 into the distal end of the outer shaft 3014. As the inner shaft 3016 is retracted, the end 3115 of torsion spring 3100 rides distally along the first portion 3017 of the cam slot 3018 until the end 3115 of the torsion spring 3100 reaches the distal end of the first portion 3017 at the fully retracted position of the inner shaft 3016 (FIG. 30). At this point, the tension of the torsion spring 3100 causes movement of the end 3115 of torsion spring 3100 along the channel 321 of the cam slot 3018 from the first portion 3017 to the second portion 3019 of the cam slot 3018 (See FIGS. 30 and 31). The clinician is then free to translate the inner shaft 3016 distally as the end 3115 of the torsion spring 3100 translates along second portion 3019 of the cam slot 3018 an additional distance "X" (FIG. 28) (the length of the offset "X" between portions 3017 and 3019) to deploy the specimen pouch 22, 122 and the stripper plate from the outer shaft 3014 (See FIG. 33).

It is envisioned that one or more torsion or helical springs 3100 may be utilized to accomplish a similar purpose. Various known audible or tactile elements may be utilized to provide feedback to the clinician that the inner shaft 3016 is fully retracted and that the specimen pouch 22, 122 has been adequately withdrawn into the outer shaft 3014. For example, the clinician may feel or hear a snap or release as the torsion spring 3100 transitions from the first portion 3017 to the second portion 3019 of cam slot 3018 through the channel 321 of the cam slot 3018.

A method of deploying a specimen pouch 22, 122 of a specimen retrieval device 3000 is also disclosed and includes providing a specimen retrieval device 3000 including a housing 3012 and an outer shaft 3014 connected to the housing 3012 and extending distally therefrom, the outer shaft 3014 having a bore 3011 extending therethrough; providing an inner shaft 3016 disposed within the bore 3011 of the outer shaft 3014, the inner shaft 3016 being selectively translatable therethrough, the inner shaft 3016 including a support mechanism 28 (See FIG. 6) configured to releasably support a specimen pouch 22, 122 of the specimen retrieval device 3000 at a distal end thereof; the inner shaft 3016 including a cam slot 3018 defined in an outer periphery thereof, the cam slot 3018 including first and second portions 3017, 3019 defined within the inner shaft 3016 and extending therealong and a channel 3021 defined therebetween.

The method also includes: securing a first end 3120 of a torsion spring 3100 to the housing 3012 and positioning a second end 3115 of the torsion spring 3100 within the cam slot 3018, wherein the second end 3115 of the torsion spring 3100 is initially positioned at a proximal end of the first portion 3017 of the cam slot 3018 to prevent initial distal translation of the inner shaft 3016 relative to the housing 3012; proximally translating the inner shaft 3016 with respect to the housing 3012 to move the second end 3115 of the torsion spring 3100 within the cam slot 3018 from a first position located at the proximal end of the first portion 3017 of the cam slot 3018 to a second position located at a distal end of the first portion 3017 of the cam slot 3018 to allow the second end 3115 of the torsion spring 3100 to transition under the bias of the torsion spring 3100 along the channel 3021 from the distal end of the first portion 3017 into the distal end of the second portion 3019 of the cam slot 3018; and distally translating the inner shaft 3016 relative to the housing 3012 to deploy the specimen pouch 22, 122.

FIGS. 34A-38 illustrate another embodiment of a specimen retrieval device 4000 having a shipping lockout in the form of a removable shipping wedge 4100. Specimen retrieval device 4000 is similar to the specimen retrieval devices detailed above and, accordingly, only those features unique to specimen retrieval device 4000 are described herein. Specifically, a clinician must initially move the inner shaft 4016 from a partially retracted position (FIG. 34B) proximally in relation to the outer shaft 4014 to a retracted position (FIG. 36B) to withdraw the specimen pouch 22, 122 into the outer shaft 4014 and facilitate release of the shipping wedge 4100. Thereafter, the outer shaft 4014 may be positioned within a patient as described above and the specimen pouch 22, 122 subsequently deployed.

As with the other specimen retrieval devices described above, the inner shaft 4016 is prevented from moving distally from a partially refracted position or the shipping position until the specimen pouch 22, 122 is withdrawn into the outer shaft 4014 to facilitate positioning of the specimen retrieval device 4000 within a body cavity.

Specimen retrieval device 4000 includes a housing 4012 that supports outer and inner shafts 4014 and 4016. Inner shaft 4016 is selectively translatable through a longitudinal bore 4011 defined within the outer shaft 4014. The inner shaft 4016 defines a cam slot 4017 that extends longitudinally along its length. Cam slot 4017 includes proximal and distal ends 4013 and 4015, respectively. Each of the ends 4013 and 4015 defines a stop surface as will be discussed in further detail below. The distal end 4015 of the cam slot 4017 includes a ramp-like surface 4018 which transitions into a notch 4019. The shipping wedge 4100 is supported about the inner shaft 4016 between a handle 4023 of the inner shaft 4016 and the housing 4012 to prevent the inner shaft 4016 from being advanced to the extended position prior to the shipping wedge 4100 being removed from the device 4000. The notch 4019 is defined at a distal-most end of the cam slot 4017 and is configured to facilitate removal of the shipping wedge 4100 from the specimen retrieval device 4000 as described in detail below. The notch 4019 is positioned at the distal end of the cam slot 4017 and defines a stop surface 4019*a*

The shipping wedge 4100 includes a body 4105 defining a cutout 4105*a* (FIG. 34A) and having a flange 4110 extending from an upper surface of the body 4105. The flange 4110 has a resilient finger 4112 that extends into the cutout 4105. The finger 4112 extends downwardly from flange 4110 through the cutout 4105*a* and is dimensioned to ride within cam slot 4017 (See FIGS. 34B, 35A and 35B). The finger 4112 is inserted laterally into the notch 4019. Thereafter, the inner shaft 4016 is moved distally to position the finger 4112 in the cam slot 4017 to lock the shipping wedge 4100 onto the shipping device. More specifically, the shipping wedge 4100 must have the finger 4112 aligned with the notch 4019 to allow removal of the shipping wedge 4100 from the device 4000.

The shipping wedge 4100 includes one or more supports 4115*a* and 4115*b* (see FIG. 34A) that extend from the body 4105 of shipping wedge 4100. Each of the supports is configured to engage the housing 4012, e.g., finger rings 4012*a* and 4012*b* (see FIG. 35A). Supports 4115*a* and 4115*b* are configured to mount the shipping wedge 4100 to the housing 4012. A removal tab 4113 is disposed on the body 4105 which is configured to allow the shipping wedge 4100 to be grasped and laterally removed from the device 4000.

Prior to use, engagement of the finger 4112 with the proximal end 4013 of the cam slot 4017 prevents further advancement of the inner shaft 4016 in relation to the outer shaft 4014 to the extended position. In use, housing 4012 is grasped by a clinician with one hand and the proximal end or handle 4023 of the inner shaft 4016 is retracted to withdraw the specimen pouch 22, 122 (FIG. 7) into the distal end of the outer shaft 4014. As the inner shaft 4016 is retracted, finger 4112 of the flange 4110 rides within cam slot 4017 until the finger 4112 engages the ramp-like surface 4018. Ramp-like surface 4018 deforms the finger 4112 to provide a tactile feedback to the clinician that the finger 4112 is approaching the notch 4019 at the distal end of cam slot 4017. When the resilient finger 4112 snaps over ramp-like surface 4018, the positioning of the finger 4112 between the stop surface 4019*a* and the distal end of the cam slot 4017 prevents the inner shaft 4016 from being advanced or retracted in relation to the outer shaft 4014 prior to the shipping wedge 4100 being removed from the device 4000.

Once the inner shaft 4016 is moved to the retracted position to position the resilient finger 4112 in the notch 4119, the clinician may pull the removal tab 4113 of the shipping wedge 4100 laterally in the direction "R" (FIG. 36A) to remove the shipping wedge 4100 from the specimen retrieval device 4000. Once removed, the clinician is then free to translate the inner shaft 4016 distally to deploy the specimen pouch 22, 122 from the outer shaft 4014 (See FIGS. 37 and 38). A method of preventing inadvertent deployment of a specimen pouch 22, 122 of a specimen retrieval device 4000 is also disclosed and includes supporting a removable shipping wedge 4100 on a housing 4012 of a specimen retrieval device such that a finger 4112 of a spring-like flange 4110 of the shipping wedge 4100 is disposed within a cam slot 4017 defined in an inner shaft of the device, with the finger 4112 in abutting relation with a proximal end 4013 of a cam slot 4017 to prevent initial distal translation of the inner shaft 4016 relative to the housing 4012.

A method of deploying a specimen pouch 22, 122 of a specimen retrieval device 4000 is also disclosed and includes providing a specimen retrieval device 4000 having a housing 4012 and an outer shaft 4014 connected to the housing 4012 and extending distally therefrom, the outer shaft 4014 defining a longitudinal bore 4011 extending therethrough. An inner shaft 4016 is disposed within the bore 4011 of the outer shaft 4016 and is translatable therethrough, the inner shaft 4016 including a support mechanism 28 (FIGS. 7-11) configured to releasably support a specimen pouch 22, 122 of the specimen retrieval device 4000 at the distal end thereof. The inner shaft 4016 also defines a cam slot 4017 that extends therealong, the cam slot 4017 including a proximal end 4013 and a distal end 4015 having a notch 4019 defined therein. A removable shipping wedge 4100 having a body 4105 is secured about the inner shaft 4016 between a handle 4023 of the inner shaft 4016 and the housing 4012. The shipping wedge 4100 includes a spring-like flange 4110 which extends from an upper surface thereof having a finger 4112 at a distal end of the flange 4110, the finger 4112 being dimensioned to ride within the cam slot 4017. One or more supports 4115*a* and 4115*b* extend from opposing ends of the body 4105 and each support 4115*a* and 4115*b* is configured to engage an opposing side of the housing 4012.

The method also includes: engaging the removable shipping wedge 4100 to the housing 4012 and the inner shaft 4016 such that the finger 4112 of the spring-like flange 4110 is disposed in abutting relation with the proximal end 4013 of the cam slot 4017 to prevent initial distal translation of the inner shaft 4016 relative to the housing 4012; retracting the inner shaft 4016 relative to the housing 4012 such that the finger 4112 of the spring-like flanges 4110 rides along the cam slot 4017 and bottoms out in the notch 4019 at a distal end of the cam slot 4017; removing the shipping wedge 4100 from the housing 4012 and the inner shaft 4016; and distally translating the inner shaft 4016 with respect the housing 4012 to deploy the specimen pouch 22, 122.

In addition to the foregoing, the specimen retrieval devices, 10, 110, 210, 310, 410, 1000, 2000, 3000 and 4000 may be configured for use with other pouch configurations and/or release mechanisms. Such pouch configurations and their associated release mechanisms are described in commonly-owned U.S. Provisional Patent Application No. 61/771,129 entitled "Specimen Retrieval Device With Pouch Stop," filed by Malkowski et al. on Mar. 1, 2013, which is hereby incorporated by reference in its entirety.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the invention is not to be limited by what has been particularly shown and described, except as indicated by the appended claims.

What is claimed is:

1. A specimen retrieval device, comprising:
a housing;
an outer shaft extending distally from the housing, the outer shaft defining a longitudinal bore;
an inner shaft movably disposed within the longitudinal bore of the outer shaft;
a support mechanism secured to a distal end of the inner shaft;
a specimen pouch supported by the support mechanism;
first and second interfaces spaced longitudinally on the inner shaft; and
a cam lock pivotally coupled to the housing and movable from a first position wherein the cam lock is positioned to engage the first interface of the inner shaft to prevent distal translation of the inner shaft relative to the housing to an extended position, to a second position wherein the cam lock is positioned to allow distal translation of the inner shaft relative to the housing to the extended position to facilitate deployment of the specimen pouch, wherein proximal translation of the inner shaft within the outer shaft from a partially retracted position to a fully retracted position causes the second interface of the inner shaft to engage and move the cam lock to the second position.

2. The specimen retrieval device according to claim 1, wherein the cam lock is rotatable from the first position to the second position about a pivot member coupled to the housing.

3. The specimen retrieval device according to claim 2, wherein the cam lock defines a pivot hole, the pivot member being received within the pivot hole to pivotally couple the cam lock to the housing, at least one of the pivot hole and the pivot member being shaped such that rotation of the cam lock relative to the pivot causes the pivot to frictionally engage the cam lock to lock the cam lock in the second position.

4. The specimen retrieval device according to claim 1, wherein the cam lock includes first and second portions, wherein in the first position of the cam lock, the first portion is positioned to cooperate with the first interface of the inner shaft to prevent distal translation of the inner shaft relative to the housing to the extended position and the first portion is positioned to cooperate with the second interface to rotate the cam lock to the second position upon proximal translation of the inner shaft from the partially retracted position to the fully retracted position to allow subsequent distal translation of the inner shaft relative to the housing.

5. The specimen retrieval device according to claim 4, wherein the second portion of the cam lock is positioned and configured to lock the cam lock in the second position.

6. The specimen retrieval device according to claim 5, wherein the second portion of the cam lock is positioned offset relative to the first plane and is configured to engage a side of the inner shaft to prevent rotation of the cam lock, from the first position in a direction away from the second position to prevent distal translation of the inner shaft.

7. The specimen retrieval device according to claim 5, wherein the first portion of the cam lock has dimensions different from the second portion of the cam lock.

8. A specimen retrieval device, comprising:
a housing;
an outer shaft connected to the housing and extending distally therefrom, the outer shaft defining a longitudinal bore extending therethrough; an inner shaft movably disposed within the longitudinal bore of the outer shaft and translatable therethrough;
a support mechanism configured to releasably support a specimen pouch at a distal end of the inner shaft;
an first interface disposed on the inner shaft; and
a cam lock pivotably coupled to the housing and moveable from a first position wherein the cam lock prevents distal translation of the inner shaft relative to the housing to a second position wherein the cam lock allows distal translation of the inner shaft relative to the housing to facilitate deployment of the specimen pouch, the cam lock including first and second portions, the first portion cooperating with the first interface to rotate the cam lock to the second position upon proximal translation of the inner shaft to allow subsequent distal translation of the inner shaft relative to the housing and the second portion of the cam lock cooperating with a side of the inner shaft to prevent initial distal translation of the inner shaft relative to the housing when the cam lock is disposed in the first position.

9. The specimen retrieval device according to claim 8, further including a second interface disposed on the inner shaft proximally of the first interface, the first portion of the cam lock cooperating with the second interface to prevent distal translation of the inner shaft when the cam lock is in the first position.

10. The specimen retrieval device according to claim 9, wherein the first portion of the cam lock is disposed within a first plane and is configured to cooperate with the first and second interfaces positioned on a top of the inner shaft and the second portion is offset relative to the first plane and is configured to cooperate with a side of the inner shaft.

11. A specimen retrieval device, comprising:
a housing;
an outer shaft extending distally from the housing, the outer shaft defining a longitudinal bore;
an inner shaft movably disposed within the longitudinal bore of the outer shaft, the inner shaft defining a channel;
a support mechanism supported on a distal end of the inner shaft;
a specimen pouch supported at a distal end of the inner shaft;
first and second interfaces disposed at respective proximal and distal ends of the channel of the inner shaft;
a cam lock pivotably coupled to the housing and moveable from a first position wherein the cam lock is positioned to prevent distal translation of the inner shaft relative to the housing to a second position wherein the cam lock is positioned to allow distal translation of the inner shaft relative to the housing to facilitate deployment of the specimen pouch, the cam lock including first and second portions, the first portion extending into the channel and cooperating with the first interface to prevent initial distal translation of the inner shaft relative to the housing when the cam lock is disposed in the first position, and the first portion cooperating with the second interface to effect movement of the cam lock from the first position to the second position upon proximal translation of the inner shaft to allow distal translation of the inner shaft relative to the housing; and a spring coupled to the housing and cooperating with the second portion of the cam lock to retain the cam lock in the second position upon full proximal translation of the inner shaft relative to the housing.

12. The specimen retrieval device according to claim 11, wherein the second portion of the cam lock rotates against the bias of the spring as the cam lock moves from the first position to the second position, the second portion of the cam lock including a distal end configured to lock against the spring once the cam lock is rotated to the second position.

* * * * *